US012372465B2

(12) United States Patent
Atwood

(10) Patent No.: US 12,372,465 B2
(45) Date of Patent: Jul. 29, 2025

(54) COMPOSITIONS AND METHODS BASED ON DIFFUSION OF FLUOROPHORES

(71) Applicant: Scintimetrics, Inc., San Diego, CA (US)

(72) Inventor: Christopher Gordon Atwood, San Diego, CA (US)

(73) Assignee: SCINTIMETRICS, INC., San Diego, CA (US)

( * ) Notice: Subject to any disclaimer, the term of this patent is extended or adjusted under 35 U.S.C. 154(b) by 568 days.

(21) Appl. No.: 17/776,565

(22) PCT Filed: Nov. 13, 2020

(86) PCT No.: PCT/US2020/060531
§ 371 (c)(1),
(2) Date: May 12, 2022

(87) PCT Pub. No.: WO2021/097301
PCT Pub. Date: May 20, 2021

(65) Prior Publication Data
US 2022/0404281 A1    Dec. 22, 2022

Related U.S. Application Data

(60) Provisional application No. 63/052,310, filed on Jul. 15, 2020, provisional application No. 63/022,324, (Continued)

(51) Int. Cl.
*G01N 21/64* (2006.01)
*G01N 33/58* (2006.01)

(52) U.S. Cl.
CPC ..... *G01N 21/6428* (2013.01); *G01N 21/6489* (2013.01); *G01N 33/588* (2013.01);
(Continued)

(58) Field of Classification Search
CPC .......... G01N 21/6428; G01N 21/6489; G01N 33/588; G01N 2021/6434; G01N 2021/6497; G01N 2201/106
See application file for complete search history.

(56) References Cited

U.S. PATENT DOCUMENTS 5,641,640 A    6/1997  Hanning
5,965,456 A   10/1999  Malmqvist
(Continued)

FOREIGN PATENT DOCUMENTS

EP    1362634    11/2003
EP    1757357     2/2007
(Continued)

OTHER PUBLICATIONS

U.S. Appl. No. 62/768,743, filed Nov. 16, 2018 by Christopher Gordon Atwood.
(Continued)

*Primary Examiner* — Paul M. West
(74) *Attorney, Agent, or Firm* — Morrison & Foerster LLP

(57) ABSTRACT

The present disclosure provides a method for detection of an analyte in a sample, where the sample is introduced into an analytic chamber along with droplets of an emulsion or gel beads. In another aspect, the present disclosure provides designs for formulations of emulsion drops or gel beads such that they are useful for detection of analytes in a massively parallel manner. Formulations that contain specific combinations of fluorescent particles allow optical determination of the identity of each fluorescent particle. The combinations are based on particle fluorescence emission wavelength, fluorescence excitation wavelength, and particle count.

19 Claims, 32 Drawing Sheets

Related U.S. Application Data filed on May 8, 2020, provisional application No. 62/935,766, filed on Nov. 15, 2019.

(52) U.S. Cl.
CPC ............... *G01N 2021/6434* (2013.01); *G01N 2021/6497* (2013.01); *G01N 2201/106* (2013.01)

(56) References Cited

U.S. PATENT DOCUMENTS

| | | |
|---|---|---|
| 6,020,141 A | 2/2000 | Pantoliano et al. |
| 6,036,920 A | 3/2000 | Pantoliano et al. |
| 6,127,183 A | 10/2000 | Ivarsson |
| 6,214,293 B1 | 4/2001 | Pantoliano et al. |
| 6,493,097 B1 | 12/2002 | Ivarsson |
| 6,589,798 B1 | 7/2003 | Lofas |
| 6,632,609 B2 | 10/2003 | Lizardi |
| 6,714,303 B2 | 3/2004 | Ivarsson |
| 6,775,003 B2 | 8/2004 | Ivarsson |
| 6,999,175 B2 | 2/2006 | Ivarsson |
| 7,012,694 B2 | 3/2006 | Ivarsson |
| 7,081,958 B2 | 7/2006 | Ivarsson |
| 7,262,866 B2 | 8/2007 | Ivarsson |
| 7,268,167 B2 | 9/2007 | Higuchi et al. |
| 7,373,255 B2 | 5/2008 | Karlsson et al. |
| 7,375,140 B2 | 5/2008 | Higuchi et al. |
| 7,645,868 B2 | 1/2010 | Kobler et al. |
| 7,717,615 B2 | 5/2010 | Higuchi et al. |
| 7,718,262 B2 | 5/2010 | Chandler et al. |
| 7,772,287 B2 | 8/2010 | Higuchi et al. |
| 8,283,037 B2 | 10/2012 | Chandler et al. |
| 8,568,881 B2 | 10/2013 | Chandler et al. |
| 8,624,014 B2 | 1/2014 | Kobler et al. |
| 8,741,192 B2 | 6/2014 | Torii et al. |
| 8,968,874 B2 | 3/2015 | Chandler et al. |
| 9,364,803 B2 | 6/2016 | Yurkovetsky et al. |
| 9,376,613 B2 | 6/2016 | Chandler et al. |
| 9,658,219 B2 | 5/2017 | Verschuren |
| 9,664,667 B2 | 5/2017 | Walt et al. |
| 2007/0195127 A1 | 8/2007 | Ahn |
| 2008/0011977 A1 | 1/2008 | Atwood |
| 2011/0059435 A1 | 3/2011 | Vogelstein et al. |
| 2012/0164680 A1 | 6/2012 | McNaughton et al. |
| 2014/0186822 A1 | 7/2014 | Atwood |
| 2014/0248632 A1 | 9/2014 | Kopelman et al. |
| 2015/0010903 A1 | 1/2015 | Schawaller et al. |
| 2015/0112612 A1 | 4/2015 | Walt et al. |
| 2017/0329122 A1* | 11/2017 | Osawa .................. G02B 21/125 |
| 2017/0336403 A1 | 11/2017 | Atwood |
| 2019/0060861 A1 | 2/2019 | Kung et al. |
| 2019/0226988 A1* | 7/2019 | Iwamoto ................ G01N 21/77 |
| 2020/0158736 A1 | 5/2020 | Atwood |
| 2020/0401785 A1* | 12/2020 | Woehler ............... G01B 11/026 |
| 2021/0349023 A1* | 11/2021 | Frederix ................ G01N 21/78 |

FOREIGN PATENT DOCUMENTS

| | | |
|---|---|---|
| WO | WO 2002/068104 A1 | 9/2002 |
| WO | WO 2005/089921 A1 | 9/2005 |
| WO | WO-2012/156744 | 11/2012 |
| WO | WO-2014/132053 | 9/2014 |
| WO | WO-2018/154021 | 8/2018 |
| WO | WO 2018/208687 A1 | 11/2018 |
| WO | WO 2021/097301 A1 | 5/2021 |

OTHER PUBLICATIONS

U.S. Appl. No. 62/768,754, filed Nov. 16, 2018 by Christopher Gordon Atwood.
Abraham L. et al., "Limitations of Qdot labeling compared to directly-conjugated probes for single particle tracking of B cell receptor mobility", Scientific Reports, 2017, 7, 11379.
Anand V. et al., "Electrocoalescence of a pair of conducting drops in an insulating oil", Journal of Fluid Mechanics, 2019, 859, 839-850.
Bharadwaj P. et al., "Robustness of Quantum Dot Power-Law Blinking", Nano. Lett., 2011, 11, 2137-2141.
Chen K. et al., "Characteristic rotational behaviors of rod-shaped cargo revealed by automated five-dimensional single particle tracking", Nature Communications, 2017, 8, 887.
Choe H. et al., "Real-time Monitoring of Colloidal Nanoparticles using Light Sheet Dark-field Microscopy Combined with Microfluidic Concentration Gradient Generator", Bull. Korean Chem. Soc., 2014, 35, 365.
Chou S. S. et al., "Nanoscale Graphene Oxide (nGO) as Artificial Receptors: Implications for Biomolecular Interactions and Sensing", J. Am. Chem. Soc., 2012, 134, 16725-16733.
Daniel J. et al., "Innovative molecular-based fluorescent nanoparticles for multicolor single particle tracking in cells", J. Phys. D: Appl. Phys., 2016, 49, 084002.
Fedosov I. V. et al., "Measurements of the Diffusive Coefficient of Nanoparticles by Selective Plane Illumination Microscopy", Optics and Spectroscopy, 2009, 107, 846-852.
Frantsuzov P. et al., "Explanation of quantum dot blinking without the long-lived trap hypothesis", Phys. Rev. B, 2005, 72, 155321.
Friedrich M. et al., "Detection of Single Quantum Dots in Model Systems with Sheet Illumination Spectroscopy", J. Fluoresc., 2018, 27, 29-39.
Gammon D. et al., "Fine Structure Splitting in the Optical Spectra of Single GaAs Quantum Dots", Phys. Rev. Letters, 1996, 76, 3005.
Gardini L. et al., "3D tracking of single nanoparticles and quantum dots in living cells by out-of-focus imaging with diffraction pattern recognition", Nature Scientific Reports, 2015, 5, 16088.
Gu T. et al., "Electrically controlled mass transport into microfluidic droplets from nanodroplet carriers with application in controlled nanoparticle flow synthesis", Lab on a Chip, 2018, 18, 1330-1340.
Guasto J. S. et al., "Statistical particle tracking velocimetry using molecular and quantum dot tracer particles", Exp. Fluids, 2006, 41, 869-880.
Hayat Z. et al., "Fast Active Merging of Microdroplets in Microfluidic Chambers Driven by Photo-Isomerisation of Azobenzene Based Surfactants", Biosensors, 2019, 9, 129.
Hohng S. et al., "Near-Complete Suppression of Quantum Dot Blinking in Ambient Conditions", J. Am. Chem. Soc. Comm., 2004, 126, 1324-1325.
Hong B. J. et al., "Nanoscale-Controlled Spacing Provides DNA Mircoarrays with SNP Discrimination Efficiency in Solution Phase", Langmuir, 2005, 21, 10, 4257-4261.
Karakoti A. S. et al., "Surface functionalization of quantum dots for biological applications", Advances in Colloid and Interface Science, 2015, 215, 28-45.
Kazemipour A. et al., "Kilohertz frame-rate two-photon tomography", Nature, 2019, 16, 778-786.
Keller A. M. et al., "Multicolor Tree-Dimensional Tracking for Single-Molecule Fluorescence Resonance Energy Transfer Measurements", Anal. Chem., 2018, 90, 6109-6115.
Kovtun O. et al., "Single quantum dot tracking illuminates neuroscience at the nanoscale", Chemical Physics Letters, 2018, 706, 741-752.
Kulesa A., "Combinatorial Drug Discovery in Nanoliter Droplets", Proceedings of the National Academy of Sciences, 2018, 115 (26), 6685-6690.
Labreque S. et al., "Hyperspectral multiplex single-particle tracking of different receptor subtypes labeled with quantum dots in live neurons", J. Biomed. Opt., 2016, 21, 046008.
Lee J. et al., "Stable, small, specific, low-valency quantum dots for single-molecule imaging", Nanoscale, 2018, 10, 4406.
Li H. et al., "Multilayer nano-particle image velocimetry", Experiments in Fluids, 2006, 41, 185-194.
Li W, "Single-frame wide-field nanoscopy based on ghost imaging via sparsity constraints", Optica, 2019, 6, 1515.
Ma F. et al., "Development of quantum dot-based biosensors: principles and applications", J. Mater. Chem. B, 2018, 6, 6173.
McCarthy L. A. et al., "Polarized evanescent waves reveal trochoidal dichroism", PNAS, 2020, 117 (28), 16143.

(56) References Cited

OTHER PUBLICATIONS

Ming K. et al., "Integrated Quantum Dot Barcode Smartphone Optical Device for Wireless Multiplexed Diagnosis of Infected Patients", ACS Nano, 2015, 9, 3060-3074.

Pouya S. et al.; "Single Quantum Dot Imaging of Fluid Flow Near Surfaces", Experiments in Fluids, 2005, 39, 784-786.

Ranchon H. et al., "Metrology of confined flows using wide field nanoparticle velocimetry", Nano Scientific Reports, 2015, 5, 10128.

Reid K. R. et al., "Chemical Structure, Ensemble and Single-Particle Spectroscopy of Thick-Shell InP—ZnSe Quantum Dots", Nano. Lett., 2018, 18, 2, 709-716. & Interfaces, 2019, 11, 6, 6238-6247.

Schuster B. S. et al., "Particle tracking in drug and gene delivery research: State-of-the-art applications and methods", Advanced Drug Delivery Reviews, 2015, 91, 70-91.

Sesen M. et al., "Droplet control technologies for microfluidic high throughput screening (µHTS)", Lab on a Chip, 2017, 17, 2372-2394.

Speicher M. R. et al., "Karyotyping human chromosomes by combinatorial multi-flour FISH", Nature Genetics, 1996, 12, 368-375.

Stefani F. D. et al., "Quantification of phootinduced and spontaneous quantum-dot luminescence blinking", Physical Review B, 2005, 72, 125304.

Thomas E. M. et al., "Blinking Suppression in Highly Excited CdSe/ZnS Quantum Dots by Electron Transfer under Large Positive Gibbs (Free) Energy Change", ACS Nano, 2018, 12, 9, 9060-9069.

Velev O. D. et al., "On-chip micromanipulation and assembly of colloidal particles by electric fields", Soft Matter, 2006, 2, 738-750.

Von Diezmann L. et al., "Three-Dimensional Localization of Single Molecules for Super-Resolution Imaging and Single-Particle Tracking", Chem. Rev., 2017, 117, 7244.

Wereley S. T. et al., "Recent Advances in Micro-Particle Image Velocimetry", Annu. Rev. Fluid Mech. 2010, 42, 557-576.

Williams S. J. et al., "Advances and applications on microfluidic velocimetry techniques", Microfluid Nanofluid, 2010, 8, 709-726.

Xu Q. et al., "Multicolor Quantum Dot-Based Chemical Nose for Rapid and Array-Free Differentiation of Multiple Proteins", Anal. Chem., 2016, 88, 2051-2058.

Yu X. et al., "A Facile Approach to Fabrication of Bifunctional Magnetic-Optical $Fe_3O_4$@ZnS Microspheres", Chem. Mater., 2009, 21, 4892-4898.

Zahid M. U. et al., "Single quantum dot tracking reveals the impact of nanoparticle surface on intracellular state", Nature Communications, 2018, 9, 1830.

Zhang H. et al., "Electrochemistry of single droplets of inverse (water-in-oil) emulsions", Phys. Chem. Chem. Phys., 2017, 19, 15662-15666.

Zhang H. et al., "Se/S Ratio-Dependent Properties and Application of Gradient-Alloyed $CdSe_{1-x}S_x$ Quantum Dots: Shell-free Structure, Non-blinking Photoluminescence with Single-Exponential Decay, and Efficient QLEDs", ACS Applied Materials & Interfaces, 2019, 11, 6, 6238-6247.

Zhang L-J. et al., "Quantum Dot Based Biotracking and Biodetection", Anal. Chem., 2019, 91, 532-547.

Origene, "Flow Cytometry Protocol," Retrieved from the Internet: URL: https://cdn.origene.com/assets/documents/protocols/facs%20protocol.pdf, retrieved on Oct. 20, 2023, pp. 1-4.

\* cited by examiner

COMPOSITIONS AND METHODS BASED ON DIFFUSION OF FLUOROPHORES

CROSS-REFERENCE TO RELATED APPLICATIONS

This application is a national stage application under 35 U.S.C. § 371 of International Application No. PCT/US2020/060531, filed internationally on Nov. 13, 2020, which claims priority to U.S. Provisional Patent Application Ser. No. 62/935,766, filed Nov. 15, 2019, U.S. Provisional Patent Application Ser. No. 63/022,324, filed May 8, 2020, and U.S. Provisional Patent Application Ser. No. 63/052,310, filed Jul. 15, 2020, all of which are herein incorporated by reference in their entireties for all purposes.

FIELD

The present disclosure provides methods for the detection of analytes and their binding interactions, and designs of formulations for use in the methods, e.g., formulations comprising emulsion droplets and/or gel beads.

BACKGROUND

Samples of complex biological media, such as blood, contain specific components that are useful in diagnosing illnesses. The concentrations of these specific components need to be measured reliably despite the concomitant presence of much larger concentrations of similar components. These specific components as "analytes" may include proteins, small molecules, or nucleic acids. Measurement is commonly achieved by the use of complementary components that bind to the analytes. The complementary components are referred to as "analyte binding reagents". An example of an analyte and analyte binding reagent pair is an antigen and antibody.

Methods for measuring analyte concentrations of the specific components are known. However, some of these analytes may be biologically significant at presently undetectable concentrations, necessitating new techniques that have a high intrinsic sensitivity and specificity. Additionally, the complexity of the medium increases the risk of false positives and false negatives, which may be ameliorated by new techniques for disease marker diagnostics. Additionally, discovery of new disease markers and discovery of new drug therapies are research areas that would benefit from improved methods. The present disclosure addresses these and other needs.

SUMMARY

The present disclosure provides a method for detection of an analyte in a sample, where the sample is introduced into an analytic chamber along with droplets of an emulsion. The droplets contain fluorescent particles having surface-bound reagents that can bind to the analyte. The droplets are demulsified within the analytic chamber, and the reagents then bind to the analytes. The diffusivity of the fluorescent particles is lessened by the binding. Fluorescent excitation light of controlled phase or spatial patterning is passed through the analytic chamber, and fluorescence emission light passes out of the analytic chamber. The fluorescence emission light is imaged. As the fluorescent particles diffuse into and out of regions of high electric field, the fluorescence will vary. The variation in the fluorescence is a function of the diffusivity of the fluorescent particles, and hence provides information about the presence of the analyte. Conversely, these methods can also be used to determine if binding occurs among a diverse population of reagent candidates, when an analyte is explicitly provided.

A key feature of the present disclosure is it allows use of a massive library of reagents sourced from a simple vial, where mapping of the reagents to fluorescence emission behavior is achieved by imaging of diffusively expanding constellations of fluorescent particles. In another aspect, the present disclosure provides designs for formulations of emulsion drops or gel beads such that they are useful for detection of analytes in a massively parallel manner. Formulations that contain specific combinations of fluorescent particles allow optical determination of the identity of each fluorescent particle. The combinations are based on particle fluorescence emission wavelength, fluorescence excitation wavelength, and particle count.

In some embodiments, disclosed herein is a method for analyzing an analyte, comprising: contacting (i) a first composition comprising a liquid phase and a sample in the liquid phase, with (ii) a second composition comprising a liquid matrix and a formulation encapsulated in the liquid matrix, wherein the formulation comprises a plurality of fluorescent constructs and an analyte-interacting reagent attached to one or more of the fluorescent constructs; and combining the liquid phase and the formulation such that an analyte in the sample interacts with the analyte-interacting reagent attached to the one or more of the fluorescent constructs to generate a detectable signal, wherein the detectable signal is analyzed for detecting the presence or absence, an amount or concentration, and/or an activity of the analyte in the sample. In some embodiments, the analyte-interacting reagent is an analyte-binding reagent.

In any of the preceding embodiments, the liquid phase and the formulation can merge into a single fluid during the combining step. In any of the preceding embodiments, the analyte in the sample can specific bind to the analyte-interacting reagent.

In any of the preceding embodiments, the analyte in the sample and the analyte-interacting reagent can participate in a reaction, e.g., an enzymatic reaction catalyzed by the analyte, by the analyte-interacting reagent, and/or by an agent in the sample and/or the formulation.

In any of the preceding embodiments, the plurality of fluorescent constructs can comprise one or more fluorescent particle, one or more fluorescent small molecule, one or more fluorescent peptide or protein, one or more fluorescent dye, or any combination thereof.

In any of the preceding embodiments, the formulation can comprise one or more polymeric particle each comprising one or more fluorescent particle, one or more fluorescent small molecule, one or more fluorescent peptide or protein, one or more fluorescent dye, or any combination thereof.

In any of the preceding embodiments, the plurality of fluorescent constructs can comprise one or more fluorescent semiconductor nanoparticle. In any of the preceding embodiments, the plurality of fluorescent constructs can comprise one or more quantum dot.

In any of the preceding embodiments, the analyte-interacting reagent can be directly attached to the one or more of the fluorescent constructs.

In any of the preceding embodiments, the analyte-interacting reagent can be indirectly attached to the one or more of the fluorescent constructs, e.g., via a linker or a common binding partner.

In any of the preceding embodiments, the analyte-interacting reagent can be covalently or non-covalently attached to the one or more of the fluorescent constructs.

In any of the preceding embodiments, each of the one or more of the fluorescent constructs can have one or more analyte-interacting reagent attached thereto, or only a subset of the one or more of the fluorescent constructs has one or more analyte-interacting reagent attached thereto.

In any of the preceding embodiments, the second composition can comprise or be an emulsion, e.g., of the liquid matrix and the formulation, or the second composition can comprise or be a composition other than an emulsion.

In any of the preceding embodiments, the formulation can comprise or be an aqueous droplet.

In any of the preceding embodiments, the formulation can comprise or be a gel, e.g., in the form of a gel bead. In some embodiments, the gel comprises the plurality of fluorescent constructs and is capable of releasing the plurality of fluorescent constructs, e.g., upon melting or otherwise disintegrating the gel (e.g., de-polymerization of the gel such as by using enzymatic digestion).

In any of the preceding embodiments, the liquid phase can be water and the formulation can be soluble in and/or miscible with water, or the liquid matrix can be immiscible or substantially immiscible with water.

In any of the preceding embodiments, the liquid matrix can comprise a lipid, an oil, a hydrocarbon fluid, a fluorocarbon fluid, a chlorocarbon fluid, a bromocarbon fluid, an iodocarbon fluid, a silicone fluid, or a mixture thereof.

In any of the preceding embodiments, the liquid matrix can be selected from the group consisting of a lipid, an oil, a hydrocarbon fluid, a fluorocarbon fluid, a chlorocarbon fluid, a bromocarbon fluid, an iodocarbon fluid, a silicone fluid, and a mixture thereof.

In any of the preceding embodiments, the combination of the liquid phase and the formulation can occur in an analytic chamber.

In any of the preceding embodiments, the combining step can comprise combining adjacent streams of the first composition and the formulation, respectively.

In any of the preceding embodiments, the combining step can comprise combining transverse streams of the first composition and the formulation, respectively.

In any of the preceding embodiments, the combining step can comprise combining perpendicular streams of the first composition and the formulation, respectively.

In any of the preceding embodiments, the combining step can comprise combining oblique streams of the first composition and the formulation, respectively.

In any of the preceding embodiments, the combining step can comprise combining opposed streams of the first composition and the formulation, respectively.

In any of the preceding embodiments, the combining step can comprise combining concentric streams of the first composition and the formulation, respectively.

In any of the preceding embodiments, the first composition and/or the formulation can comprise one or more demulsifying agent.

In any of the preceding embodiments, the first composition and/or the formulation can comprise one or more gelling agent.

In any of the preceding embodiments, the first composition and/or the formulation can comprise one or more viscosity-enhancing agent.

In any of the preceding embodiments, the first composition can be a first emulsion comprising the liquid phase as an emulsified droplet within a first liquid matrix, and the liquid matrix of the second composition can be a second liquid matrix.

In any of the preceding embodiments, the first liquid matrix and the second liquid matrix can be the same or different.

In any of the preceding embodiments, the first liquid matrix and the second liquid matrix may be independently selected from the group consisting of a lipid, an oil, a hydrocarbon fluid, a fluorocarbon fluid, a chlorocarbon fluid, a bromocarbon fluid, an iodocarbon fluid, a silicone fluid, and any suitable combination thereof.

In any of the preceding embodiments, the combining step can comprise application of an electric field to the first and/or second compositions.

In any of the preceding embodiments, the first composition and the second composition can comprise surfactants of opposite charges, respectively, and the combining step can comprise contacting the surfactants of opposite charges with one another.

In any of the preceding embodiments, the combining step can comprise application of a demulsification agent to the first and/or second compositions, or the combining step may not comprise application of a demulsification agent.

In any of the preceding embodiments, the combining step can comprise application of heat to the first and/or second compositions.

In any of the preceding embodiments, the combining step can comprise application of a gel depolymerization agent to the first and/or second compositions.

In any of the preceding embodiments, the detectable signal may be a fluorescent signal.

In any of the preceding embodiments, the detectable signal can be induced by excitation light comprising, consisting essentially of, or consisting of non-polarized light.

In any of the preceding embodiments, the detectable signal can be induced by excitation light comprising, consisting essentially of, or consisting of linearly polarized light.

In any of the preceding embodiments, the detectable signal can be induced by excitation light comprising, consisting essentially of, or consisting of circularly polarized light.

In any of the preceding embodiments, the detectable signal can be induced by excitation light comprising, consisting essentially of, or consisting of elliptically polarized light and/or trochoidally polarized light.

In any of the preceding embodiments, the detectable signal can be induced by excitation light comprising, consisting essentially of, or consisting of light of a single wavelength.

In any of the preceding embodiments, the detectable signal can be induced by excitation light comprising, consisting essentially of, or consisting of polychromatic light.

In any of the preceding embodiments, the detectable signal can be induced by excitation light comprising, consisting essentially of, or consisting of non-coherent light.

In any of the preceding embodiments, the detectable signal can be induced by excitation light comprising, consisting essentially of, or consisting of coherent light.

In any of the preceding embodiments, the detectable signal can be induced by excitation light comprising, consisting essentially of, or consisting of continuous light.

In any of the preceding embodiments, the detectable signal can be induced by excitation light comprising, consisting essentially of, or consisting of pulsed light.

In any of the preceding embodiments, the detectable signal can be induced by excitation light comprising, consisting essentially of, or consisting of light applied at a single incident angle.

In any of the preceding embodiments, the detectable signal can be induced by excitation light comprising, consisting essentially of, or consisting of light applied at a set of incidence angles.

In any of the preceding embodiments, the method can comprise applying an external electric field to the combined composition, wherein the external electric field is sufficient to cause electrophoretic motion of the fluorescent constructs within the combined composition. In some embodiments, the external electric field comprises, consists essentially of, or consists of: (i) a constant electric field which is applied in a constant direction; (ii) a pulsed electric field which is applied in a constant direction; and/or (iii) an oscillating electric field which is applied in a constant direction.

In any of the preceding embodiments, the external electric field can comprise, consist essentially of, or consist of: (i) a constant electric field switching between multiple directions; (ii) a pulsed electric field switching between multiple directions; and/or (iii) an oscillating electric field switching between multiple directions.

In any of the preceding embodiments, the method can comprise applying a force to the combined composition, thereby reducing or eliminating non-specific interaction between the analyte molecules and the fluorescent constructs.

In any of the preceding embodiments, the method can comprise applying an acoustic wave to the combined composition, wherein the acoustic wave optionally comprises a high-frequency sound wave, e.g., an ultrasound.

In any of the preceding embodiments, the method can comprise applying a fluorescence excitation light to the combined composition. In some embodiments, the fluorescence excitation light is one used in confocal microscopy, Structured Illumination Microscopy (SIM), STochastic Optical Reconstruction Microscopy (STORM), Point-Scanning Two-Photon Microscopy, Scanned Line Angular Projection Microscopy (SLAPMi), Ghost Imaging (GI), and/or Ghost Imaging by Sparsity Constraints (GISC).

In any of the preceding embodiments, the method can comprise allowing the fluorescence emission light to be refracted or internally reflected by droplets having a refractive index different from the matrix, producing an image pattern that may be deconvoluted to identify the position of the fluorophore.

In some aspects, disclosed herein is a method for analyzing an analyte, comprising: contacting (i) a first composition comprising a liquid phase and a sample in the liquid phase, with (ii) a second composition comprising a liquid matrix and a formulation encapsulated in the liquid matrix, wherein the formulation comprises a plurality of fluorescent constructs and an analyte-interacting reagent attached to one or more of the fluorescent constructs; combining the liquid phase and the formulation in an analytic chamber, such that an analyte in the sample interacts with the analyte-interacting reagent attached to the one or more of the fluorescent constructs; directing an excitation light through the analytic chamber to cause fluorescence of the fluorescent constructs, wherein said fluorescence is dependent on fluorescent construct position within the local phase angle of the excitation light; detecting and/or measuring fluorescence emission as the fluorescent constructs within each formulation diffuse in the combined composition; determining the identity of each analyte-interacting reagent present within each formulation based on a pattern of fluorescent emission wavelengths during the diffusion, wherein a change in the stochastic behavior of the fluorescence emission provides an indication of presence or absence, an amount, and/or an activity of the analyte in the sample. In some embodiments, the excitation light is of controlled phase and wavelength. In any of the preceding embodiments, the excitation light can be or comprise a standing wave.

In any of the preceding embodiments, the excitation light can be coherent and the phase of the coherent excitation light may be controlled such that the crests and troughs of the excitation light are moved past the fluorescent constructs, sufficient to cause a corresponding oscillation in the fluorescence of the fluorescent constructs.

In any of the preceding embodiments, the excitation light can be an elliptically polarized coherent excitation light, and the ellipticity of the excitation light may be controlled such that the crests and troughs of the excitation light are moved past the fluorescent constructs, sufficient to cause a corresponding oscillation in the fluorescence of the fluorescent constructs.

In any of the preceding embodiments, the excitation light can be of controlled spatial pattern and/or of controlled wavelength. In some embodiments, the excitation light is applied as a patterned spatial array across the analytic chamber such that the light intensity varies for different points within the analytic chamber, sufficient to cause changes in the fluorescence of the fluorescent constructs as the fluorescent constructs move between different points within the analytic chamber.

In any of the preceding embodiments, the patterned spatial array of excitation light may be moved across the analytic chamber such that the light intensity varies with time and for different points within the analytic chamber, sufficient to cause changes in the fluorescence of the fluorescent constructs.

In any of the preceding embodiments, the detecting and/or measuring fluorescence emission can comprise detecting and/or measuring the magnitude of fluorescence emission.

In any of the preceding embodiments, the pattern of fluorescent emission wavelengths during the diffusion may be determined in the vicinity of where each formulation has combined with the liquid phase.

In any of the preceding embodiments, the liquid phase and the formulation may merge into a single fluid during the combining step.

In any of the preceding embodiments, the analyte in the sample may specifically bind to the analyte-interacting reagent.

In any of the preceding embodiments, the analyte in the sample and the analyte-interacting reagent may participate in a reaction, e.g., an enzymatic reaction catalyzed by the analyte, by the analyte-interacting reagent, and/or by an agent in the sample and/or the formulation.

In any of the preceding embodiments, the plurality of fluorescent constructs may comprise one or more fluorescent particle, one or more fluorescent small molecule, one or more fluorescent peptide or protein, one or more fluorescent dye, or any combination thereof.

In any of the preceding embodiments, the formulation may comprise one or more polymeric particle each comprising one or more fluorescent particle, one or more fluorescent small molecule, one or more fluorescent peptide or protein, one or more fluorescent dye, or any combination thereof.

In any of the preceding embodiments, the plurality of fluorescent constructs can comprise one or more fluorescent semiconductor nanoparticle.

In any of the preceding embodiments, the plurality of fluorescent constructs may comprise one or more quantum dot.

In any of the preceding embodiments, the analyte-interacting reagent may be directly attached to the one or more of the fluorescent constructs.

In any of the preceding embodiments, the analyte-interacting reagent may be indirectly attached to the one or more of the fluorescent constructs, e.g., via a linker or a common binding partner.

In any of the preceding embodiments, the analyte-interacting reagent may be non-covalently attached to the one or more of the fluorescent constructs.

In any of the preceding embodiments, the analyte-interacting reagent may be covalently attached to the one or more of the fluorescent constructs.

In any of the preceding embodiments, each of the one or more of the fluorescent constructs can have one or more analyte-interacting reagent attached thereto.

In any of the preceding embodiments, a subset of the one or more of the fluorescent constructs may have one or more analyte-interacting reagent attached thereto.

In any of the preceding embodiments, the second composition can comprise or be an emulsion, e.g., of the liquid matrix and the formulation.

In any of the preceding embodiments, the formulation can comprise or be an aqueous droplet.

In any of the preceding embodiments, the second composition may comprise or be a composition other than an emulsion.

In any of the preceding embodiments, the formulation can comprise or be a gel, e.g., in the form of a gel bead. In some embodiments, the gel comprises the plurality of fluorescent constructs and is capable of releasing the plurality of fluorescent constructs, e.g., upon melting or otherwise disintegrating the gel (e.g., de-polymerization of the gel such as by using enzymatic digestion).

In any of the preceding embodiments, the liquid phase can be water and the formulation can be soluble in and/or miscible with water.

In any of the preceding embodiments, the liquid matrix can be immiscible or substantially immiscible with water.

In any of the preceding embodiments, the liquid matrix can comprise a lipid, an oil, a hydrocarbon fluid, a fluorocarbon fluid, a chlorocarbon fluid, a bromocarbon fluid, an iodocarbon fluid, a silicone fluid, or a mixture thereof.

In any of the preceding embodiments, the liquid matrix may be selected from the group consisting of a lipid, an oil, a hydrocarbon fluid, a fluorocarbon fluid, a chlorocarbon fluid, a bromocarbon fluid, an iodocarbon fluid, a silicone fluid, and a mixture thereof.

In any of the preceding embodiments, the combination of the liquid phase and the formulation can occur in an analytic chamber.

In any of the preceding embodiments, the combining step can comprise combining adjacent streams of the first composition and the formulation, respectively.

In any of the preceding embodiments, the combining step can comprise combining transverse streams of the first composition and the formulation, respectively.

In any of the preceding embodiments, the combining step can comprise combining perpendicular streams of the first composition and the formulation, respectively.

In any of the preceding embodiments, the combining step can comprise combining oblique streams of the first composition and the formulation, respectively.

In any of the preceding embodiments, the combining step can comprise combining opposed streams of the first composition and the formulation, respectively.

In any of the preceding embodiments, the combining step can comprise combining concentric streams of the first composition and the formulation, respectively.

In any of the preceding embodiments, the first composition and/or the formulation can comprise one or more demulsifying agent.

In any of the preceding embodiments, the first composition and/or the formulation can comprise one or more gelling agent.

In any of the preceding embodiments, the first composition and/or the formulation can comprise one or more viscosity-enhancing agent.

In any of the preceding embodiments, the first composition can be a first emulsion comprising the liquid phase as an emulsified droplet within a first liquid matrix, and the liquid matrix of the second composition can be a second liquid matrix.

In any of the preceding embodiments, the first liquid matrix and the second liquid matrix can be the same or different.

In any of the preceding embodiments, the first liquid matrix and the second liquid matrix may be independently selected from the group consisting of a lipid, an oil, a hydrocarbon fluid, a fluorocarbon fluid, a chlorocarbon fluid, a bromocarbon fluid, an iodocarbon fluid, a silicone fluid, and any suitable combination thereof.

In any of the preceding embodiments, the combining step can comprise application of an electric field to the first and/or second compositions.

In any of the preceding embodiments, the first composition and the second composition can comprise surfactants of opposite charges, respectively, and the combining step comprises contacting the surfactants of opposite charges with one another.

In any of the preceding embodiments, the combining step can comprise application of a demulsification agent to the first and/or second compositions.

In any of the preceding embodiments, the combining step can be without application of a demulsification agent.

In any of the preceding embodiments, the combining step can comprise application of heat to the first and/or second compositions.

In any of the preceding embodiments, the combining step can comprise application of a gel depolymerization agent to the first and/or second compositions.

In any of the preceding embodiments, the detectable signal can be or comprise a fluorescent signal.

In any of the preceding embodiments, the detectable signal can be induced by excitation light comprising, consisting essentially of, or consisting of non-polarized light.

In any of the preceding embodiments, the detectable signal can be induced by excitation light comprising, consisting essentially of, or consisting of linearly polarized light.

In any of the preceding embodiments, the detectable signal can be induced by excitation light comprising, consisting essentially of, or consisting of circularly polarized light.

In any of the preceding embodiments, the detectable signal can be induced by excitation light comprising, consisting essentially of, or consisting of elliptically polarized light and/or trochoidally polarized light.

In any of the preceding embodiments, the detectable signal can be induced by excitation light comprising, consisting essentially of, or consisting of light of a single wavelength.

In any of the preceding embodiments, the detectable signal can be induced by excitation light comprising, consisting essentially of, or consisting of polychromatic light.

In any of the preceding embodiments, the detectable signal can be induced by excitation light comprising, consisting essentially of, or consisting of non-coherent light.

In any of the preceding embodiments, the detectable signal can be induced by excitation light comprising, consisting essentially of, or consisting of coherent light.

In any of the preceding embodiments, the detectable signal can be induced by excitation light comprising, consisting essentially of, or consisting of continuous light.

In any of the preceding embodiments, the detectable signal can be induced by excitation light comprising, consisting essentially of, or consisting of pulsed light.

In any of the preceding embodiments, the detectable signal can be induced by excitation light comprising, consisting essentially of, or consisting of light applied at a single incident angle.

In any of the preceding embodiments, the detectable signal can be induced by excitation light comprising, consisting essentially of, or consisting of light applied at a set of incidence angles.

In any of the preceding embodiments, the method can comprise applying an external electric field to the combined composition, wherein the external electric field is sufficient to cause electrophoretic motion of the fluorescent constructs within the combined composition. In some embodiments, the external electric field comprises, consists essentially of, or consists of a constant electric field which is applied in a constant direction.

In any of the preceding embodiments, the external electric field can comprise, consist essentially of, or consist of a pulsed electric field which is applied in a constant direction.

In any of the preceding embodiments, the external electric field can comprise, consist essentially of, or consist of: (i) an oscillating electric field which is applied in a constant direction; (ii) a constant electric field switching between multiple directions; (iii) a pulsed electric field switching between multiple directions; and/or (iv) an oscillating electric field switching between multiple directions.

In any of the preceding embodiments, the analyte can comprise a protein moiety and the analyte-interacting reagent can comprise a protein-binding agent such as an antibody.

In any of the preceding embodiments, the analyte can comprise a polynucleotide sequence and the analyte-interacting reagent can comprise a sequence capable of hybridizing to the polynucleotide sequence, such as a sequence complementary to the polynucleotide sequence. In some embodiments, the method further comprises melting and/or annealing the hybridized sequences, e.g., using a temperature control means of an analytic chamber and/or targeted local heating of quantum dots using focused light.

In any of the preceding embodiments, the method can comprise using a nutating transparent window and/or a rotating prism to move an image of each fluorescent construct across a surface of an optical detector.

In some aspects, disclosed herein is a method for formulating a set of aqueous droplets, comprising formulating each aqueous droplet suspended in a water-immiscible liquid matrix to contain a plurality of fluorescent constructs having a combination of fluorescence emission colors, fluorescent construct(s) of each fluorescence emission color having a count and each fluorescent construct having zero, one, or more reagents attached to it, wherein the identity of the reagent is specific to the color of its attached fluorescent construct and/or specific to the combination of colors and counts of the fluorescent constructs within each aqueous droplet. In some embodiments, the method further comprises collecting the set of aqueous droplets into a container.

In any of the preceding embodiments, the liquid matrix may be immiscible with water.

In any of the preceding embodiments, the liquid matrix may be selected from the group consisting of a lipid, an oil, a hydrocarbon fluid, a fluorocarbon fluid, a chlorocarbon fluid, a bromocarbon fluid, an iodocarbon fluid, a silicone fluid, and any suitable combination or mixture thereof.

In any of the preceding embodiments, the liquid matrix may be formulated as a gel.

In any of the preceding embodiments, the liquid matrix may glass at a low temperature.

In any of the preceding embodiments, the liquid matrix may solidify at a low temperature.

In any of the preceding embodiments, the liquid matrix may have a refractive index matching that of an aqueous droplet suspended or encapsulated in the liquid matrix.

In any of the preceding embodiments, the liquid matrix may have a refractive index higher or lower than that of an aqueous droplet suspended or encapsulated in the liquid matrix.

In any of the preceding embodiments, the liquid matrix may be non-Newtonian.

In any of the preceding embodiments, the liquid matrix may be shear-thinning.

In any of the preceding embodiments, the liquid matrix may be shear-thickening.

In any of the preceding embodiments, the liquid matrix may have a high viscosity.

In any of the preceding embodiments, the liquid matrix may have a low viscosity.

In any of the preceding embodiments, the liquid matrix may have a density matching that of an aqueous droplet suspended or encapsulated in the liquid matrix.

In any of the preceding embodiments, the liquid matrix may have a density less than that of an aqueous droplet suspended or encapsulated in the liquid matrix.

In any of the preceding embodiments, the liquid matrix may have a density greater than that of an aqueous droplet suspended or encapsulated in the liquid matrix.

In any of the preceding embodiments, the fluorescent constructs may be selected from the group consisting of quantum dots; fluorescent proteins; fluorescent molecules; polymeric particles that contain quantum dots, fluorescent proteins, or fluorescent molecules; fluorescent particles that are each linked through a system of chemical bonds to another fluorescent particle; and fluorescent particles that are each linked through a system of chemical bonds to a magnetic particle.

In any of the preceding embodiments, the fluorescent constructs may comprise one or more analyte-binding reagent bound to their surfaces.

In any of the preceding embodiments, the aqueous droplets may contain one or more magnetic particle.

In any of the preceding embodiments, the aqueous droplets may be stabilized with one or more surfactant.

In any of the preceding embodiments, the fluorescent constructs may be connected via a linkage to a fluorescent particle and/or a magnetic particle.

In any of the preceding embodiments, the set of aqueous droplets may contain disparate combinations of fluorescent construct emission colors and counts.

In some embodiments, disclosed herein is a method for formulating a set of gel beads, comprising formulating each gel bead in a gel matrix that can be removed by physical or chemical means, wherein each gel bead contains a plurality of fluorescent constructs having a combination of fluorescence emission colors, fluorescent construct(s) of each fluorescence emission color having a count and each fluorescent construct having zero, one, or more reagents attached to it, wherein the identity of the reagent is specific to the color of its attached fluorescent construct and/or specific to the combination of colors and counts of the fluorescent constructs within each gel bead. In some embodiments, the method further comprises collecting the set of gel beads into a container.

In any of the preceding embodiments, the fluorescent constructs can be selected from the group consisting of quantum dots; fluorescent proteins; fluorescent molecules; polymeric particles that contain quantum dots, fluorescent proteins, or fluorescent molecules; fluorescent particles that are each linked through a system of chemical bonds to another fluorescent particle; and fluorescent particles that are each linked through a system of chemical bonds to a magnetic particle.

In any of the preceding embodiments, the fluorescent constructs can comprise one or more analyte-binding reagent bound to their surfaces.

In any of the preceding embodiments, the gel beads can contain one or more magnetic particle.

In any of the preceding embodiments, the fluorescent constructs can be connected via a linkage to a fluorescent particle and/or a magnetic particle.

In any of the preceding embodiments, the set of gel beads can contain disparate combinations of fluorescent construct emission colors and counts.

In any of the preceding embodiments, the method can comprise melting the gel at an elevated temperature.

In any of the preceding embodiments, the method can comprise depolymerizing the gel by one or more enzyme.

In any of the preceding embodiments, the method can comprise depolymerizing the gel by one or more chemical agent.

In any of the preceding embodiments, the method can comprise depolymerizing the gel by light.

In any of the preceding embodiments, the set of gel beads can contain disparate combinations of fluorescent construct emission colors and counts.

In any of the preceding embodiments, the method can comprise applying a light to a composition comprising gel-forming monomers, a photocatalyst, and a plurality of fluorescent constructs, thereby selectively catalyzing polymerization of the gel-forming monomers in order to form a gel bead comprising a subset of the plurality of fluorescent constructs.

In some aspects, disclosed herein is a composition comprising the set of aqueous droplets and/or gel beads formulated by the method of any one of preceding embodiments In any of the preceding embodiments, each of the aqueous droplets may optionally contain an antifreeze, such as ethylene glycol or glycerin, e.g., to allow for cold storage.

In some embodiments, disclosed herein is a method for analyzing an analyte, comprising: contacting (i) a first composition comprising a first liquid matrix and a sample encapsulated in the first liquid matrix, with (ii) a second composition comprising a second liquid matrix and a formulation encapsulated in the second liquid matrix, wherein the formulation comprises a plurality of fluorescent constructs and an analyte-interacting reagent attached to one or more of the fluorescent constructs; and combining the sample with the formulation such that an analyte in the sample interacts with the analyte-interacting reagent attached to the one or more of the fluorescent constructs to generate a detectable signal, wherein the analyte is optionally located at the boundary between the first liquid matrix and the sample, wherein the detectable signal is analyzed for analyzing the presence or absence, an amount or concentration, and/or an activity of the analyte in the sample. In some embodiments, the first liquid matrix and the sample has the same or substantially the same refractive index.

In any of the preceding embodiments, the first liquid matrix and the second liquid matrix can be the same or different. In any of the preceding embodiments, the sample can be a solution and the analyte can be located at the boundary between the first liquid matrix and the sample. In any of the preceding embodiments, after combining the sample with the formulation, the sample and the formulation can remain encapsulated in the first and/or second liquid matrix.

In any of the preceding embodiments, the method can further comprise applying an excitation light to the plurality of fluorescent constructs and the detectable signal comprises fluorescence emission from the plurality of fluorescent constructs, wherein the excitation light comprises a simple ultraviolet light or a pulsed ultraviolet light. In any of the preceding embodiments, the method can further comprise analyzing diffusance of the plurality of fluorescent constructs, which analysis comprises analyzing the detectable signal. In any of the preceding embodiments, the method can further comprise analyzing a change in diffusance of the plurality of fluorescent constructs with increasing temperature and/or decreasing temperature. In any of the preceding embodiments, the change in diffusance can be analyzed to provide a melting temperature indicative of an interaction between the analyte and the analyte-interacting reagent.

In any of the preceding embodiments, the first composition can comprise a first oil and an aqueous sample encapsulated in the first oil, the second composition can comprise a second oil and an aqueous formulation encapsulated in the second oil. In any of the preceding embodiments, the aqueous formulation can comprise a plurality of quantum dots and an analyte-binding reagent attached to one or more of the quantum dots. In any of the preceding embodiments, the aqueous sample and the aqueous formulation can form a combined aqueous composition that remains encapsulated in oil, and the combined aqueous composition and its encapsulating oil may have the same or substantially the same refractive index.

In any of the preceding embodiments, the method can further comprise detecting a change in diffusance of the plurality of quantum dots encapsulated in oil with increasing temperature and/or decreasing temperature.

In some embodiments, disclosed herein is a method for analyzing a cell, comprising: contacting (i) a first composition comprising a first liquid matrix and a sample encapsulated in the first liquid matrix, wherein the sample comprises a single cell, with (ii) a second composition comprising a second liquid matrix and a formulation encapsulated in the second liquid matrix, wherein the formulation comprises a plurality of fluorescent constructs and an analyte-interacting reagent attached to one or more of the fluorescent constructs, wherein: (a) the single cell is lysed in the sample to released one or more cellular component or (b) the single cell in not lysed in the sample and a cell-lysing agent is optionally provided in the second composition; and combining the sample with the formulation such that a cellular component interacts with the analyte-interacting reagent attached to the one or more of the fluorescent constructs to generate a detectable signal, wherein the detectable signal is analyzed for analyzing the presence or absence, an amount or concentration, and/or an activity of the cellular component in the single cell. In some embodiments, the method comprises analyzing a plurality of single cells from a cell population, and comparing the presence or absence, amount or concentration, and/or activity of the cellular component in a first single cell to those of a second single cell to infer cell heterogeneity in the cell population.

In some embodiments, disclosed herein is a method for analyzing an analyte, comprising: contacting a first emulsion and a second emulsion with a sample, wherein: the first emulsion comprises a first formulation encapsulated in a first liquid matrix, wherein the first formulation comprises a first plurality of fluorescent constructs and a first reagent attached to one or more of the fluorescent constructs, and a first free agent; the second emulsion comprises a second formulation encapsulated in a second liquid matrix, wherein the second formulation comprises a second plurality of fluorescent constructs and a second reagent attached to one or more of the fluorescent constructs, and a second free agent; and the sample comprises an analyte, wherein the first and second reagents are capable of binding to the analyte; and demulsifying the first and second emulsions to allow the first and second plurality of fluorescent constructs and the first and second free agents to diffuse in the sample, wherein at least one of the first plurality of fluorescent constructs and/or at least one of the second plurality of fluorescent constructs are allowed to interact with the analyte in the presence of the first and second free agents to generate a detectable signal, wherein the detectable signal is analyzed for analyzing the presence or absence, an amount or concentration, and/or an activity of the analyte in the sample, and/or a first relationship between the first reagent and the second free agent with the analyte, and/or a second relationship between the second reagent and the first free agent with the analyte. In some embodiments, the first relationship is a synergistic binding effect between the first reagent and the second free agent with the analyte, and/or the second relationship is a synergistic binding effect between the second reagent and the first free agent with the analyte. In any of the preceding embodiments, the first relationship can be an allosteric binding effect between the first reagent and the second free agent with the analyte, and/or the second relationship can be an allosteric binding effect between the second reagent and the first free agent with the analyte.

In some embodiments, disclosed herein is a method for mapping interactions with a protein, comprising: contacting (i) a first composition comprising a first liquid matrix and a sample encapsulated in the first liquid matrix, wherein the sample comprises a protein, with (ii) a second composition comprising a second liquid matrix and a formulation encapsulated in the second liquid matrix, wherein the formulation comprises a plurality of fluorescent constructs and an analyte-interacting reagent attached to one or more of the fluorescent constructs; and combining the sample with the formulation such that the protein in the sample interacts with the analyte-interacting reagent attached to the one or more of the fluorescent constructs to generate a detectable signal, wherein the detectable signal is analyzed for analyzing an interaction between the analyte-interacting reagent and the protein. In some embodiments, the analyte-interacting reagent comprises a flexible linker to reduce or avoid steric hindrance for interacting with the protein, optionally wherein the analyte-interacting reagent comprises one or more dendrimer. In any of the preceding embodiments, the protein in the sample can interact with the analyte-interacting reagent in the presence of a weak gelling agent for controlling convection and/or slowing down diffusion. In any of the preceding embodiments, the method can be used for protein surface mapping.

In some embodiments, disclosed herein is a method of producing a population of emulsion droplets, comprising: mixing a population of first emulsion droplets each comprising one or more first fluorescent construct, a population of second emulsion droplets each comprising one or more second fluorescent construct, and a third emulsion droplet, in any suitable order, in a chamber comprising a liquid matrix which is immiscible with the first, second, and third emulsion droplets; combining the population of first emulsion droplets and the population of second emulsion droplets with the third emulsion droplet to form a combined emulsion droplet in the liquid matrix in the chamber, wherein the first and second fluorescent constructs are present in a defined ratio in the combined emulsion droplet; dividing the combined emulsion droplet into a population of fourth emulsion droplets, wherein at least 90% of the fourth emulsion droplets in the population comprise the first and second fluorescent constructs in the defined ratio, thereby producing the population of fourth emulsion droplets. In some embodiments, the first emulsion droplets, second emulsion droplets, and third emulsion droplet are aqueous droplets, wherein the aqueous droplets optionally comprises an antifreeze, such as ethylene glycol or glycerin.

In any of the preceding embodiments, the first and/or second fluorescent constructs can comprise quantum dots. In any of the preceding embodiments, the method can further comprise a step of mixing contents of the combined emulsion droplet. In any of the preceding embodiments, the first fluorescent constructs and the second fluorescent constructs can be evenly distributed within the combined emulsion droplet. In any of the preceding embodiments, the combining step can comprise demulsifying the first emulsion droplets, second emulsion droplets, and third emulsion droplet.

In any of the preceding embodiments, at least 95% of the fourth emulsion droplets in the population can comprise the first and second fluorescent constructs in the defined ratio. In any of the preceding embodiments, at least 99% of the fourth emulsion droplets in the population can comprise the first and second fluorescent constructs in the defined ratio. In any of the preceding embodiments, each of the fourth emulsion droplets in the population can comprise the first and second fluorescent constructs in the defined ratio.

In some embodiments, disclosed herein is a method for analyzing an analyte, comprising: contacting a first emulsion droplet, a second emulsion droplet, and a third emulsion droplet, wherein: the first emulsion droplet comprises a first formulation encapsulated in a first liquid matrix, wherein the first formulation comprises a first plurality of fluorescent constructs and a reagent attached to one or more of the fluorescent constructs; the second emulsion droplet comprises a second formulation encapsulated in a second liquid matrix, wherein the second formulation comprises a second plurality of fluorescent constructs, and free agent S; and the third emulsion droplet comprises a third formulation encapsulated in a third liquid matrix, wherein the third formulation comprises free agent R; and merging the first, second, and third emulsion droplets to allow the first and second plurality of fluorescent constructs and free agents S and R to diffuse in the merged emulsion droplet, wherein the reagent interacts with free agent R in the presence of free agent S to generate a detectable signal, wherein the detectable signal is indicative of an interaction among the reagent, free agent R, and free agent S. In some embodiments, the first, second, and/or third liquid matrices are the same. In any of the preceding embodiments, the first, second, and third formulations can be aqueous, the first and second pluralities of fluorescent constructs can be quantum dots, and the second plurality of fluorescent constructs may not interact with free agent S or R. In any of the preceding embodiments, free agent R can be a receptor for the reagent, and free agent S can be a synergetic molecule for the binding between R and the receptor. In any of the preceding embodiments, the merging can be controllable, e.g., by a laser pulse.

In some embodiments, disclosed herein is a composition comprising a first emulsion droplet, a second emulsion droplet, and a third emulsion droplet, wherein: the first emulsion droplet comprises a first formulation encapsulated in a first liquid matrix, wherein the first formulation comprises a first plurality of fluorescent constructs and a reagent attached to one or more of the fluorescent constructs; the second emulsion droplet comprises a second formulation encapsulated in a second liquid matrix, wherein the second formulation comprises a second plurality of fluorescent constructs, and free agent S; and the third emulsion droplet comprises a third formulation encapsulated in a third liquid matrix, wherein the third formulation comprises free agent R; wherein the reagent is capable of interacting with free agent R in the presence of free agent S to generate a detectable signal indicative of an interaction among the reagent, free agent R, and free agent S.

In any of the preceding embodiments, the second plurality of fluorescent constructs can be quantum dots each having an exceptionally thick or thin shell that reduces or enhances its diffusivity sufficient to allow discrimination from a quantum dot which is of the same color but has a reagent attached thereon.

In some embodiments, disclosed herein is a method for analyzing an analyte, comprising: contacting a first emulsion droplet, a second emulsion droplet, and a third emulsion droplet, wherein: the first emulsion droplet comprises a first formulation encapsulated in a first liquid matrix, wherein the first formulation comprises a first plurality of fluorescent constructs and a reagent attached to one or more of the fluorescent constructs; the second emulsion droplet comprises a second formulation encapsulated in a second liquid matrix, wherein the second formulation comprises one or more gel beads encapsulating a second plurality of fluorescent constructs, and free agent S; and the third emulsion droplet comprises a third formulation encapsulated in a third liquid matrix, wherein the third formulation comprises free agent R; and merging the first, second, and third emulsion droplets to allow the first plurality of fluorescent constructs, the one or more gel beads, and free agents S and R to diffuse in the merged emulsion droplet, wherein the second plurality of fluorescent constructs in each gel bead do not diffuse outside of the gel bead, wherein the reagent interacts with free agent R in the presence of free agent S to generate a detectable signal, and wherein the detectable signal is indicative of an interaction among the reagent, free agent R, and free agent S.

In some embodiments, disclosed herein is a composition, comprising a first emulsion droplet, a second emulsion droplet, and a third emulsion droplet, wherein: the first emulsion droplet comprises a first formulation encapsulated in a first liquid matrix, wherein the first formulation comprises a first plurality of fluorescent constructs and a reagent attached to one or more of the fluorescent constructs; the second emulsion droplet comprises a second formulation encapsulated in a second liquid matrix, wherein the second formulation comprises one or more gel beads encapsulating a second plurality of fluorescent constructs, and free agent S; and the third emulsion droplet comprises a third formulation encapsulated in a third liquid matrix, wherein the third formulation comprises free agent R, wherein the second plurality of fluorescent constructs in each gel bead do not diffuse outside of the gel bead, wherein the reagent is capable of interacting with free agent R in the presence of free agent S to generate a detectable signal indicative of an interaction among the reagent, free agent R, and free agent S.

In any of the preceding embodiments, the contacting step can further comprise contacting the first, second, and/or third emulsion droplet with a fourth emulsion droplet, wherein the fourth emulsion droplet comprises a fourth formulation encapsulated in a fourth liquid matrix, wherein the fourth formulation comprises a third plurality of fluorescent constructs and one or more gel beads encapsulating a fourth plurality of fluorescent constructs.

In any of the preceding embodiments, the contacting step can further comprise contacting the first, second, third, and/or fourth emulsion droplet with a fifth emulsion droplet, wherein the fifth emulsion droplet comprises a fifth formulation encapsulated in a fifth liquid matrix, wherein the fifth formulation comprises a fifth plurality of fluorescent constructs.

In any of the preceding embodiments, the first, second, third, fourth, and/or fifth liquid matrices can be the same. In any of the preceding embodiments, the first, second, third, fourth, and/or fifth formulations can be aqueous, the first, second, third, fourth, and/or fifth pluralities of fluorescent constructs can be quantum dots, and the gel beads may not interact with free agent S or R. In any of the preceding embodiments, free agent R can be a receptor for the reagent, and free agent S can be a synergetic molecule for the binding between R and the receptor. In any of the preceding embodiments, the merging can be controllable, e.g., by a laser pulse.

BRIEF DESCRIPTION OF THE DRAWINGS

In order that the present disclosure is better understood, methods in accordance with present disclosure will now be described, by way of example only, with reference to the accompanying drawings.

DETAILED DESCRIPTION

Figure 1:
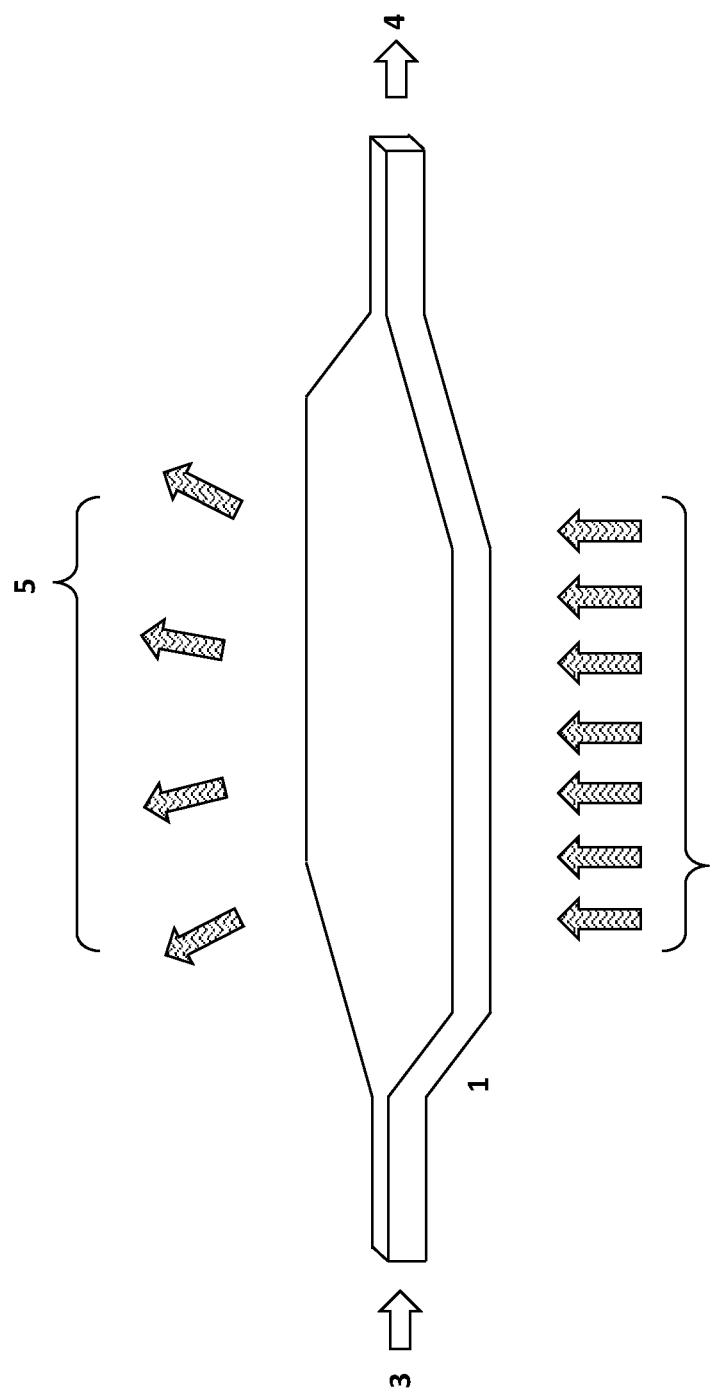
FIG. 1 is a schematic of an exemplary analytic chamber where aqueous sample is flowed through it and fluorescence excitation light is passed through it.

Selected embodiments of the present disclosure will be overviewed individually, and then methods in accordance with various embodiments of the present disclosure will be described. The embodiments and examples are intended to illustrate the present disclosure, and are not to be construed as limitations of the present disclosure.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

In some embodiments, provided herein are methods applicable to disease marker diagnostics, discovery of the disease markers, discovery of drug therapies, and/or evaluation of drug therapies. In one aspect, provided herein is a method for detection of an analyte interacting with an analyte binding reagent.

In some embodiments, the assays compositions and methods disclosed herein comprise the use of a heterogeneous assay format or a homogeneous assay format, or a combination of both assay formats at various steps. A heterogeneous assay format uses a fixed surface of analyte binding reagents exposed to a solvated sample, while a homogeneous assay format uses entirely solvated analyte binding reagents and sample.

Various aspects of the following exemplary assays may be included or excluded from the presently disclosed assay compositions and methods without departing from the true scope and spirit of the disclosure. Such embodiments with various aspects of the following exemplary assays included or excluded are intended to fall within the scope of the present disclosure.

One exemplary assay involves the use of electrodes, where analytes bind specifically to an electrode surface that has been derivatized with a reagent that binds to an analyte contained in a sample. This binding interaction alters the electron-transport behavior of the electrode in a manner that allows determination of the analyte presence or concentration.

A second exemplary assay is Enzyme Linked Immuno Sorbent Assay (ELISA). ELISA uses a fixed surface that is coated with an array of differing analyte binding reagents, which is typically exposed to a labeled sample for 30 to 120 minutes, rinsed, and then scanned for bound label. The labels can be fluorescent, radioactive, magnetic, or have some other detectable property. For fluorescent markers, rinsing can be avoided by having the fixed surface be transparent, and using an evanescent field, e.g., as described in Patent Application US2015/0010903A1.

A third exemplary assay is Surface Plasmon Resonance (SPR), such as that used by Biacore. SPR uses a fixed surface that is coated with an array of differing analyte binding reagents, exposed to a sample for several minutes, and then scanned for surface plasmon resonance. Total internal reflection from the array produces quantitative variations in the reflection angle, e.g., as described in U.S. Pat. Nos. 7,373,255, 7,262,866, 7,081,958, 7,012,694, 6,999,175, 6,775,003, 6,714,303, 6,589,798, 6,493,097, 6,127,183, 5,965,456, and 5,641,640.

A fourth exemplary assay is a homogeneous assay. These include agglutination assays and Fluorescence Resonance Energy Transfer (FRET) assays. Additionally, there is Differential Scanning Fluorimetry (DSF), such as that used by ThermaFluor. DSF uses a hydrophobic fluorescent dye that embeds within the hydrophobic center of a protein, which becomes exposed to the aqueous solvent as the temperature is raised and the protein molecule melts. This exposure unquenches the fluorescent dye. Reagents that bind to the protein affect the melting point, and thus the temperature at which fluorescence is unquenched. This provides an analytical signal for the binding interaction, e.g., as described in U.S. Pat. Nos. 6,214,293, 6,036,920, and 6,020,141.

A fifth exemplary assay involves the use of particles that are both fluorescent and magnetic, and can bind to analytes, e.g., as described in U.S. Pat. No. 9,658,219, where the particles are allowed to bind to analytes, are magnetically immobilized on a surface containing an evanescent wave, and are detected by optical attenuation or fluorescence.

A sixth exemplary assay involves the use of derivatized fluorescent quantum dots that can bind to particular analytes, e.g., as described in U.S. Pat. No. 9,664,667, where the quantum dots are allowed to bind to analytes, are placed near a surface containing an evanescent wave, and are detected individually by optical measurement. Brownian movement of each quantum dot causes it to move stochastically in and out of the evanescent field, at a certain diffusion rate. This movement produces corresponding variations in the fluorescence intensity of the particle. Optical tracking provides a measure of the diffusion rate of the quantum dot. The diffusion rate is affected by the binding interaction, where the binding interaction tends to increase the effective size of the quantum dot and reduce its diffusion rate. The combinatorial address space is constrained by the limited number of distinct colors of quantum dots. A larger address space may be attained by the use of heterogeneous structures composed of different quantum dots. Such heterogeneous structures are difficult to synthesize with a uniform composition and diffusivity, e.g., as described by Yu, Wan, et al. (2009). The fluorescence bands are broadened, the fluorescence quantum yield is reduced, and the larger size reduces sensitivity for measurements of binding interaction. Aside from the use of such heterogeneous structures, a description of how to enlarge the address space is not obvious. Also, a description of how to measure the transition in diffusivity during a binding interaction is not obvious. Lastly, a description of how to measure association and dissociation constants for the binding interaction is not obvious.

A seventh exemplary assay involves the use of aqueous emulsions to contain the sample and transport it to measurement apparatus, e.g., as described in Patent publication WO2002/068104 (including U.S. Pat. Nos. 7,268,167, 7,772,287, 7,717,615, and 7,375,140) and Patent publication WO2005/089921 (including U.S. Pat. No. 8,741,192) of the Japan Science and Technology Agency.

An eighth exemplary assay involves the use of aqueous emulsions to measure the effectiveness of antibiotics with synergistic compounds against a variety of bacteria, e.g., as described by Kulesa, Kehe, et al. (2018). Random pairs of droplets are contained within chambers, stimulated to merge using an electric field, and then each resulting merged droplet observed over time for the behavior of an entrapped bacterium. Droplets are labeled with a set of quantum dots, which allows identification of the antibiotics, compounds, and bacteria present in each droplet. This requires the use of a fixed array of chambers, each containing a random pair of droplets, in order to achieve a binary pairing of droplets. In contrast, the present disclosure avoids the requirement for a fixed array, and instead uses binary interactions without pair containment. This allows a simpler analytic chamber with a random array of droplets, e.g., as described in the Examples provided herein.

A ninth exemplary assay involves the use of confocal microscopy. This method uses point illumination and a pinhole in an optical conjugate plane. This eliminates out-of-focus light, providing higher resolution and greater accuracy when determining the location of small objects.

A tenth exemplary assay involves the use of Structured Illumination Microscopy (SIM). This method uses an interference pattern to generate a moiré pattern. The modulated image is mathematically deconvoluted to generate higher resolution and greater accuracy when determining the location of small objects.

An eleventh exemplary assay involves the use of STochastic Optical Reconstruction Microscopy (STORM). This method uses very low intensity illumination to stochastically activate fluorophores, allowing temporal separation of individual fluorophores. A set of images is combined to generate higher resolution and greater accuracy when determining the location of small objects.

A twelfth exemplary assay involves the use of Point-Scanning Two-Photon Microscopy. This method scans brief pulses of intense light across a sample, where the light has a wavelength longer than what is needed for fluorophore excitation. At high intensities, two photons may enter the fluorophore at the same time, doubling the effective energy and causing the fluorophore to fluoresce. This method enables high-resolution imaging within scattering samples.

A thirteenth exemplary assay involves the use of Scanned Line Angular Projection Microscopy (SLAPMi). This is a modification of Point-Scanning Two-Photon Microscopy, wherein focal lines of excitation are applied at multiple angles, analogous to Computed Tomography methods. This method allows very fast generation of images, while retaining high resolution within scattering samples, e.g., as described by Kazemipour, Novak, et al. and in WO2018208687A1.

A fourteenth exemplary assay involves the use of a fluorescence quenching agent for competitive protein binding. A set of quantum dots is generated with bromophenol blue bound to the surfaces, each color of quantum dot having a different binding strength to the bromophenol blue. The bromine atom of bromophenol blue produces a heavy atom effect that quenches the fluorescence of the associated quantum dot. Addition of sample protein will competitively adsorb the bromophenol blue molecules from a subpopulation of quantum dots. The freed quantum dots then have increased fluorescence. Linear Discriminate Analysis is then used to determine the binding strength of the sample protein, e.g., as described by Xu, Zhang, et al. (2016). Graphene may also be used for fluorescence quenching, e.g., as described by Chou, De, et al. (2012).

Methods that use sample oligonucleotides that have been labeled with a molecular fluorophore exist. In the present disclosure, no fluorophore is needed since diffusivity is the analytical signal. However, the sample oligonucleotides could be labeled with a heavy atom such as bromine, instead of a fluorophore. If the label is attached to the proximal end of the oligonucleotides, then it may act to partially quench the quantum dot fluorescence. This quenching would provide additional analytical data.

A fifteenth exemplary assay involves the use of phage display. A mixed population of phages with random mutations is generated, having random proteins externally expressed. This mixture is applied to a plate having an array of sample proteins affixed to it. Some phages will attach to the sample proteins. The excess phage is washed away, and the bound remainder is DNA sequenced. The DNA sequences encode proteins that will bind to the sample proteins.

A sixteenth exemplary assay is Suspension Array Technology (SAT). A mixed population of microsphere beads is generated, each containing a particular combination of quantum dot emission colors in particular intensity ratios, and coated with a particular reagent, such as an antigen or oligonucleotide. When fluorescence excitation light is applied, the pattern of fluorescence emission colors and amplitudes provides identification of each bead, and thereby the identification of its reagent coating. When incubated with a sample, particular sample molecules bind to particular bead-bound reagents; subsequent washing and incubation steps with fluorescent molecules produces a molecular sandwich, and the bead population is characterized by flow cytometry, which identifies the bead-bound reagent by the quantum dot fluorescence and the occurrence of binding by fluorescent molecule fluorescence. This method is used commercially by Bio-Rad, Inc. and other companies, and is called Luminex xMAP Technology and Bio-Plex Technology.

In one aspect, provided herein is a method for detection of an analyte interacting with an analyte binding reagent, comprising: (a) providing a first liquid, wherein the first liquid comprises a portion of a sample, for example, a biological sample may be mixed and/or diluted with a buffer to form the first liquid; (b) providing an emulsion formed between (i) a liquid droplet comprising a second liquid and (ii) a liquid matrix, wherein the liquid droplet comprises a plurality of fluorescent constructs having an analyte binding reagent attached to all or a set of the fluorescent constructs.

In some embodiments, the first and second liquids are both aqueous, and the liquid droplet is an aqueous droplet. In some embodiments, the method further comprises contacting the first liquid with the aqueous droplet to form a combination of the first liquid and the second liquid under conditions that allow the first liquid and the second liquid to merge into a single fluid. In some embodiments, the method further comprises detecting a signal generated by a binding interaction of the analyte with the analyte binding reagent that provides an indication of the presence or absence, an amount or concentration, and/or a property or activity (e.g., a binding activity) of the analyte. In any of the preceding embodiments, the emulsion comprises a plurality of liquid droplets in the liquid matrix.

Methods for forming mixed droplets and microfluidic droplet generation and manipulation are known, see, e.g., U.S. Pat. No. 9,364,803 and US 2019/0060861, and may be used in connection with one or more embodiments disclosed herein.

Figure 20:
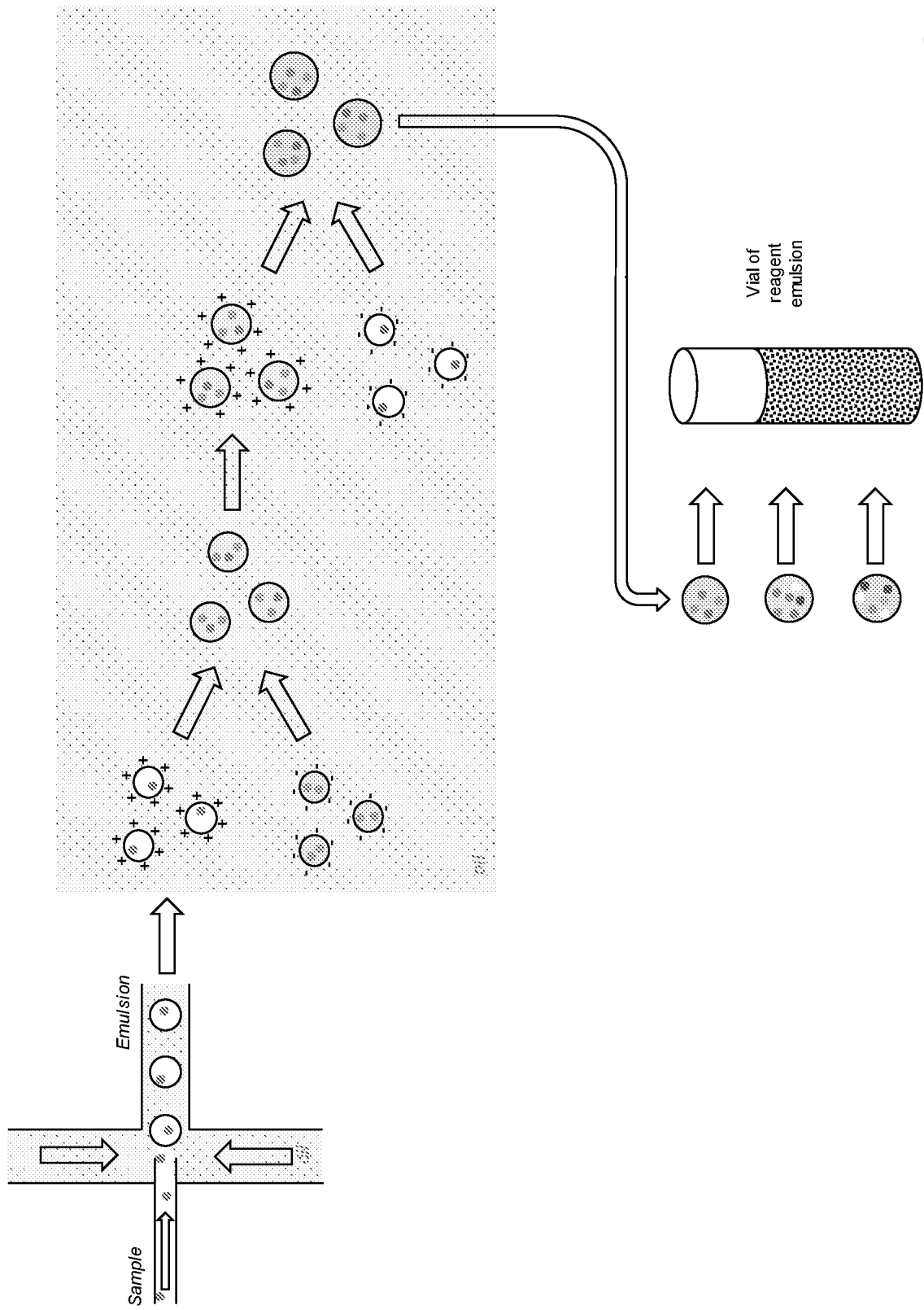
FIG. 20 shows an exemplary method for reagent emulsion synthesis, utilizing binary emulsion merging for customized emulsion droplet compositions.

Methods for controlled merging of emulsion droplets and sample analysis are described in U.S. Provisional Application No. 62/768,743, filed Nov. 16, 2018, entitled "Methods for the Detection of Analyte Concentrations and Binding Interactions," U.S. Provisional Application No. 62/768,754, filed Nov. 16, 2018, entitled "Methods for Controlled Merging of Emulsion Droplets," and U.S. Ser. No. 16/685,376, filed Nov. 15, 2019, entitled "Compositions and Methods for Controllably Merging Emulsion Droplets and Sample Analysis," the contents of which applications are herein incorporated by reference in their entireties for all purposes. FIG. 20 shows an exemplary method for reagent emulsion synthesis, utilizing binary emulsion merging for customized emulsion droplet compositions. Each originating droplet may contain a specific reagent, or may contain a single cell, e.g., a cell that has been lysed or is to be lysed. In some embodiments, binary emulsion droplets are provided and contain two different dyes such as fluorescent dyes.

In some embodiments, emulsion droplets containing various combinations of quantum dots, fluorescent dyes, and/or reagents are produced using a method comprising controlled merging of emulsion droplets. In some embodiments, binary emulsion droplets are assembled using differential electrostatic charging and/or differential surfactants. In some embodiments, the method comprises contacting (i) a first emulsion comprising a first aqueous droplet in a first liquid matrix, with (ii) a second emulsion comprising a second aqueous droplet in a second liquid matrix, under conditions that allow the first aqueous droplet to merge with the second aqueous droplet to form a merged droplet, wherein the merging is controlled and is provided by: (i) the first aqueous droplet comprising a first redox species and the first liquid matrix comprising a first electrolyte, the second aqueous droplet comprising a second redox species and the second liquid matrix comprising a second electrolyte, wherein the first and second aqueous droplets are each contacted with an electrode to cause charge transfer between the aqueous droplet and the electrode; (ii) the first emulsion stabilized with a first charged surfactant, and the second emulsion stabilized with a second charged surfactant of opposite charge from that of the first charged surfactant; (iii) contacting the first emulsion with a positive electrode sufficient to cause electrostatic charging of the first aqueous droplet, and contacting the second emulsion with a negative electrode sufficient to cause electrostatic charging of the second aqueous droplet; and/or (iv) the first aqueous droplet comprising a first magnetic particle, the second aqueous droplet comprising a second magnetic particle, wherein an external magnetic field is applied to produce an attractive force between said first magnetic particle and said second magnetic particle.

In some embodiments, provided herein is a method to electrostatically charge a droplet, e.g., to produce a negatively charged or positively charged droplet for merging with a droplet of the opposite charge, e.g., as shown in FIG. 20. In some embodiments, a tube or channel with an inner diameter or size that is about the same as that of a droplet is used. For instance, the emulsion may be flowed through the tube or channel. In some embodiments, the tube or channel is (or contains) a hydrophobic conductor that is electrically charged, and the charge may be transferred to the droplets that pass through, without damaging the droplets. With two such (oppositely) charged channels, the streams of emulsion droplets are immediately fed into a nonconductive Y-shaped device, allowing the oppositely-charged droplets to coalesce as binary pairs. Electrostatic adherence to the conductor may occur due ionic attractions being greater than electrostatic repulsion. In some embodiments, a gelling agent is added to the oil matrix, and the two oppositely charged channels are chilled to gel the oil matrix, in order to help push the droplets off of the conductive electrodes, followed by warming at the Y. Oil can be gelled by using reagents such as polyisobutene and polydimethylsiloxane.

Figure 21:
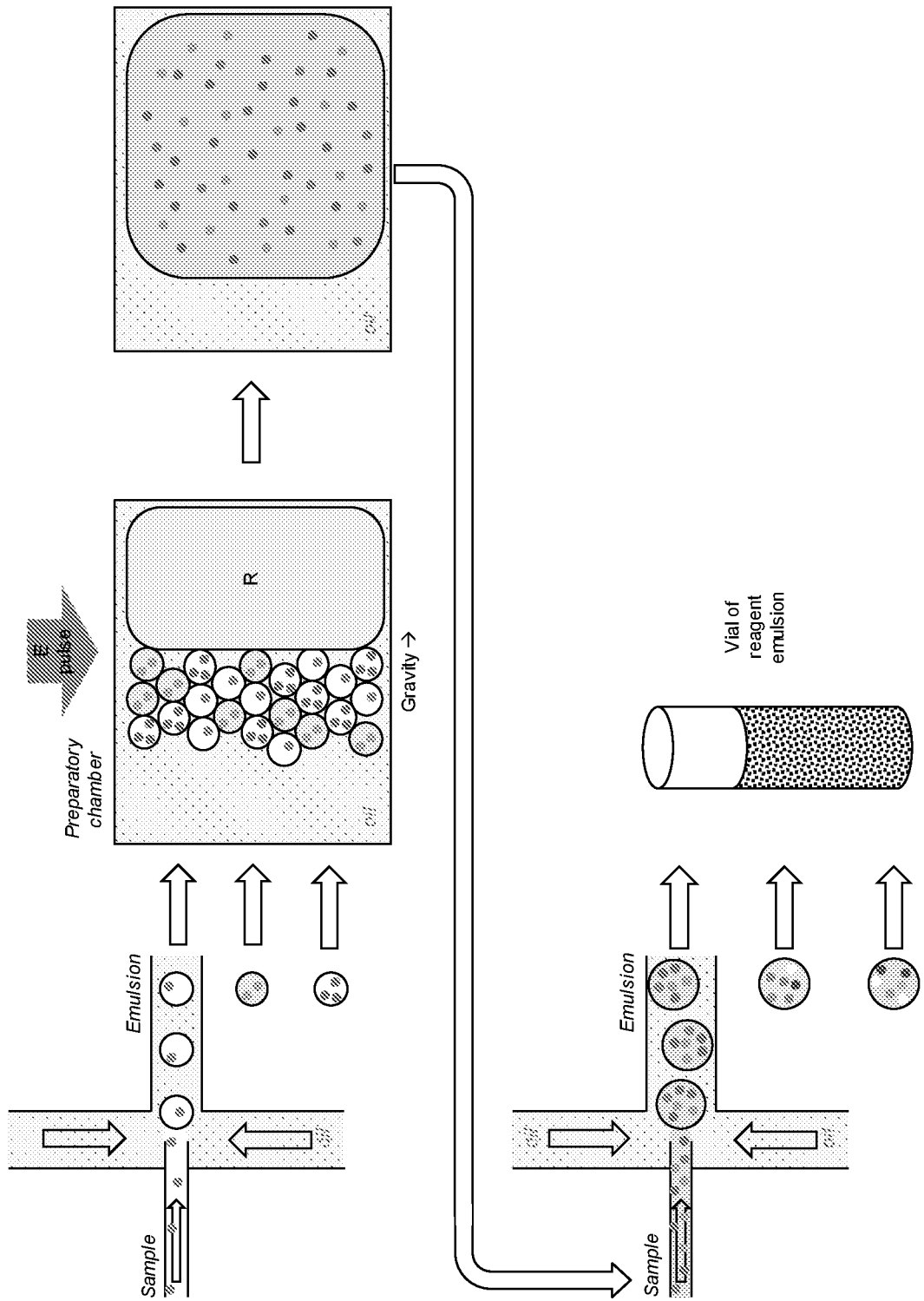
FIG. 21 shows an exemplary method for the preparation of reagent emulsion in bulk, using an exemplary chamber disclosed herein as a preparatory chamber.

Also provided herein is a method of producing a population of emulsion droplets, comprising: mixing a population of first emulsion droplets each comprising one or more first fluorescent construct, a population of second emulsion droplets each comprising one or more second fluorescent construct, and a third emulsion droplet (e.g., a large droplet comprising reagent R as shown in FIG. 21), in any suitable order, in a chamber comprising a liquid matrix which is immiscible with the first, second, and third emulsion droplets; combining the population of first emulsion droplets and the population of second emulsion droplets with the third emulsion droplet to form a combined emulsion droplet in the liquid matrix in the chamber, wherein the first and second fluorescent constructs are present in a defined ratio in the combined emulsion droplet; dividing the combined emulsion droplet into a population of fourth emulsion droplets, wherein at least 90% of the fourth emulsion droplets in the population comprise the first and second fluorescent constructs in the defined ratio, thereby producing the population of fourth emulsion droplets. A weak electric pulse may be used to break up the emulsions in the chamber and combine the first emulsion droplets, the second emulsion droplets, and the third emulsion droplet. The contents of the combined emulsion droplet may be mixed, such that the first and/or second fluorescent constructs, e.g., quantum dots may be evenly distributed in the combined emulsion droplet. Statistically, substantially all of the fourth emulsion droplets produced from the combined emulsion droplet contain the first and second fluorescent constructs in the defined ratio. In some embodiments, at least 99% of the fourth emulsion droplets in the population comprise the first and second fluorescent constructs in the defined ratio.

In some embodiments, provided herein is a method for detection of an analyte interacting with an analyte binding reagent, comprising contacting (i) a first liquid that comprises a portion of a sample, with (ii) an emulsion formed between a liquid droplet comprising a second liquid and a liquid matrix, wherein the liquid droplet comprises a plurality of fluorescent constructs having an analyte binding reagent attached to all or a set of the fluorescent constructs. In some embodiments, the first and second liquids are both aqueous, and the liquid droplet is an aqueous droplet. In some embodiments, the method further comprises forming a combination of the first liquid and the second liquid under conditions that allow the first liquid and the second liquid to merge into a single fluid. For instance, the method may comprise breaking the emulsion to allow the liquid droplet to merge into the first liquid. In some embodiments, the emulsion comprises a plurality of liquid droplets suspended or encapsulated in the liquid matrix. In some embodiments, the method further comprises detecting a signal generated by a binding interaction of the analyte with the analyte binding reagent that provides an indication of the presence or absence, an amount or concentration, and/or a property or activity (e.g., a binding activity) of the analyte.

In some embodiments, provided herein is a method for detection of an analyte interacting with an analyte binding reagent, comprising: (a) providing a first liquid comprising an analyte; (b) providing an emulsion formed between (i) a reagent droplet comprising a second liquid and (ii) a water-immiscible host matrix, wherein the reagent droplet comprises a plurality of fluorescent constructs having an analyte binding reagent attached to all or a set of the fluorescent constructs; (c) mixing the first liquid and the reagent droplet together in an analytic chamber and allowing the first liquid and the reagent droplet to merge into a single fluid; (d) directing an excitation light of a controlled phase through said analytic chamber after said mixing sufficient to cause fluorescence of one or more of the fluorescent constructs, wherein said fluorescence is dependent on fluorescent construct position within a local phase angle of the excitation light; and (e) detecting a fluorescence emission and/or measuring the magnitude of the fluorescence emission after said mixing step. In some embodiments, the method further comprises determining the identity of each analyte binding reagent present within each reagent droplet from the pattern of fluorescent emission wavelengths, e.g., in the vicinity of the position where each droplet has merged with the first liquid. In some embodiments, a change in the stochastic behavior of the magnitude of the fluorescence emission provides an indication of the presence or absence, an amount or concentration, and/or a property or activity (e.g., a binding activity) of the analyte.

In some embodiments, provided herein is a method for detection of an analyte interacting with an analyte binding reagent, comprising contacting, in an analytic chamber, a first liquid comprising an analyte with an emulsion formed between (i) a reagent droplet comprising a second liquid and (ii) a water-immiscible host matrix, wherein the reagent droplet comprises a plurality of fluorescent constructs having an analyte binding reagent attached to all or a set of the fluorescent constructs. In some embodiments, the method further comprises allowing the first liquid and the reagent droplet to merge into a single fluid. For instance, the method may comprise breaking the emulsion to allow the reagent droplet to merge into the first liquid. In some embodiments, the method further comprises directing an excitation light of a controlled phase through said analytic chamber after said mixing sufficient to cause fluorescence of one or more of the fluorescent constructs, wherein said fluorescence is dependent on fluorescent construct position within a local phase angle of the excitation light. In some embodiments, the method further comprises detecting a fluorescence emission and/or measuring the magnitude of the fluorescence emission after said mixing step. In some embodiments, the method further comprises determining the identity of each analyte binding reagent present within each reagent droplet from the pattern of fluorescent emission wavelengths, e.g., in the vicinity of the position where each droplet has merged with the first liquid. In some embodiments, a change in the stochastic behavior of the magnitude of the fluorescence emission provides an indication of the presence or absence, an amount or concentration, and/or a property or activity (e.g., a binding activity) of the analyte.

In some embodiments, provided herein is a method for detection of an interaction between an analyte in a sample and an analyte binding reagent, wherein the method comprises: (a) providing a first liquid comprising an analyte; (b) providing an emulsion formed between (i) a reagent droplet comprising a second liquid and (ii) a water-immiscible host matrix, wherein the reagent droplet comprises a plurality of fluorescent constructs having an analyte binding reagent attached to all or a set of the fluorescent constructs; (c) mixing the first liquid and the reagent droplet together in an analytic chamber and allowing the first liquid and the reagent droplet to merge into a single fluid; (d) directing a controlled spatial pattern of excitation light through said analytic chamber after said mixing sufficient to cause fluorescence of one or more of the fluorescent constructs, wherein said fluorescence is dependent on fluorescent construct position within a local spatial pattern of the excitation light; and (e) detecting a fluorescence emission and/or measuring the magnitude of the fluorescence emission after said mixing step. In some embodiments, the method further comprises determining the identity of each analyte binding reagent present within each reagent droplet from the pattern of fluorescent emission wavelengths, e.g., in the vicinity of the position where each droplet has merged with the first liquid. In some embodiments, a change in the stochastic behavior of the magnitude of the fluorescence emission provides an indication of the presence or absence, an amount or concentration, and/or a property or activity (e.g., a binding activity) of the analyte.

In some embodiments, provided herein is a method for detection of an analyte interacting with an analyte binding reagent, comprising contacting, in an analytic chamber, a first liquid comprising an analyte with an emulsion formed between (i) a reagent droplet comprising a second liquid and (ii) a water-immiscible host matrix, wherein the reagent droplet comprises a plurality of fluorescent constructs having an analyte binding reagent attached to all or a set of the fluorescent constructs. In some embodiments, the method further comprises allowing the first liquid and the reagent droplet to merge into a single fluid. For instance, the method may comprise breaking the emulsion to allow the reagent droplet to merge into the first liquid. In some embodiments, the method further comprises directing a controlled spatial pattern of excitation light through said analytic chamber after said mixing sufficient to cause fluorescence of one or more of the fluorescent constructs, wherein said fluorescence is dependent on fluorescent construct position within a local spatial pattern of the excitation light. In some embodiments, the method further comprises detecting a fluorescence emission and/or measuring the magnitude of the fluorescence emission after said mixing step. In some embodiments, the method further comprises determining the identity of each analyte binding reagent present within each reagent droplet from the pattern of fluorescent emission wavelengths, e.g., in the vicinity of the position where each droplet has merged with the first liquid. In some embodiments, a change in the stochastic behavior of the magnitude of the fluorescence emission provides an indication of the presence or absence, an amount or concentration, and/or a property or activity (e.g., a binding activity) of the analyte.

In some aspects, the method disclosed herein uses a sample liquid containing one or more analyte that is mixed with an emulsion of aqueous reagent droplets. For example, each aqueous reagent droplet may comprise one or more analyte binding reagent. In some aspects, the sample liquid contains the analyte or analytes to be analyzed by a method disclosed herein. The sample liquid may be in the form of an emulsified droplet. In some aspects, the reagent droplets each contain one or more fluorescent constructs, such as a fluorophore or a particle containing a fluorophore. In some embodiments, one or more of the fluorescent constructs comprise a reagent capable of binding to the analyte or analytes. In some embodiments, the reagent is attached to a surface of the one or more fluorescent constructs. For example, the reagent may be covalently or non-covalently attached to the surface, and the reagent may be directly attached to the surface or indirectly attached to the surface, e.g., via a linker.

In some aspects, after contacting the sample liquid with the reagent droplets within an analytic chamber, the sample liquid and the liquids within the reagent droplets may be combined, e.g., merged into one homogeneous liquid. In some embodiments, upon combination of the liquids, the fluorescent constructs containing one or more analyte-interacting (e.g., analyte-binding) reagent are allowed to interact with the analyte(s), for example, a binding interaction may occur. In some aspects, an excitation light is applied to illuminate the liquid mixture, producing fluorescence emission which is continuously monitored and tracked for each fluorescent construct. In some aspects, fluorescence emission is continuously monitored and tracked for all fluorescent constructs from the same reagent droplet.

In some embodiments, the phase or spatial pattern of the excitation light is controlled such that electric and magnetic field vectors of the excitation light are not uniform across the analytic chamber. As Brownian motion moves a fluorescent construct (such as a fluorescent particle, e.g., a quantum dot) within the mixed liquid, its fluorescence will vary with the magnitude of the local electric field vector and magnetic field vector. In some aspects, the movement is affected by a binding interaction with an analyte, and hence affects the stochastic behavior of the magnitude of the fluorescence emission. In some aspects, the transition in the stochastic behavior of the magnitude of the fluorescence emission after mixing constitutes a measurement of the analyte, e.g., the presence or absence, an amount or concentration, and/or a property or activity (e.g., a binding activity) of the analyte.

In some embodiments, the identity of the reagent is determined by the pattern of fluorescence wavelengths associated with each droplet. In some embodiments, after mixing, the fluorescent constructs within a droplet begin to diffuse outward through the sample liquid. In some aspects, this outward diffusion forms a slowing enlarging local constellation of fluorescent constructs, such as quantum dots. In some aspects, the enlarging constellation of fluorescent constructs spreads out and allows detection of individual fluorescent constructs. In some aspects, the population of fluorescent constructs within a droplet is large enough to allow unique identification of individual droplet and thus its associated reagent or reagents. In some aspects, the population of fluorescent particles within a droplet allows the fluorescent constructs to be individually distinguished by an optical system or detection algorithm.

In some embodiments, disclosed herein is a method for analyzing an analyte, e.g., for detecting the presence or absence, an amount, and/or an activity of an analyte in a sample. In some embodiments, the method comprises contacting (i) a first composition comprising a liquid phase and a sample in the liquid phase, with (ii) a second composition comprising a liquid matrix and a formulation encapsulated in the liquid matrix, wherein the formulation comprises a plurality of fluorescent constructs and an analyte-interacting reagent attached to one or more of the fluorescent constructs. In some embodiments, the method further comprises combining the liquid phase and the formulation, e.g., under conditions that allow the liquid phase and the formulation to merge into a single fluid. In some embodiments, the method further comprises allowing an analyte in the sample to interact with the analyte-interacting reagent attached to the one or more of the fluorescent constructs. In some embodiments, an interaction between the analyte in the sample and the analyte-interacting reagent generates a detectable signal. In some embodiments, the detectable signal is analyzed, e.g., for detecting the presence or absence, an amount, and/or an activity of the analyte in the sample.

The section headings used herein are for organizational purposes only and are not to be construed as limiting the subject matter described.

I. Methods for Analyzing a Sample Based on Diffusion of Reagents

In some embodiments, an aqueous sample to be analyzed is contacted with an emulsion, wherein the emulsion is formed of droplets of water containing fluorescent particles that may bind to one or more analyte in the sample. In some embodiments, the contacting occurs in an analytic chamber. Inside the analytic chamber, the emulsion droplets and the aqueous sample are merged, allowing the fluorescent particles to bind to one or more analyte in the sample. In some embodiments, fluorescence excitation light is applied to the merged mixture. Characteristics of the fluorescence emission are measured, e.g., to provide readouts for the concentration and/or binding interaction for the one or more analyte, which can provide useful information about biological samples, such as liquid biopsy samples for cancer detection for a patient.

In some embodiments, an aqueous sample is mixed with a plurality of reagent droplets in an analytic chamber. The aqueous sample may contain analytes to be analyzed. The reagent droplets may each contain one or more fluorescent particle, at least one of which is attached to a reagent capable of interacting with one or more analyte in the sample. For example, the one or more fluorescent particle may each have a surface coated with one or more analyte-binding reagent.

In some embodiments, the aqueous sample may be present in the form of a sample droplet in an immiscible matrix. In some embodiments, the surface of the sample droplet comprises or is treated with a surfactant. In some embodiments, the reagent droplet is or comprises an emulsion within a water-immiscible host matrix, or a gel bead within an aqueous matrix. In some embodiments, the reagent droplet surfaces may be stabilized with a surfactant. When surfactants are used for both the aqueous sample and the reagent droplets, in some embodiments, the two surfactants may be of the same charge, opposing charge, or no charge.

In some embodiments, the surfactant is or comprises an amphiphilic molecule containing a polar, hydrophilic group and a nonpolar, hydrophobic group. The polar, hydrophilic group can be either positively charged by a cation moiety, negatively charged by an anion moiety, nonionic, or amphoteric. Examples of cationic surfactants include benzalkonium chloride, benzethonium chloride, cetrimonium bromide, stearalkonium chloride, tetramethylammonium hydroxide, and thonzonium bromide. Examples of anionic surfactants include sodium alkyl sulfates, alkylbenzene sulfonates, chlorosulfolipids, perfluoroalkyl sulfonic acids, phospholipids, and sulfolipids. Examples of nonionic surfactants include alkyl polyglycosides, alkyl glucosides, cetyl alcohol, glycerol monostearate, maltosides, nonoxynols, polysorbates, and sorbitan stearates. Examples of amphoteric surfactants include imino propionates, imino acetates, lauryl betaine, betaine citrate, sodium hydroxymethylglycinate, sodium lauroamphoacetate, and (carboxymethyl)dimethyloleylammonium hydroxide. Amphoteric surfactants are also known as zwitterionic surfactants.

In some embodiments, an emulsion is stabilized by one or more surfactant because their droplets have a like surface charge that repels other droplets, minimizing coalescence of the droplets. In some embodiments, the surfactants self-assemble onto the surface of each droplet such that the polar, hydrophilic group of the surfactant molecule is toward the droplet, and the nonpolar, hydrophobic group of the surfactant molecule is away from the reagent droplet.

In some embodiments, the aqueous sample surface or the reagent droplet surfaces are populated with proteins that can occur as membrane proteins in cells. Such proteins have a hydrophobic component that extends into the phospholipid bilayer of cell membranes. In some embodiments, such proteins are considered to be surfactants.

In some embodiments, the reagent droplets of the emulsion are suspended in a host matrix. In some embodiments, the host matrix of each emulsion is a liquid or liquid crystal that is water-immiscible. Examples of host matrices are lipids, oils, hydrocarbon fluids, fluorocarbon fluids, chlorocarbon fluids, bromocarbon fluids, iodocarbon fluids, silicone fluids, and their mixtures. Commercially available fluorocarbon fluids include Fluorinert FC-40, Fluorinert FC-43, Fluorinert FC-70, Fluorinert FC-75, Fluorinert FC-3283, and perfluorodecalin. In some embodiments, the host matrix is chosen such that its refractive index is close to that of the aqueous sample, so that optical distortions in the analytic chamber are minimized. In some embodiments, the host matrix is chosen such that it forms a gel or glass at low temperatures, to enhance storage stability over long time periods.

In some embodiments, the density of the reagent droplets relative to its host matrix imposes a gravitationally-driven movement of the droplets, e.g., floating upwards or sinking downwards, which tends to compact the droplets together and lessens emulsion stability. In some embodiments, the gravitationally-driven movement is mitigated by Brownian motion, such that emulsion stability is improved. In some embodiments, the method disclosed herein comprises promoting Brownian motion of the reagent droplets in order to mitigate the gravitationally-driven movement of the reagent droplets.

In some embodiments, the emulsion is formed using known methods by combining a slow flow of aqueous composition (e.g., aqueous media) with a fast flow of water-immiscible composition (e.g., a water-immiscible medium) within a flow cell. In some embodiments, this method generates aqueous droplets having a highly uniform size within a water-immiscible host matrix. Secondary emulsions that are composed of a water-immiscible droplet within an aqueous droplet that is itself within a water-immiscible host matrix can also be formed. Such emulsion methods are performed commercially, such as by the Japan Science and Technology Agency. Production of equivalent gel beads is performed commercially, such as by the Luminex Corp for their xTAG and MagPlex microspheres.

In some embodiments, the aqueous composition contains a plurality of fluorescent particles, such that the resulting aqueous droplets contain the fluorescent particles. In some embodiments, the concentration of the fluorescent particles in the aqueous composition is set such that statistically there is a small population of fluorescent particles per aqueous droplet, with an approximately known count of fluorescent particles. In some embodiments, fluorescence-based sorting of the resulting droplets may be implemented to yield a population of droplets containing a more controlled population of fluorescent particles. The internal water-immiscible droplet of a secondary emulsion may also contain fluorescent particles.

In some embodiments, the aqueous composition contains a mixture of fluorescent particles having a known set of fluorescence emission spectrums (e.g., colors), each fluorescent particle with a known concentration in the aqueous composition. The resulting droplets may be collected into a resulting emulsion.

In some embodiments, the aqueous composition contains fluorescent particles having a known single fluorescence emission spectrum (e.g., color) with a known concentration. In some embodiments, a number of such aqueous compositions are used to produce separate emulsions. Then, two or more separate emulsions can be merged, e.g., a single droplet from each separate emulsion may be merged into a larger droplet. The larger droplets may be collected into a resulting emulsion.

In some embodiments, the population of fluorescent constructs (e.g., particles) in each droplet of the resulting emulsion comprises a combination of different emission wavelengths with different counts of fluorescent constructs. For example, droplets may be made, each having approximately 6 fluorescent particles emitting red light, 9 fluorescent particles emitting green light, and 3 fluorescent particles emitting blue light. In some embodiments, the disparate particle population uniquely labels the droplet, and collectively, the combination of the different emission wavelengths and different counts of fluorescent constructs provide a large address space.

In some embodiments, the population of fluorescent constructs (e.g., particles) in each droplet is large enough to ensure a statistically consistent number of fluorescent particles in each droplet during manufacture, but small enough to allow an optical detection system to distinguish the individual fluorescent constructs (e.g., particles). Examples of fluorescent constructs (e.g., particles) include quantum dots, carbon dots, green fluorescent protein (GFP) molecules, fluorescein molecules, the commercial dye Alexa Fluor 405, and the commercial dye Alexa Fluor 647.

In some embodiments, the fluorescent constructs are quantum dots, which typically have a semiconductor core surrounded by a protective layer and are typically about 5 nm in diameter. In some embodiments, a layer of reagents that can bind to an analyte is immobilized on the outer surface of one or more quantum dot. Typical protein analytes have a size range from 10 nm to 50 nm in diameter. Therefore, typically the attachment of a protein analyte to the fluorescent construct (e.g., a particle such as a quantum dot) produces a large change in the hydrodynamic properties of the fluorescent construct.

In some embodiments, fluorescent particles with a bola structure are synthesized and used herein. These fluorescent particles typically comprise two fluorescent particles connected by a flexible linkage (e.g., homogenous bola), or by a fluorescent particle and a magnetic particle connected by a flexible linkage (e.g., heterogeneous bola). An example of the use of such a bola structure is for Fluorescence Resonant Energy Transfer (FRET) analysis. In some embodiments, a flexible linkage is used, and the flexible linkage exhibits a binding interaction with nucleic acids in the aqueous sample, where the binding interaction affects the flexibility of the linkage and thereby affecting the mobility of the fluorescent particles. In some embodiments, a magnetic field with a heterogeneous bola is used to control movement of the fluorescent particle in the heterogeneous bola, such as by dragging the fluorescent particle around in a circular motion, in and out of the path of fluorescence excitation light. Other types of fluorescent constructs, such as fluorescent proteins, fluorescent molecules, and polymeric spheres that contain quantum dots, fluorescent proteins, fluorescent molecules, and a combination thereof, may be used in the method or composition disclosed herein.

Collectively, the excitation spectrum of quantum dots is quite broad, meaning that one excitation light can be used to excite a wide variety of quantum dots, thereby producing fluorescence of different colors. Typically, ultraviolet light is used for quantum dot excitation. Without being bound to any particular theory, excitation of a fluorescent construct may be produced from the electric field vector of the excitation light.

Figure 18:
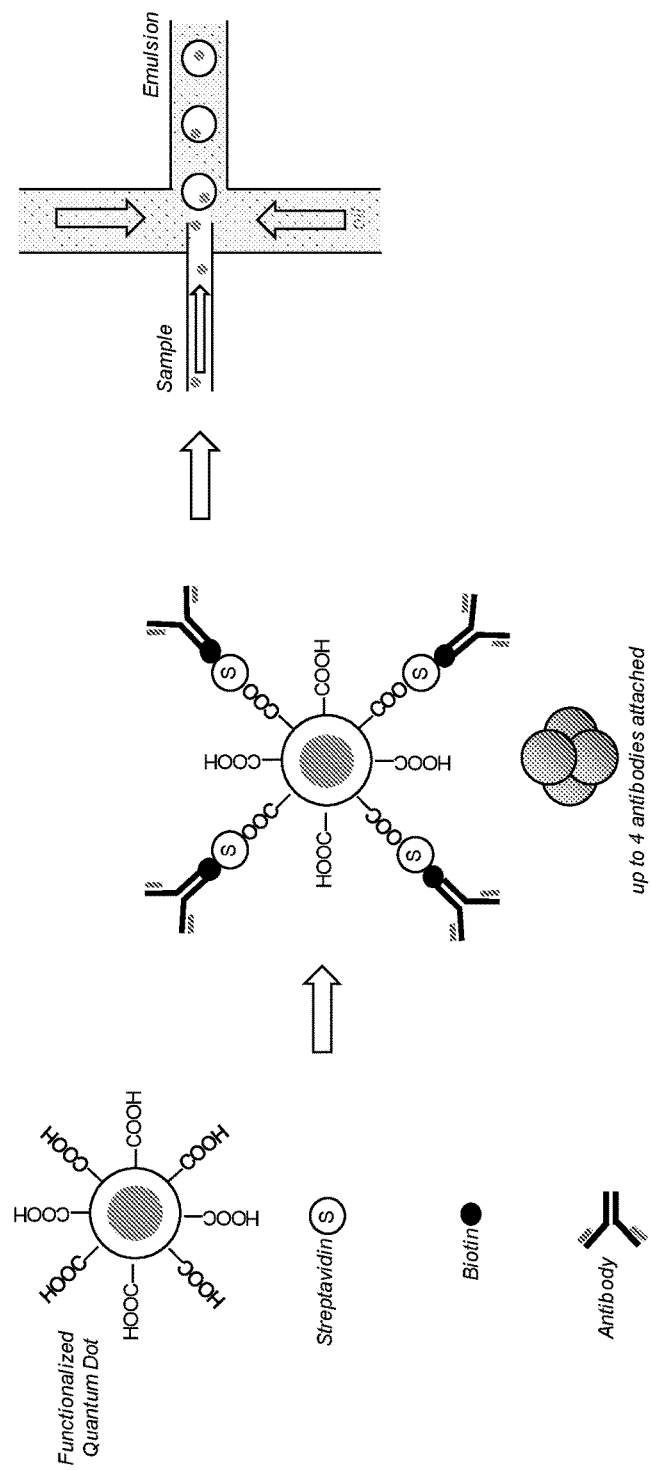
FIG. 18 shows exemplary quantum dots that may be functionalized, e.g., with antibodies, and an exemplary method of creating emulsion droplets containing quantum dots.
Figure 19:
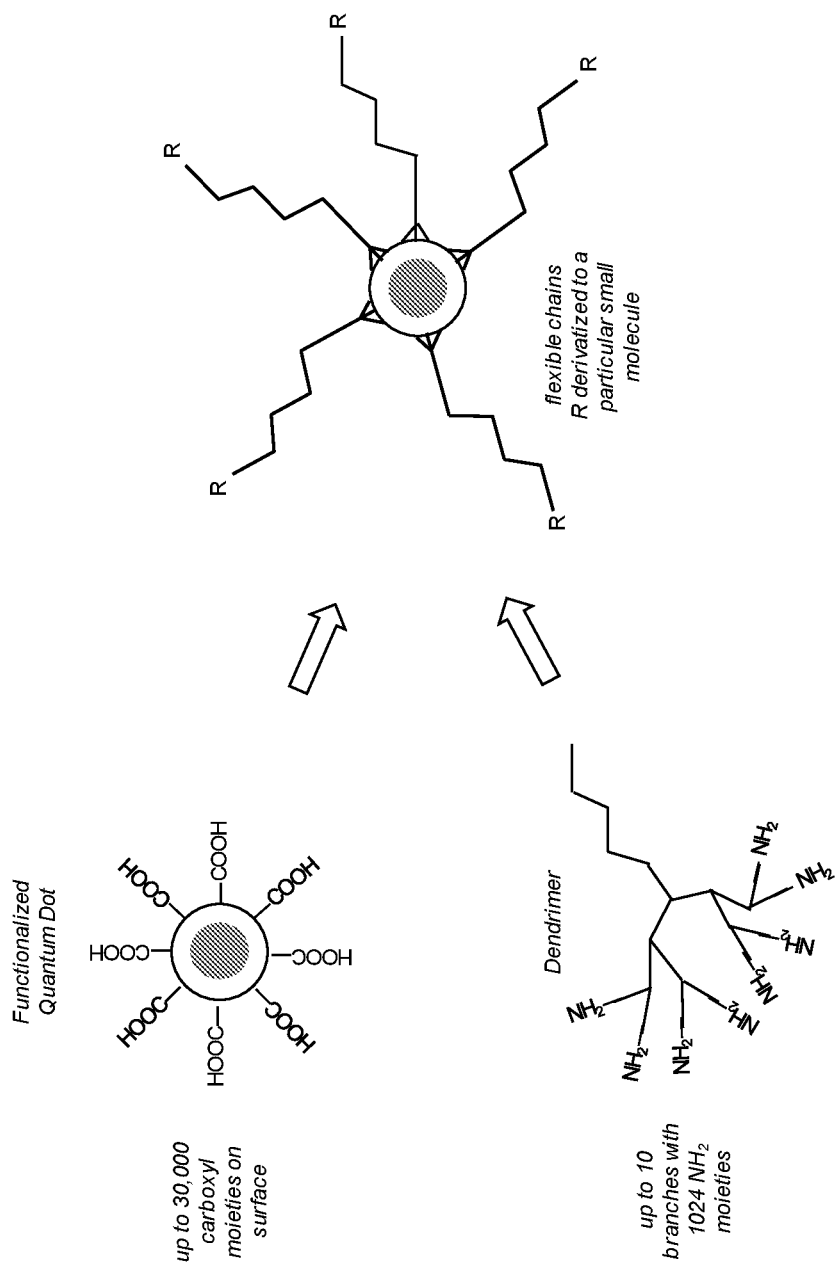
FIG. 19 shows an exemplary quantum dot connected to dendrimers.

FIG. 18 shows exemplary quantum dots that may be functionalized, e.g., with antibodies. A sample of aqueous solution containing quantum dots may be passed through a channel where a flow of a water-immiscible matrix (e.g., oil) intercepts the flow of the aqueous solution to create emulsion droplets containing the quantum dots. Dendrimer quantum dots are known, and dendrimers such as PAMAM dendrimers may be connected to functionalized quantum dots, as shown in FIG. 19. Methods of synthesizing PAMAM dendrimers are known. See e.g., Hong et al., Langmuir 2005, 21, 4257-4261.

If near-infrared two-photon fluorescence excitation is used, and if the sample contains monomer and a photocatalyst, then application of focused ultraviolet light could be used to form beads of polymerized gel within the optical chamber, entrapping specific quantum dots for later collection. The SLAPMi technique uses near-infrared two-photon fluorescence excitation, and it can greatly reduce image scattering that occurs with complex biological samples. The two-photon excitation also gives better particle localization than standard excitation with ultraviolet light and eliminates background fluorescence. Furthermore, the optical technique can collect data at 1000 samples/second.

Quantum dots are available with amine or carboxyl surfaces, ready for attachment of proteins or oligonucleotides.

Since quantum dots are much denser than water, brief application of an ultrasonic wave should oscillate the water around each quantum dot, which could loosen non-specific bound materials but not targets.

In some aspects, the use of quantum dots instead of gel beads has several advantages. For example, only one molecule needs to attach to a quantum dot in order for its diffusive properties to be detected, whereas a gel bead needs to have many analytes bound to its surface. This makes the method faster and more sensitive. Furthermore, the use of multiple quantum dots of each color means multiple measurements. As the graphs of Brownian motion indicate, there are several occurrences of binding which together give a clearer measure of the binding kinetics. The use of SLAPMi optics enables measuring the binding at 1000 Hz. Lastly, there is no labeling required for the analyte, since the quantum dot diffusive behavior is the analytical signal.

For weakly-bound analytes, the graphs of Brownian motion may also show occasional disassociation events, indicated by a sudden rise in the diffusivity of particular quantum dots. It is a fast, real-time measure of binding interactions.

When illuminated by a fluorescence excitation source, quantum dots may exhibit stochastic blinking (PhotoLuminescence Intermittence) of the fluorescence emission. This phenomenon has been extensively studied, and existing literature suggests it may be due to high excitation power resulting in a local electric field, nonradiative Auger recombination, and/or surface trap induced recombination. In some embodiments, this blinking is reduced by adjusting the chemical nature of the quantum dot surface, such as the work by Thomas, Ghimire et al. (2018). In some embodiments, this blinking is reduced by using gradient-alloyed quantum dots, such as the work of Zhang, Wang, et al. (2019). In some embodiments, this blinking is reduced by using thick shells, such as the work of Reid, McBride, et al. (2018).

In some embodiments, the stochastic constellation diffusance disclosed herein is detected using a fluorescence quenching assay. A compound containing a heavy atom that binds to a quantum dot may cause quenching of the quantum dot fluorescence. The inherent quantum dot blinking may interfere with the fluorescence quenching assay, and as disclosed herein, several techniques are available to limit inherent quantum dot blinking.

Since multiple quantum dots may be used within each droplet or gel bead, those quantum dots that blink may simply be excluded from the data analysis, using only the remaining quantum dots that do not blink during a measurement.

Typically, the emission spectrum of quantum dots is relatively narrow and is dependent on the semiconductor composition and physical size of the quantum dot. Single quantum dots typically have a fluorescence emission spectrum band (e.g., color) of about 10 to 15 nm width at room temperature in the visible range.

Quantum dots having aggregate colors of 30 to 50 nm width are commercially available. In these examples, the 30 to 50 nm width of each fluorescence emission spectrum band (e.g., color) means that only about nine emission spectrum bands can be spectrally distinguished when using quantum dot particles. For a collection of merged droplets that each contain only one fluorescent particle, there are thus only nine combinations of sample and reagent that can be unambiguously identified simultaneously within the collection. In these examples, the fluorescent particles function as labels having an address space of only nine combinations.

In some embodiments, the present disclosure comprises merged droplets containing quantum dots in multiple emission colors in various counts, and the address space is considerably larger than droplets that each contains only one fluorescent particle. For example, a merged droplet may contain a 6 reagent-labeled red quantum dots, 9 unlabeled green quantum dots, and 3 un-labeled blue quantum dots.

In some embodiments, with nine possible colors and three possible magnitudes per color, the address space becomes the summation of r(n!/(r!(n−r)!) for r=1 to n, where n=9× 3=27. This gives a total of 2,359,296 combinations.

$$n = 9 \times 3$$

$$\sum_{r=1}^{n} r\left(\frac{n!}{r!(n-r)!}\right) = 2{,}359{,}296$$

A larger number is possible if more than one reagent label is used.

The size of the address space may be increased still further by the use of fluorescent particles with disparate fluorescence lifetimes, and using an optical detection system that can measure fluorescence lifetimes. The size of the address space may be increased still further by the use of chemical agents on the fluorescent particles that cause fluorescence quenching during a binding interaction. The size of the address space may be increased still further by the use of chemical agents (in addition to reagent molecules) on the fluorescent particles that cause absorption of some wavelengths of the fluorescence excitation light. Such chemical agents would reduce fluorescence if the fluorescence excitation light is restricted to such wavelengths. Such chemical agents may be dyes that have bandpass, bandstop, notch, highpass, or lowpass absorption spectra. By using fluorescence excitation light of controlled wavelengths, fluorescent particles having the same emission wavelength but different dye coatings can be distinguished. For example, a red quantum dot having a coating of 350 nm absorbing dye, and a second red quantum dot having a coating of 450 nm absorbing dye, can be distinguished based on fluorescence intensity when the fluorescence excitation light is switched between 350 nm and 450 nm.

In some embodiments, mixing of the aqueous sample with the emulsion of reagent droplets may be implemented by a set of streams that are flowed into a thin-layer analytic chamber. In some embodiments, the dimensions of the analytic chamber are such that its internal volume has a height that is much less than the length and breadth, in the shape of a sheet with a top and bottom face and thin edges. In some embodiments, the walls of the analytic chamber are treated to be hydrophobic. In some embodiments, the walls of the analytic chamber comprise a chemically-bonded surface, or a thin coating of oil or other water-immiscible liquid, such as the emulsion host matrix.

Figure 2:
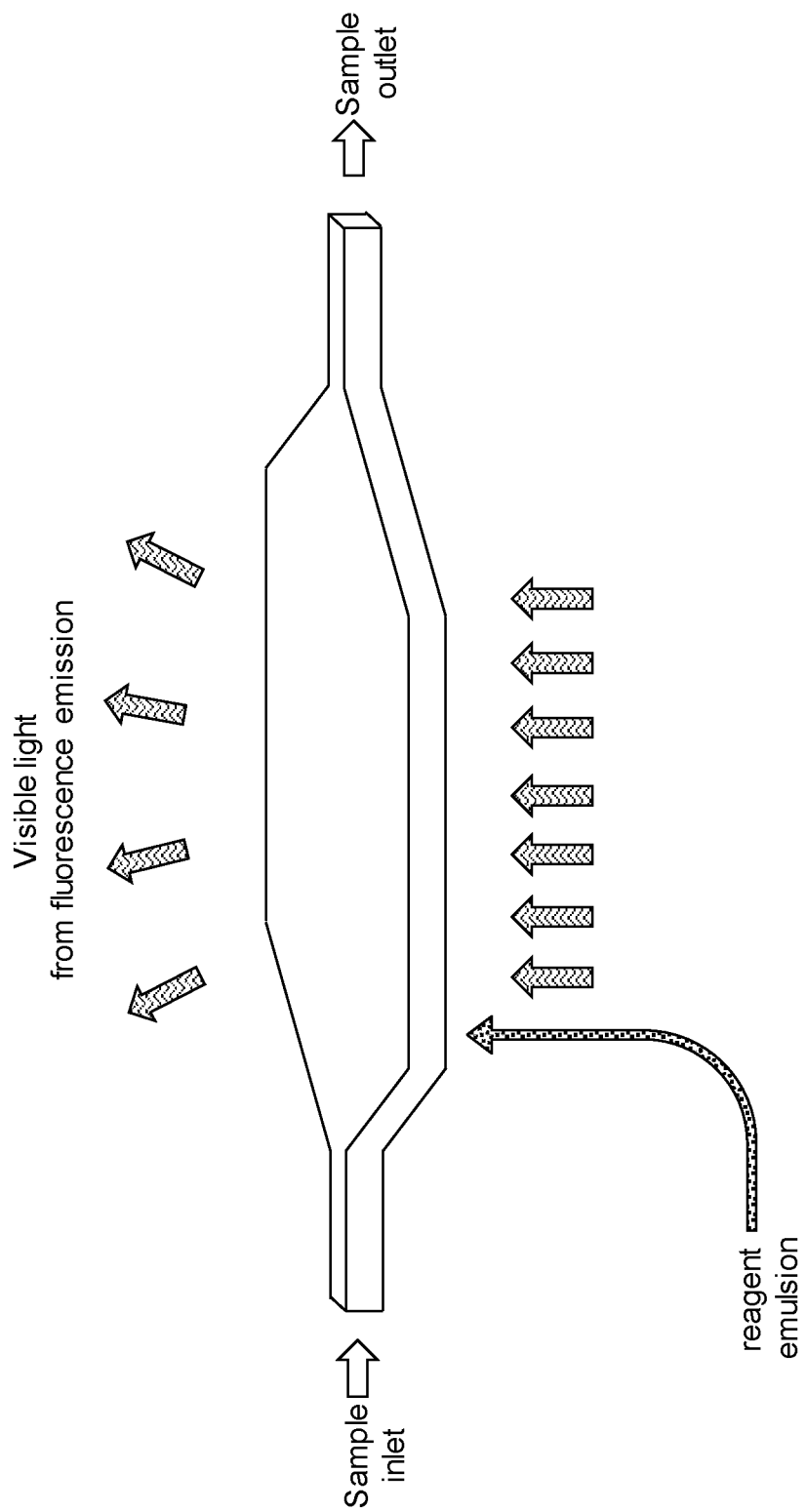
FIG. 2 is a schematic of an exemplary flat optical chamber having a sample inlet and a sample outlet. A sample may be added through the sample inlet as a large droplet in an oil matrix, where the large droplet gets squished into a pancake shape within the chamber. The pancake-shape droplet together with the oil matrix may occupy all or part of the chamber's internal cavity. A reagent emulsion may be injected into the internal cavity through one or more hole in the bottom of the chamber. Fluorescence excitation light is passed from the bottom through the chamber, and visible light from fluorescence emission is detected from above the chamber.

In some embodiments, an aqueous sample is flowed into one end of an analytic chamber, and it spreads out into a thin layer as it passes through the analytic chamber and out the opposite end. For example, as shown in FIG. 1, aqueous sample 3 is flowed into analytic chamber 1, spreads out into a flattened area, and then exits at outlet 4. Fluorescence excitation light 2 from one side of the analytic chamber is passed through the analytic chamber and fluorescence emission 5 exits the analytic chamber on the other side. Emulsion droplets containing quantum dots may be introduced into the chamber, e.g., as shown in FIG. 2.

Figure 3:
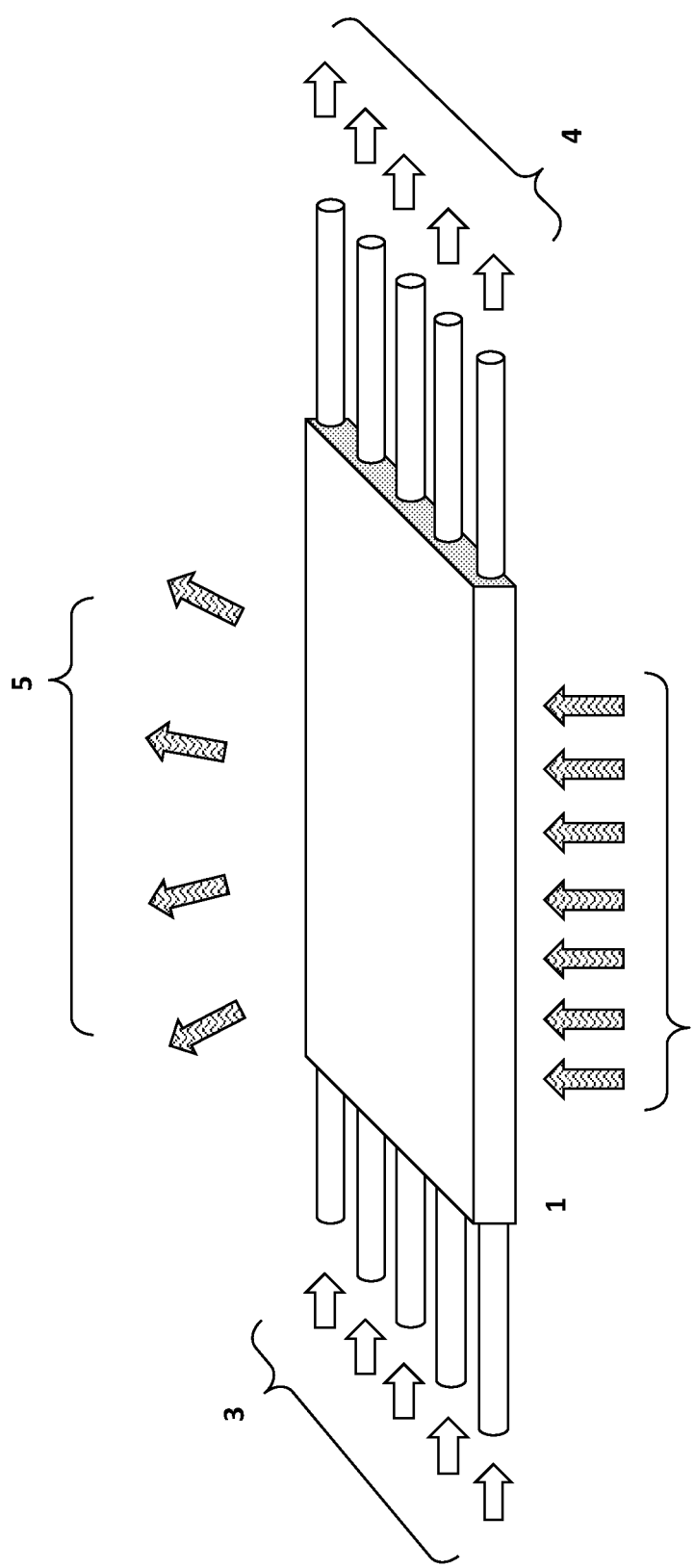
FIG. 3 is a schematic of an exemplary analytic chamber where a set of aqueous samples are passed through it and fluorescence excitation light is passed through it.

In some embodiments, a set of aqueous samples is flowed into multiple inlets of an analytic chamber. For example, as shown in FIG. 3, the set of aqueous samples 3 are flowed into analytic chamber 1, stream through a thin-layer area, and then exit at outlet 4. Fluorescence excitation light 2 from one side of the analytic chamber is passed through the analytic chamber and fluorescence emission 5 exits the analytic chamber on the other side. The analytic chamber may comprise a plurality of separate chambers or channels, each of which has a separate inlet and a separate outlet shown in FIG. 3.

In some embodiments, the aqueous sample is flowed into the analytical chamber before the emulsion or gel beads are flowed into the analytical chamber. In some embodiments, the aqueous sample is flowed into the analytical chamber after the emulsion or gel beads are flowed into the analytical chamber. In some embodiments, the aqueous sample and the emulsion or gel beads are flowed into the analytical chamber simultaneously. In some embodiments, when the emulsion or gel beads are flowed into the chamber, the aqueous sample is flowing through the analytic chamber, e.g., into the chamber through an inlet and out of the chamber through an outlet. In some embodiments, the emulsion droplets or gel beads spread out or are otherwise distributed across an inner surface of the analytical chamber to facilitate subsequent analysis based on diffusion of the fluorophores of the emulsion droplets or gel beads, for example, the emulsion or gel beads may be swept by the aqueous sample flow in one or more direction. In some embodiments, an external force may be applied to the chamber in order to distribute the emulsion droplets or gel beads on an inner surface of the chamber, as or after the emulsion droplets or gel beads are flowed into the chamber. In some embodiments, gravity may be used to distribute the emulsion droplets or gel beads. For example, the analytical chamber may be shaken, rotated, tilted, or otherwise moved or agitated.

In some embodiments, a water-immiscible matrix such as a fluorocarbon oil is pumped into the entrance end of the analytical chamber, causing the aqueous sample to be pushed through the analytical chamber and out the distal end. In some embodiments, a weak gelling agent is added to the aqueous sample in order to minimize laminar flow through the analytical chamber. In some embodiments, the reagent emulsion droplets or gel beads are swept along with the sample flow, assisted by gravity and the weak gelling agent.

The analytical chamber may comprise a substantially planar rigid substrate on which the emulsion droplets or gel beads are located or assembled. In certain embodiments, the substrate is transparent to radiation of the excitation and emission wavelengths used for excitation and detection of various labels, (e.g., fluorescent dyes, quantum dots, plasmon resonant particles, nanoclusters, or any suitable combination thereof), e.g., between approximately 400-900 nm. Materials such as glass, plastic, quartz, etc., are suitable. The emulsion droplets or gel beads may adhere to the substrate and may optionally be affixed to the substrate using any of a variety of methods. The substrate may or may not be coated with a substance that enhances adherence or bonding, e.g., silane, polylysine, etc. The substrate may have a well or depression to contain the emulsion droplets or gel beads prior to merging them into the sample to be analyzed. In various embodiments, a raised barrier or mask may be used for this purpose.

Figure 4:
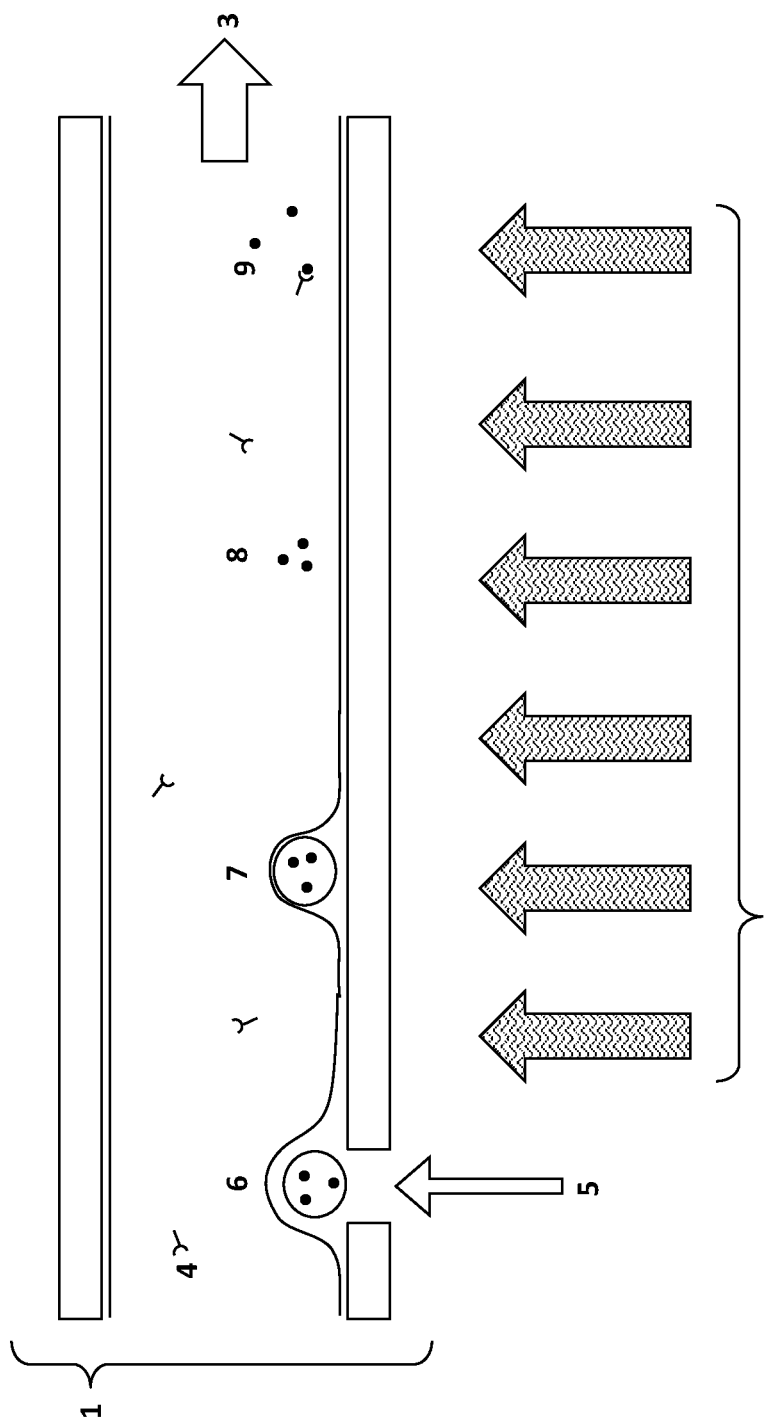
FIG. 4 is a schematic of an exemplary emulsion droplet being swept through an analytic chamber and then demulsifying into a constellation of fluorescent particles.

In some embodiments, as the aqueous sample passes through the analytic chamber, a stream of emulsion is flowed into a hole at one face of the analytic chamber. For example, as shown in FIG. 4, while aqueous sample 3 flows through analytic chamber 1, emulsion or gel beads 5 is flowed into the analytic chamber. Each emulsion droplet or gel bead forms a bump 6 that is swept down the length of analytic chamber 1 and trapped under a sheet of aqueous sample 3 (much like small balls under a carpet), pressing the emulsion droplets very close to the aqueous sample. Emulsion droplets (e.g., bumps 6) may be aqueous droplets separated from the aqueous sample by a thin layer of water-immiscible matrix such as an oil. At this stage, the fluorescent particles (and any analyte-interacting reagent associated therewith) are trapped inside the emulsion droplets and do not contact the aqueous sample. Swept bump 7 is demulsified to a small constellation 8 of fluorescent particles. This constellation diffuses outward to a larger constellation 9. Some of the fluorescent particles may combine with an analyte molecule 4 in the aqueous sample, affecting the diffusivity of the fluorescent particle. Fluorescence excitation light 2 is directed through the analytic chamber 1 during this process.

In some embodiments, application of a momentary strong electric field is used to stimulate demulsification, wherein the emulsion droplets merge with the aqueous sample, allowing the reagent fluorescent particles to interact with sample analyte. Other methods may also be used to cause demulsification, such as by use of oppositely-charged surfactants or demulsification agents added to the sample or water-immiscible host matrix. In some embodiments, application of an electric field is used to cause electrophoretic motion of components of the merged aqueous sample and emulsion droplets.

In some embodiments, multiple holes with multiple different emulsions are used. In some embodiments, the multiple holes are spaced apart sufficiently that the emulsion droplets do not interact.

In some embodiments, the analytic chamber is shaped such that flow of aqueous sample forms a long snaking path through it. This provides an extended duration for the fluorescent particles to be observed. Different emulsions may be added at different times, so that the emulsion droplets are spaced apart.

In some embodiments, the analytic chamber includes multiple inlets for a variety of aqueous samples to be flowed at the same time. These flows may be separated by barriers. The emulsion droplets may be flowed into the junction between two aqueous sample inlets.

In some embodiments, the emulsion droplets may contain gelled fluid. The gelled fluid may be melted or enzymatically depolymerized after insertion into the analytic chamber. In some embodiments, instead of emulsion droplets, gel beads that contain fluorescent particles may be used. In some embodiments, the fluorescent particles are released after gel melting or enzymatic depolymerization. Alternatively, the emulsion droplets and their water-immiscible host matrix may be replaced by gel beads suspended in an aqueous matrix, where the fluorescent particles are released after gel melting or enzymatic depolymerization of the gel.

Figure 6:
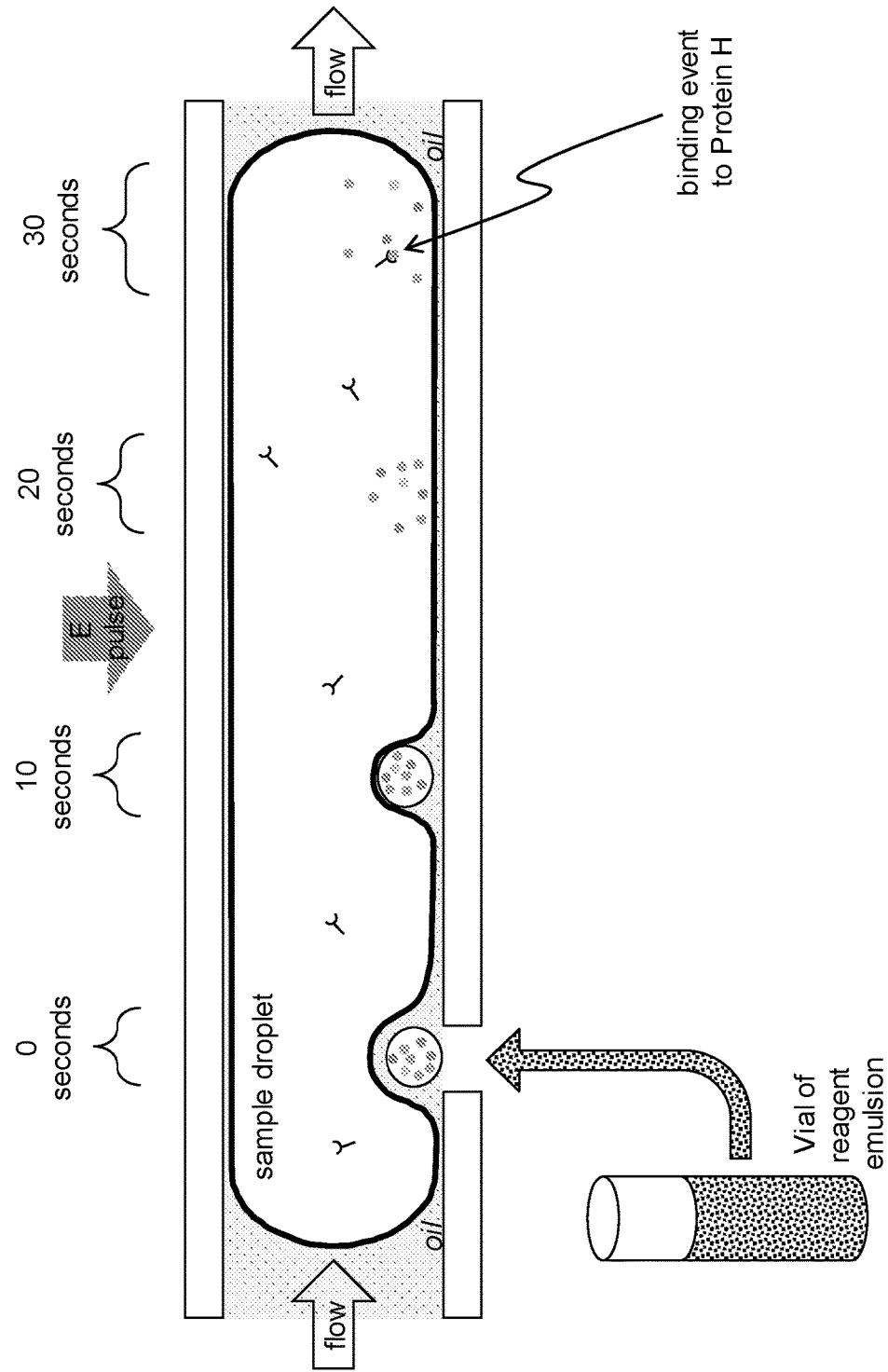
FIG. 6 is a schematic of a side view of an exemplary optical chamber, showing an emulsion droplet being swept through the chamber and then demulsified to merge with a large sample droplet (e.g., as described in connection with FIG. 2), and expand into a constellation of fluorescent particles in the large sample droplet. For example, during the expansion, Protein H on a blue quantum dot from the emulsion droplet binds to an analyte in the large sample droplet. A weak pulse of electric field may be used to demulsify the droplets, allowing the quantum dots to diffuse into the large sample droplet. Quantum dots from each emulsion droplet form an expanding constellation of quantum dots, and a laminar flow profile can be mitigated by adding a weak gelling agent to introduce static friction.
Figure 7:
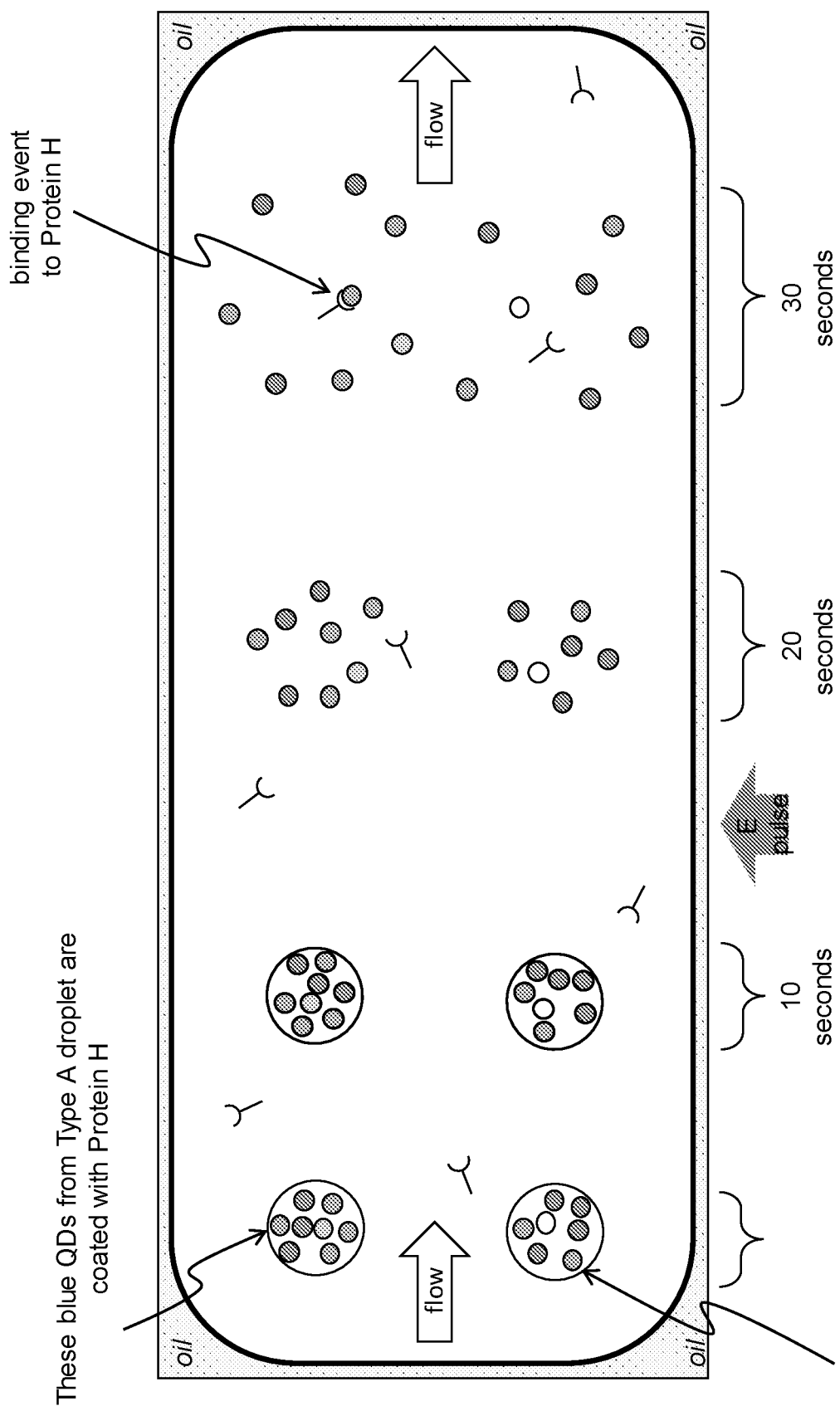
FIG. 7 is a schematic of a top view of an exemplary optical chamber, showing two types of emulsion droplets (Type A with 3 red, 1 green, and 4 blue, and Type B with 4 red, 1 yellow, and 2 blue) being swept through the chamber and then demulsified to merge with a sample, each expanding into a constellation of fluorescent particles in the sample. Blue quantum dots from Type A emulsion droplets are coated with Protein H, while blue quantum dots from Type B emulsion droplets are coated with Protein C. The analyte in the sample binds to Protein H but not Protein C. During the expansion, the analyte binds to blue quantum dots from Type A emulsion droplets but not blue quantum dots from Type B emulsion droplets.
Figure 8:
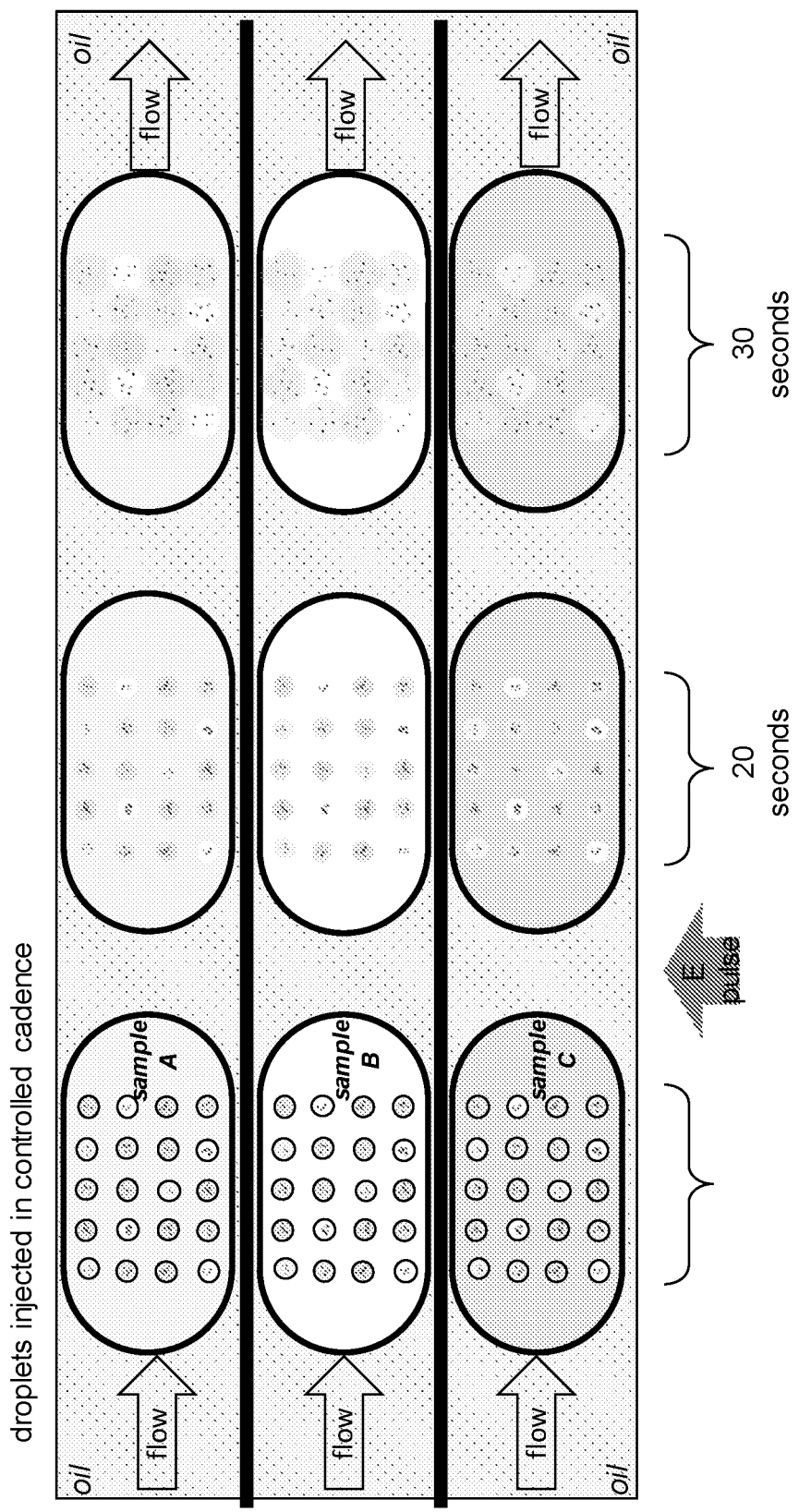
FIG. 8 is a schematic of an exemplary chamber with multiple channels for multiplexed analysis, for example, for synergistic small-molecule combinations. The emulsion droplets may be injected into the separate channels in controlled cadence.
Figure 9:
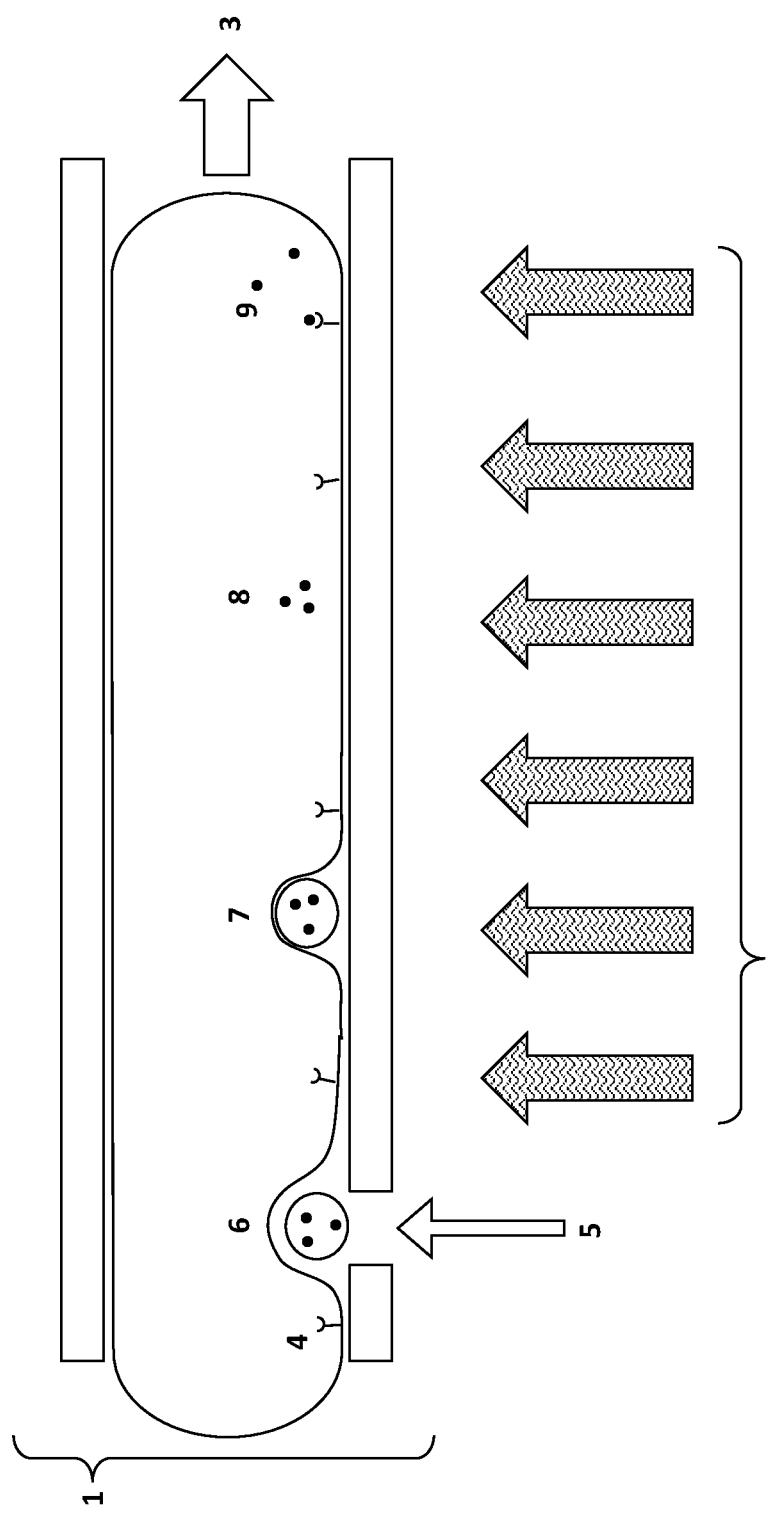
FIG. 9 is a schematic of an exemplary emulsion droplet being swept through an analytic chamber and then demulsifying into a constellation of fluorescent particles, where the sample itself is in the form of a large droplet and the analyte (e.g., a surfactant analyte) is concentrated at the interface between aqueous sample droplet and the water-immiscible matrix.
Figure 10:
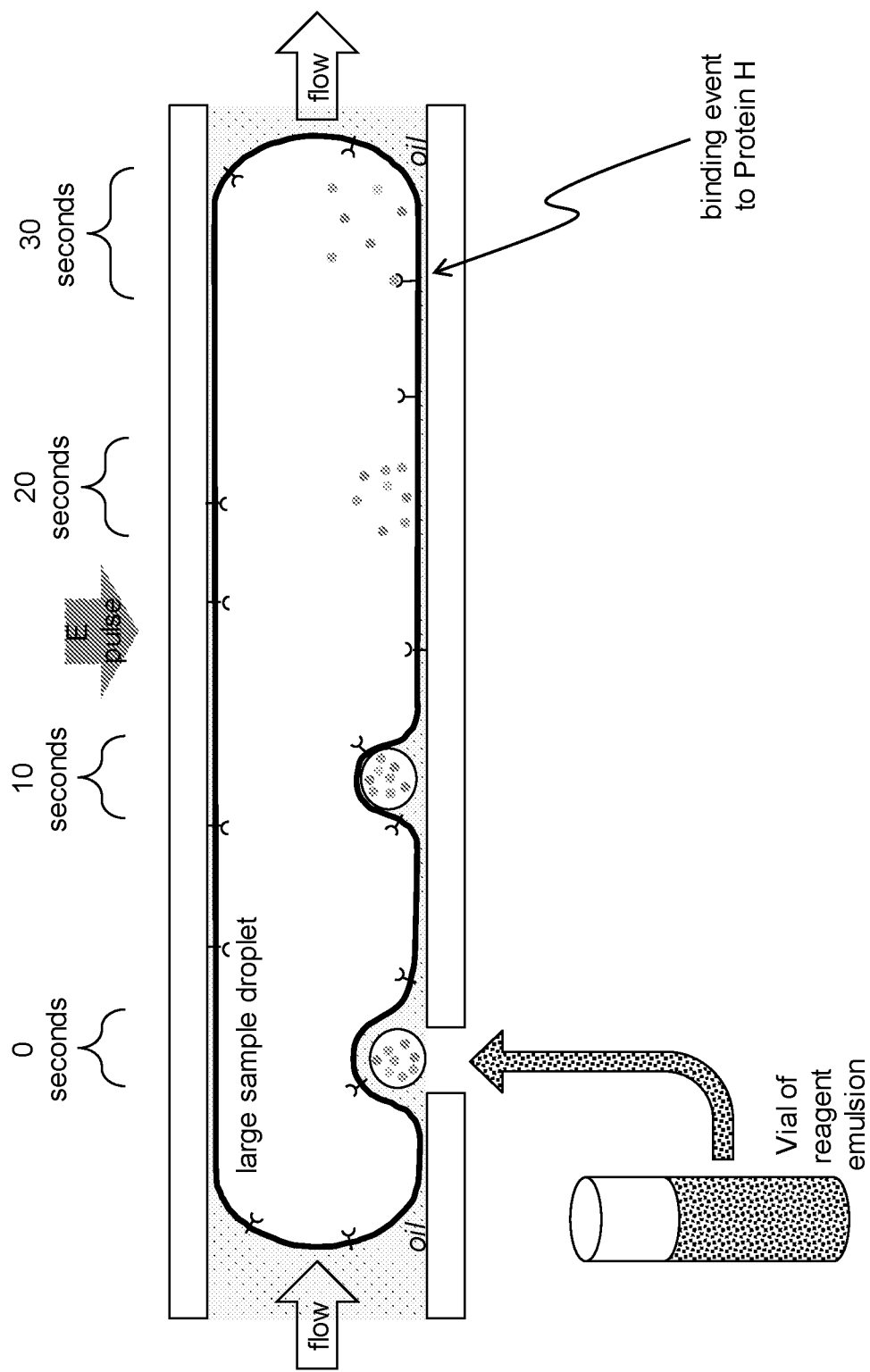
FIG. 10 is a schematic of a side view of an exemplary optical chamber, showing an emulsion droplet being swept through the chamber and then demulsified to merge with a large sample droplet (e.g., as described in connection with FIG. 2), and expand into a constellation of fluorescent particles in the large sample droplet. For example, during the expansion, Protein H on a blue quantum dot from the emulsion droplet binds to a surfactant analyte in the sample, where surfactant analytes are concentrated at the interface between the aqueous sample droplet and the water-immiscible matrix. A weak pulse of electric field may be used to demulsify the droplets, allowing the quantum dots to diffuse into the large sample droplet. Quantum dots from each emulsion droplet form an expanding constellation of quantum dots, and a laminar flow profile can be mitigated by adding a weak gelling agent to introduce static friction.

In some embodiments, an aqueous sample is present in the form of a sample droplet in an immiscible matrix, for example, as shown in FIG. 6 or FIG. 9. Some analytes may be concentrated at the surface interface between the sample droplet and the water-immiscible matrix. In this case, the diffusion of the fluorescent particles may be largely restricted to a two-dimensional plane of the surface interface. In some embodiments, a change in the diffusion behavior of a fluorescent particle from a three-dimensional motion to a two-dimensional motion is indicative of binding between the fluorescent particle and the analyte. Examples of such analytes include cell membrane proteins.

FIG. 9 shows that emulsion droplet or gel bead 5 may be flowed into analytic chamber 1, for example, while aqueous sample 3 is present in the analytic chamber. Each emulsion droplet or gel bead forms a bump 6, and the bumps may be swept down the length of the analytic chamber or otherwise spread out from each other on a surface of the chamber. The emulsion droplets or gel beads may be trapped under a sheet of aqueous sample 3, again much like small balls under a carpet. In some embodiments, the emulsion droplets or gel beads are pressed very close to the aqueous sample. Emulsion droplets (e.g., bumps 6) may be aqueous droplets separated from the aqueous sample by a thin layer of water-immiscible matrix such as an oil. At this stage, the fluorescent particles (and any analyte-interacting reagent associated therewith) are trapped inside the emulsion droplets and do not contact the aqueous sample. Swept bump 7 can then be demulsified, e.g., after the application of an electric pulse, such that the thin gap of water-immiscible matrix is breached, allowing each aqueous droplet to merge into the aqueous sample. The fluorescent particles (and any analyte-interacting reagent associated therewith) in each aqueous droplet are no longer confined by the water-immiscible matrix and may diffuse in the aqueous sample to form a small constellation 8 of fluorescent particles. This constellation diffuses outward to a larger constellation 9. Some of the fluorescent particles may combine with an analyte molecule 4 in the aqueous sample, affecting the diffusivity of the fluorescent particle. As shown in FIG. 4, analyte molecules 4 may be concentrated at the interface between aqueous sample 3 and the water-immiscible matrix. Fluorescence excitation light 2 is directed through the analytic chamber 1 during at least a portion of this process. For example, fluorescence excitation light may be used during the expansion of small constellation 8 into larger constellation 9, where all or a subset of the fluorescent particles of one or more emulsion droplets are tracked and their fluorescence emission characteristics are recorded and/or analyzed.

In some embodiments, the analytic chamber is constructed such that fluorescence excitation light can be applied to the merged aqueous sample and emulsion droplets. Fluorescence excitation light is applied such that it passes into a surface of the analytic chamber, through the merged aqueous sample and emulsion droplets, and out the other surface.

In some embodiments, the surfaces inside the analytic chamber may be textured to modify fluid flow through the analytic chamber, or to modify the movement of droplets within the analytic chamber. For example, grooves may be manufactured in a surface to ensure movement of droplets along specific paths.

In some embodiments, the flow rate of the aqueous sample through the analytic chamber is constant. In other embodiments, the flow rate of the aqueous sample through the analytic chamber varies with time. For example, the flow rate of aqueous sample through the analytic chamber may be pulsed.

In some embodiments, an acoustic wave, e.g., a high-frequency sound wave such as an ultrasound, is applied to the analytic chamber. For example, a standing acoustic wave may be used to cause controlled oscillation (or cavitation) of the aqueous sample and the fluorescent particles it contains, altering the diffusion characteristics of the fluorescent particles. This may be especially pronounced if the fluorescent particles have a density that is significantly different from than the aqueous sample. By rapidly moving the environment around a fluorescent particle, it may be possible to discriminate against weakly bound components that are non-specifically adsorbed onto the fluorescent particle. In some aspect, the method comprises applying sound waves across the width of the analytic chamber, so that the quantum dots are given a degree of non-random motion that helps with discriminating between random diffusivity fluctuations and rapidly alternating associative and dissociative behavior.

In some embodiments, quantum dots are significantly denser than water, e.g., quantum dots may contain PbS or CdS. In some embodiments, sonication such as ultrasonication is applied to quantum dots, causing them to shake more than Brownian motion and such shaking may dislodge materials that are non-specifically bound. Ramping the ultrasonic power may indicate strength of binding to the quantum dots.

In some embodiments, a magnetic field is applied to the analytic chamber. For example, reagent droplets that are manufactured to contain magnetic particles may be pulled in controlled directions by an applied magnetic field.

In some embodiments, the fluorescent particles may be weakly bound to quenching agents that can be competitively adsorbed away to sample proteins, resulting in increased fluorescence of the fluorescent particles.

In some embodiments, the fluorescence excitation light is non-polarized. In some embodiments, the fluorescence excitation light is linearly, circularly, elliptically polarized, or trochoidally polarized. The propagation mode through the analytic chamber may be transverse electromagnetic (TEM), transverse electric (TE), transverse magnetic (TM), or a hybrid thereof.

In some embodiments, the fluorescence excitation light is coherent. In other embodiments, the fluorescence excitation light is continuous or pulsed. The fluorescence excitation light may be applied at a variety of incidence angles to the analytic chamber. In some embodiments, the fluorescence excitation light comprises, consists essentially of, or consists of an infrared light. In some embodiments, the use of infrared light means that optical scattering is reduced or minimized, allowing precise quantum dot localization.

In some embodiments, the fluorescence excitation light is spatially uniform. In other embodiments, the fluorescence excitation light is spatially patterned. The fluorescence excitation light may consist of a single frequency, or consist of multiple frequencies, or as a frequency comb. Optical frequency combs may be used to provide equidistant frequency markers in the infrared, visible and ultraviolet and can link an unknown optical frequency to a radio or microwave frequency reference. Methods of generating a frequency comb are known in the art, for example, as disclosed in U.S. Pat. No. 7,982,944.

In some embodiments, the fluorescence excitation light is applied in a manner similar to confocal microscopy. In some embodiments, the fluorescence excitation light is applied in a manner similar to Structured Illumination Microscopy (SIM). In some embodiments, the fluorescence excitation light is applied in a manner similar to STochastic Optical Reconstruction Microscopy (STORM). In some embodiments, the fluorescence excitation light is applied in a manner similar to Point-Scanning Two-Photon Microscopy. In some embodiments, the fluorescence excitation light is applied in a manner similar to Scanned Line Angular Projection Microscopy (SLAPMi). In some embodiments, the fluorescence excitation light is applied in a manner similar to Ghost Imaging (GI) or Ghost Imaging by Sparsity Constraints (GISC). In some embodiments, use of the fluorescence excitation light according to the above technologies facilitates rapid and precise localization of the fluorescent particles within scattering media such as biological samples.

In some embodiments, the fluorescence emission light is refracted or internally reflected by droplets having a refractive index different from the matrix, producing an image pattern that may be deconvoluted to identify the position of the fluorophore.

In some embodiments, the aqueous sample is transparent to the fluorescence excitation light. In some embodiments, the excitation light causes fluorescence of fluorescent particles, and the fluorescence is emitted in all directions. In some embodiments, stray excitation light is removed by the use of an optical filter that absorbs the frequency of the excitation light, or by a reflective surface that preferentially reflects away the frequency of the excitation light.

Figure 11:
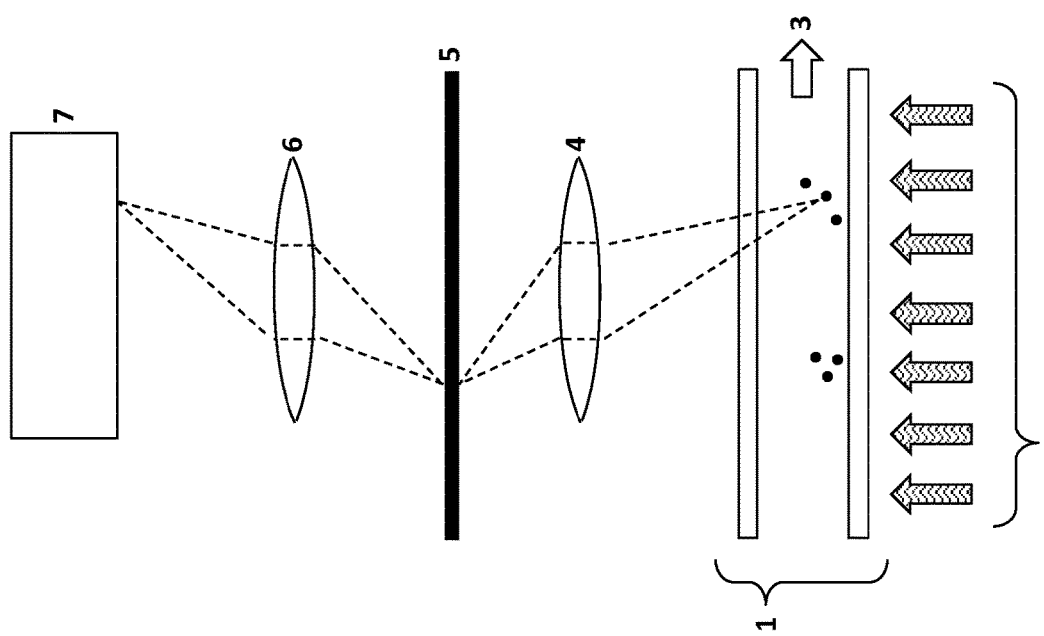
FIG. 11 is a schematic of an exemplary optical system for measuring fluorescence emission light from an exemplary analytic chamber.
Figure 12:
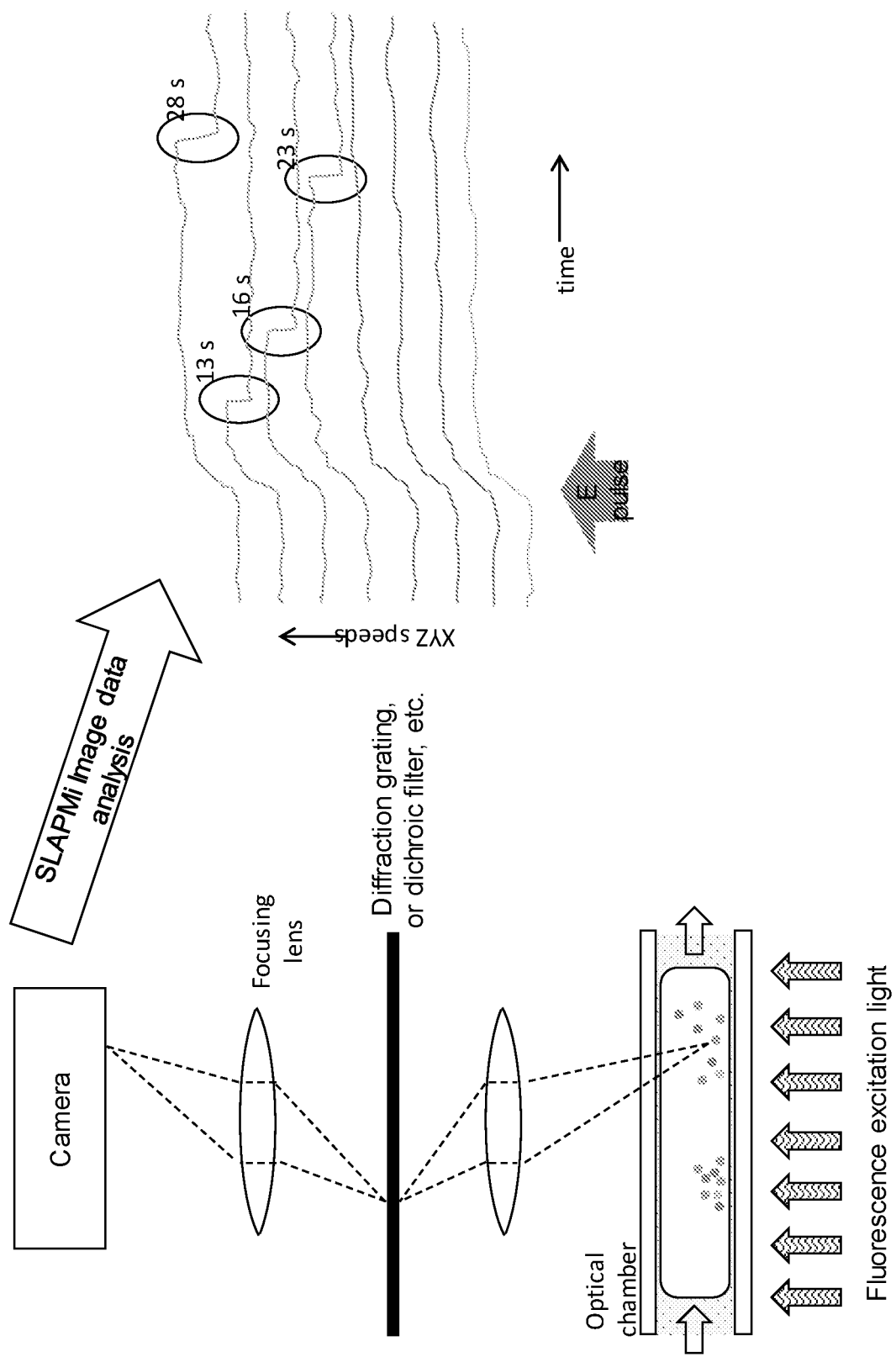
FIG. 12 is a schematic of an exemplary optical system for measuring fluorescence emission light from an exemplary analytic chamber, where SLAPMi image data is collected by the camera and Brownian motion of each quantum dot in each constellation is tracked over time. An exemplary graph for one droplet constellation is shown, and there are many simultaneous droplet constellations in the camera image. In the exemplary graph, binding events have occurred for the blue quantum dots at 13, 16, 23, and 28 s, giving a measure of kinetics or concentration, while data for the red or green quantum dots do not show binding events. Since these blue quantum dots are associated with droplet of 4 blue+3 red+1 green (Type A emulsion droplet in FIG. 7), indicating these blue quantum dots are coated with Protein H, therefore the binding occurs between Protein H and an analyte in the sample.

In some embodiments, the analytic chamber is constructed such that fluorescence emission can be emitted to an optical system. For example, as shown in FIG. 11, analytic chamber 1 contains fluorescent particles within aqueous sample 3. Fluorescence excitation light 2 is directed through the analytic chamber, causing the fluorescent particles to produce fluorescence emission light. A lens 4 focuses the fluorescence emission light from the fluorescent particles onto a diffraction grating 5. Another lens 6 focuses the light from the diffraction grating 5 onto a camera 7. Use of the diffraction grating is optional.

In some embodiments, when an emulsion droplet first merges with the aqueous sample, its fluorescent particles are close to each other. If the emulsion droplet had contained, for example, approximately 6 red-emitting fluorescent particles, 9 green-emitting fluorescent particles, and 3 blue-emitting fluorescent particles, then the camera can observe a bright red spot, a very bright green spot, and a dim blue spot, along a line produced by the diffraction grating. After application of a momentary strong electric field to stimulate demulsification, the fluorescent particles may be released from the emulsion droplet and may move stochastically by Brownian motion, e.g., when the aqueous sample is not flowing. As the individual fluorescent particles diffuse outward within the aqueous sample, they eventually travel a distance sufficient for the camera to resolve them, so that the individual intensities of the fluorescent particles can be tracked. In some embodiments, movement and fluorescent intensities of the fluorescent particles are tracked over time as diffusion continues, so that the camera observes an expanding constellation.

In some embodiments, the spectral composition and relative color intensities of the constellation provide a means for identifying the originating emulsion droplet, and thereby the identity of the analyte binding reagent(s) that it contains.

Figure 5:
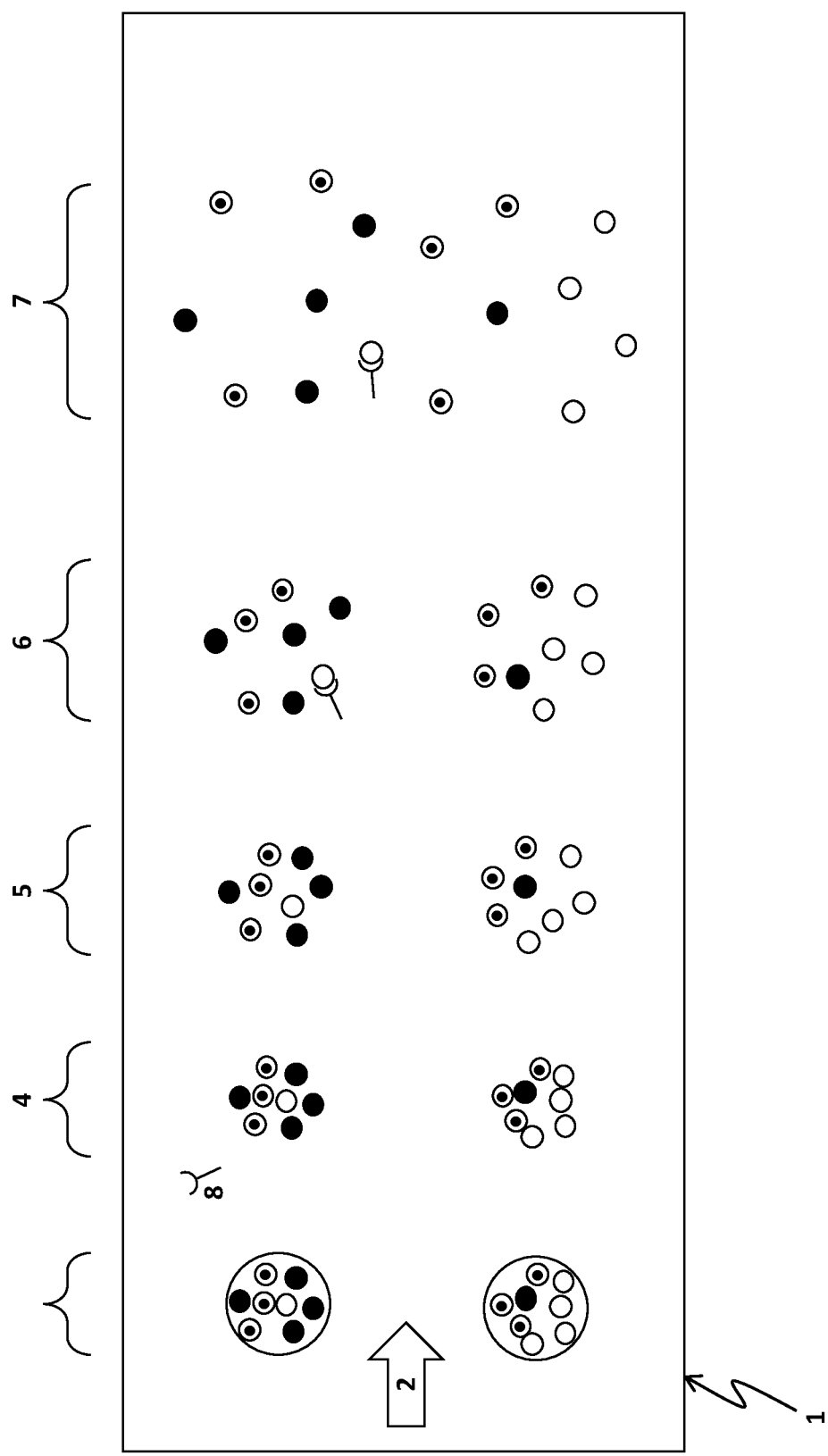
FIG. 5 is a schematic of representative camera images of the analytic chamber, showing two different emulsion droplets droplet being swept through an analytic chamber and then demulsifying into a constellation of fluorescent particles.

In some embodiments, a large number of disparate emulsion droplets are merged into the aqueous sample, where each droplet can be identified by the camera. For example, the source of the emulsion droplets may be a vial containing a large library of emulsion droplets, where each droplet has a unique combination of fluorescence emission spectral composition and relative color intensities for the specific analyte binding reagent(s) that it contains. In some embodiments, randomly merging those droplets into the aqueous sample and observing the diffusion constellation of each provide identification of the specific analyte binding reagent(s) present in the droplets. A representation of a set of camera images is shown in FIG. 5. For example, the analytic chamber contains flowing aqueous sample 2, carrying along with it two different emulsion droplets 3. As the two emulsion droplets are carried along by the aqueous sample, they are demulsified to form two dense constellations 4 of fluorescent particles. The fluorescent particles slowly diffuse outwards, expanding the two constellations to form expanded constellations 5. A molecule of analyte 8 in the sample binds to a fluorescent particle 6. The constellations continue to expand, eventually overlapping each other in 7. Continual optical tracking of each fluorescent particle allows identifying which emulsion droplet it originated from, and thus the identity of its analyte binding reagent.

In some embodiments, the excitation light is spatially uniform, and stochastic diffusion of the fluorescent particles causes a corresponding stochastic variation in the fluorescence emission position of each fluorescent particle.

In some embodiments, the excitation light is structured in a spatial pattern, and stochastic diffusion of the fluorescent particles into and out of regions of high excitation light intensity causes a corresponding stochastic variation in the fluorescence emission of each fluorescent particle.

In some embodiments, the fluorescent particle is chemically associated with, and optionally covalently bound to, the analyte binding reagent. In some embodiments, the stochastic movement of the fluorescent particle is affected by a binding interaction with an analyte. For example, the binding interaction may increase hydrodynamic drag on the fluorescent particle.

In some embodiments, changes in the stochastic movement of the fluorescent particle by a binding interaction cause changes in the stochastic behavior of the fluorescence emission position and/or magnitude. In some embodiments, the degree of stochastic behavior of the fluorescence emission position and/or magnitude after each droplet demulsification (or gel depolymerization) event constitutes an optically-detected signal for the binding interaction of the analyte to the reagent. In some embodiments, the degree of stochastic behavior among all fluorescent particles of a given emission color is compared to establish a relative baseline for stochastic behavior when they are not binding.

In some embodiments, the attachment of a fluorescent particle to one side of an analyte produces an asymmetric geometry, thereby affecting stochastic movement. In some embodiments, statistically, the movement is not purely stochastic but is constrained by the asymmetric geometry. Various statistical methods may be used to differentiate the stochastic movement of a bound fluorescent particle from that of an un-bound fluorescent particle that has a symmetric geometry, in addition to the magnitude of the Brownian movement.

In some embodiments, the presence of an analyte can be determined by the presence of a change in the stochastic behavior of the magnitude of the fluorescence emission. In some embodiments, the concentration of an analyte in the sample can be determined by the time required for a change in the stochastic behavior of the magnitude of the fluorescence emission. In some embodiments, the concentration of an analyte in the sample can be determined by the proportion of fluorescent particles that exhibit a change in the stochastic behavior of the magnitude the fluorescence emission. Generally this applies when the analyte is at sufficiently low concentrations in the sample and that not all fluorescent particles bind an analyte molecule.

In some embodiments, the concentration of an analyte is determined by the degree of saturation of the binding sites on the fluorescent particle, which can be determined by a comparison of the measured change in the stochastic behavior of the magnitude of the fluorescence emission to the expected change in the stochastic behavior of the magnitude of the fluorescence emission.

In some embodiments, the association and dissociation constants for the binding interaction between the analyte and the reagent are determined by varying the concentration of the aqueous sample, e.g., by diluting an initial sample to provide diluted samples of various concentrations. For example, for a sequence of measurements where the analyte concentration is successively smaller, the binding interaction (as indicated by the stochastic movement) is successively smaller. Since binding interactions at equilibrium are dependent on concentration, a graph of binding interaction versus concentration yields the association and dissociation constants.

In some embodiments, the association and dissociation constants for the binding interaction between the analyte and the reagent are determined by measuring changes in the stochastic behavior of the magnitude of the fluorescence emission over time. For example, disclosed herein is a method comprising allowing association to occur for a period of time, followed by dissociation for a period of time, followed by association again. In some embodiments, the stochastic behavior of the magnitude of the fluorescence emission over time is indicative of analyte concentration, binding strength, and/or binding kinetics, during the association and disassociation.

In some embodiments, the expanding constellation expands sufficiently to overlap with other constellations in the analytic chamber. After this stage, unique identification of each fluorescent particle will be more complex, but may be managed by tracking the fluorescent particles over time and/or applying statistical techniques.

For example, as a constellation expands, each fluorescent particle will be identified by the population of its constellation. Eventually, an identified fluorescent particle may randomly overlap with an identified same-colored fluorescent particle from another constellation, and then continue diffusing away from the overlap. Statistical techniques may be used to tell which particle is from which constellation and therefore which initial emulsion droplet. For each of the two fluorescent particles, there is a 50% chance that its observed diffusivity behavior is due to one analyte binding reagent, and a 50% chance that that it due to another. However, since there are multiple particles of each type, the diffusivity behavior of the ambiguously identified fluorescent particle can be compared against the other particles of its type, and probabilities assigned to the possible identities.

Compositions and methods for single particle tracking are known. See, e.g., Zhang et al., "Quantum Dot Based Biotracking and Biodetection," Anal. Chem. 2019, 91, 532-547. In those methods, a fluorophore (such as a quantum dot, fluorescent protein, or gold nanodots) is attached to a molecule, and then the fluorophore gets randomly tugged around by its molecule on a cell membrane or within a cell, in order to observe and study cellular transport processes. Researchers have found the expected steric and torpidity effects of large quantum dots and gold nanodots compared to molecular fluorophores.

In certain aspects, the compositions and methods disclosed herein are different from known single particle tracking techniques. For example, as disclosed herein, the diffusivity of quantum dots is used to measure the presence and/or strength of binding interactions, and the identities of the quantum dots arise from their association with other quantum dots within their emulsion drop and expanding constellation.

In some embodiments, during manufacture of the aqueous droplets, there is provided a degree of randomness associated with the particular counts of fluorescent particles. For example, when attempting to manufacture aqueous droplets with 6 red-emitting fluorescent particles, 9 green-emitting fluorescent particles, and 3 blue-emitting fluorescent particles, there may be some aqueous droplets that have 5 red-emitting fluorescent particles, 9 green-emitting fluorescent particles, and 4 blue-emitting fluorescent particles. Those aqueous droplets may still be used by an analysis algorithm as long as their identity is not ambiguous. If their identity is ambiguous, then the optical data from the fluorescent particles associated with those aqueous droplets may be excluded from analysis.

In some embodiments, a weak gelling agent is added to the aqueous sample in order to minimize laminar flow through the analytic chamber. Laminar flow typically tends to spread out the constellation of fluorescent particles. In cases where multiple aqueous samples are flowed into the analytic chamber via multiple inlets, a gelling agent is used to suppress convective mixing of the multiple aqueous samples.

In some embodiments, a viscosity-enhancing agent is added to the aqueous sample in order to slow down diffusion of the fluorescent particles in the analytic chamber. Examples of viscosity-enhancing agents include glycerin, polyethylene glycols, and polyvinyl alcohols.

In some embodiments, a non-Newtonian agent is added to the aqueous sample to further modify the diffusion of the fluorescent particles in the analytic chamber. This includes shear-thinning and/or shear-thickening agents.

In some embodiments, an electric field is applied to the analytic chamber. Charged components of the merged aqueous sample, such as the fluorescent particles and protein molecules, may then experience a force that causes deterministic movement (distinct from stochastic movement, which is non-deterministic). This is referred to as electrophoretic movement. If the electric field is oscillated, these charged components will also oscillate. In some embodiments, such oscillation is useful for discriminating against non-specific binding interactions. In some embodiments, non-specific binding is weak while analyte binding is strong, and oscillation of a fluorescent particle can temporarily shake off weakly-bound components. This can be observed in the stochastic behavior of the magnitude of the fluorescence emission.

In some embodiments, the momentary strong electric field that is used to stimulate demulsification causes a momentary shift in fluorescent particle position due to electrostatic interactions. In some embodiments, the signal is useful for analysis since it is dependent on the net electric charge of the fluorescent particle.

Each camera image is an integration of the light arriving during the exposure time of the image. In some embodiments, if the diffusive motion of the fluorescent particles is slower than the exposure time, then the fluorescence emission light forms a set of small focused points in each camera image, and the movement of those points over a series of camera images gives information about the diffusive motion of the fluorescent particles.

Figure 13:
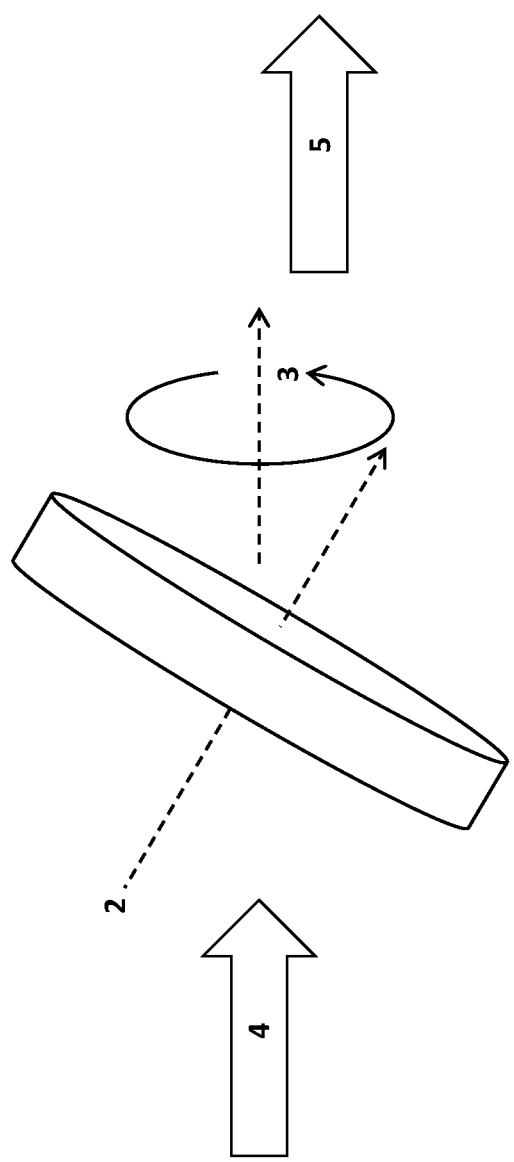
FIG. 13 is schematic of an exemplary nutating disk and the camera images that are expected without and with the nutating disk.
Figure 13:
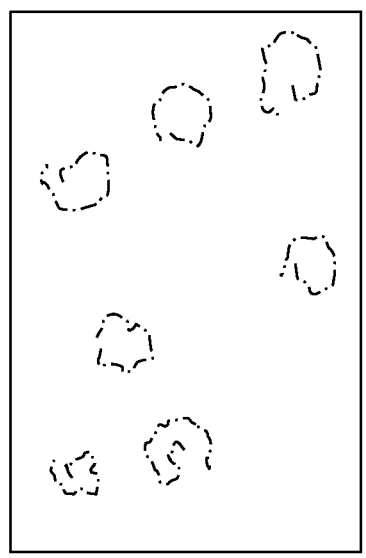
Figure 13:
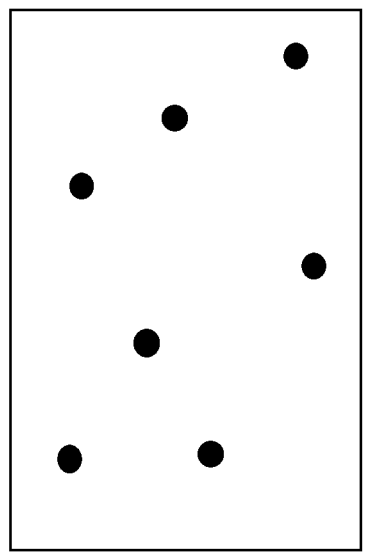

If the diffusive motion of the fluorescent particles is faster than the exposure time, then the fluorescence emission light forms a set of large blurred spots in each camera image; the small focused point of each fluorescent particle traces a random path during the exposure that blurs into a large spot that is difficult to analyze over a series of camera images. In some embodiments, to capture faster motion, a nutating disk is used. For example, as shown in FIG. 13, fluorescence emission light 4 is passed through nutating disk 1 having a perpendicular axis 2. Perpendicular axis 2 rotates around a second axis 3, and exiting light 5 is given a translational shift. Instead of each fluorescent particle producing a point in the camera focal plane that must be optically tracked over a set of exposures, that point is moved rapidly in a circle (or other pattern) by the nutating disk during an exposure. Instead of forming a set of large blurred spots 6 in a camera image, the random motion of the points are stretched out into approximate circles 7 in a camera image, where the deviations from circular are indicative of the random motions occurring during an exposure. This way, more pixels are employed to measure the fluorescence emission light from each fluorescent particle, allowing more time resolution. In some embodiments, a higher-sensitivity camera is used to compensate for the lessened photon rate per pixel due to the use of a nutating disk.

In some embodiments, the method disclosed herein comprises implementing an active system feedback, where the population of aqueous droplets inserted into the analytic chamber is changed based on the measurements obtained by earlier aqueous droplets. For example, an initial population of aqueous droplets are assayed to indicate analyte binding to a certain class of reagent, and a second population of aqueous droplets are inserted into the analytic chamber in order to probe details of that class of reagent.

II. Methods Comprising Optical Analysis of Reagent Diffusion

Various methods may be used for optical analysis of the diffusion of the fluorescent construct, which may or may not bind an analyte in a sample.

In some embodiments, the optical method disclosed herein comprises a fluorescence excitation method, including those using ultraviolet (UV) light to provide simple UV illumination, structured UV illumination, standing wave, and/or pulsed/polarized light. In some embodiments, the optical method disclosed herein comprises using near-IR two-photon fluorescence excitation. For example, high-intensity lasers with brief pulses can be used to provide better precision within scattering samples, and/or less background fluorescence.

In some embodiments, the optical method disclosed herein comprises a fluorescence imaging method. In some instances, a simple CCD with nutating disk is used, where point sources (e.g., quantum dots) are distributed as circles for higher speed, e.g., as illustrated in FIG. 13. In some embodiments, the imaging method disclosed herein comprises Scanned Line Angular Projection Microscopy (SLAPMi), e.g., as disclosed in Kazemipour et al., "Kilohertz frame-rate two-photon tomography," *Nature Methods* 16(8), 778-786 (2019). In some embodiments, the imaging method disclosed herein comprises ghost imaging, e.g., as disclosed in Li et al., "Single-frame wide-field nanoscopy based on ghost imaging via sparsity constraints," *Optica* 6(12), 1515-1523 (2019). In some embodiments, the optical method disclosed herein comprises optical position tracking.

Any suitable combinations of the excitation, imaging and/or optical position tracking methods disclosed herein may be used. During optical measurement, it may be advantageous to switch between two or more optical techniques, to acquire data that the operator requires.

In one aspect, disclosed herein is a method comprising contacting an aqueous sample to be analyzed with an emulsion, wherein the emulsion comprises droplets of water containing fluorescent constructs (e.g., fluorescent particles) that are capable of binding to one or more analyte in the aqueous sample. In some embodiments, the contacting occurs in an analytic chamber which is configured for optical analysis of the fluorescent constructs, including diffusion of the fluorescent constructs prior to and/or after the droplets merge with the aqueous sample. In some embodiments, the analytic chamber is configured to allow the emulsion droplets to merged with the aqueous sample. In some embodiments, fluorescence excitation light is applied with a controlled phase angle. In some embodiments, characteristics of the fluorescence are measured to provide concentration and binding interaction data for various analytes, which can provide useful information about biological samples.

Figure 14:
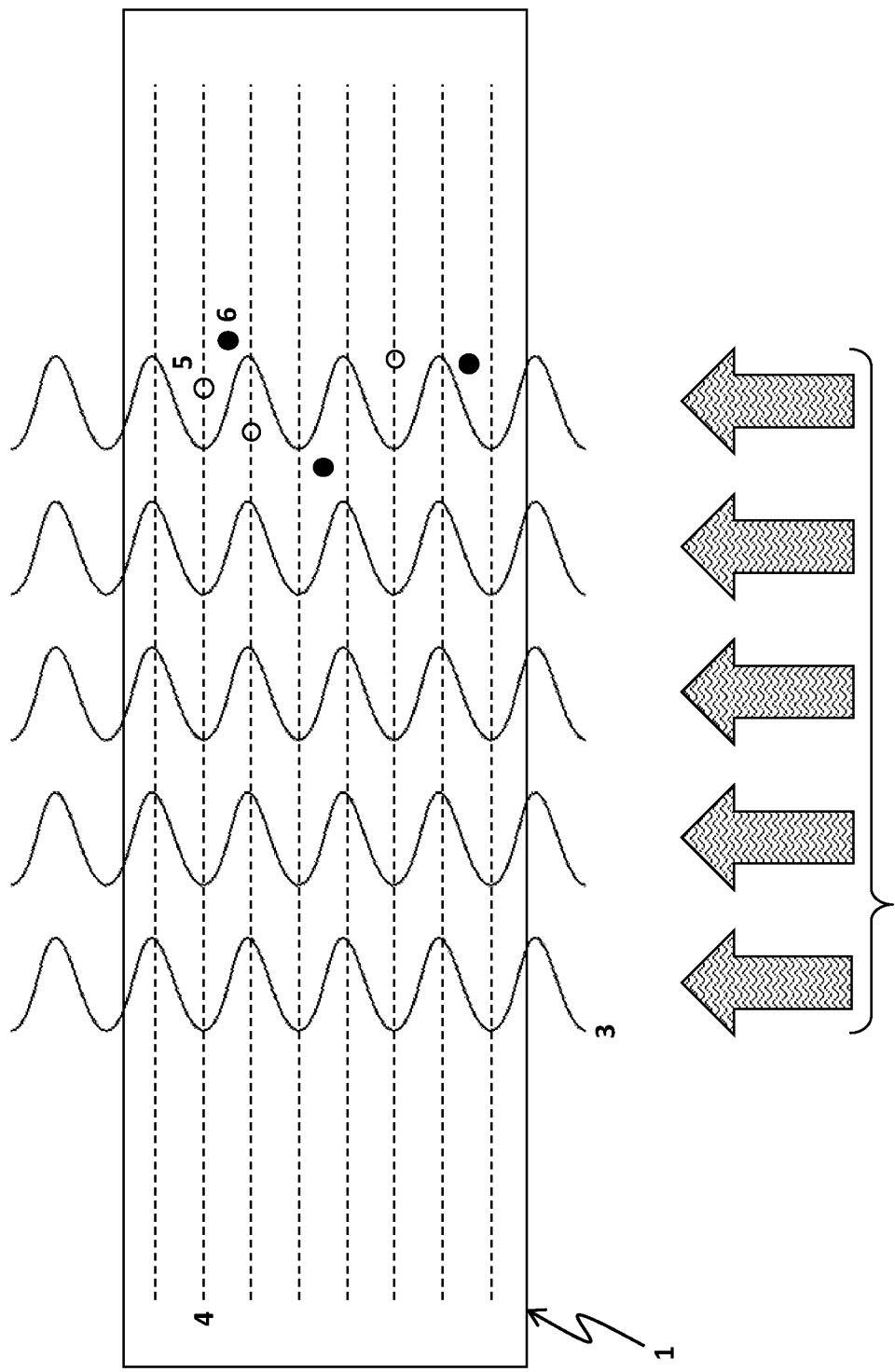
FIG. 14 is a schematic of an exemplary coherent fluorescence excitation light passing through an analytic chamber.
Figure 15:
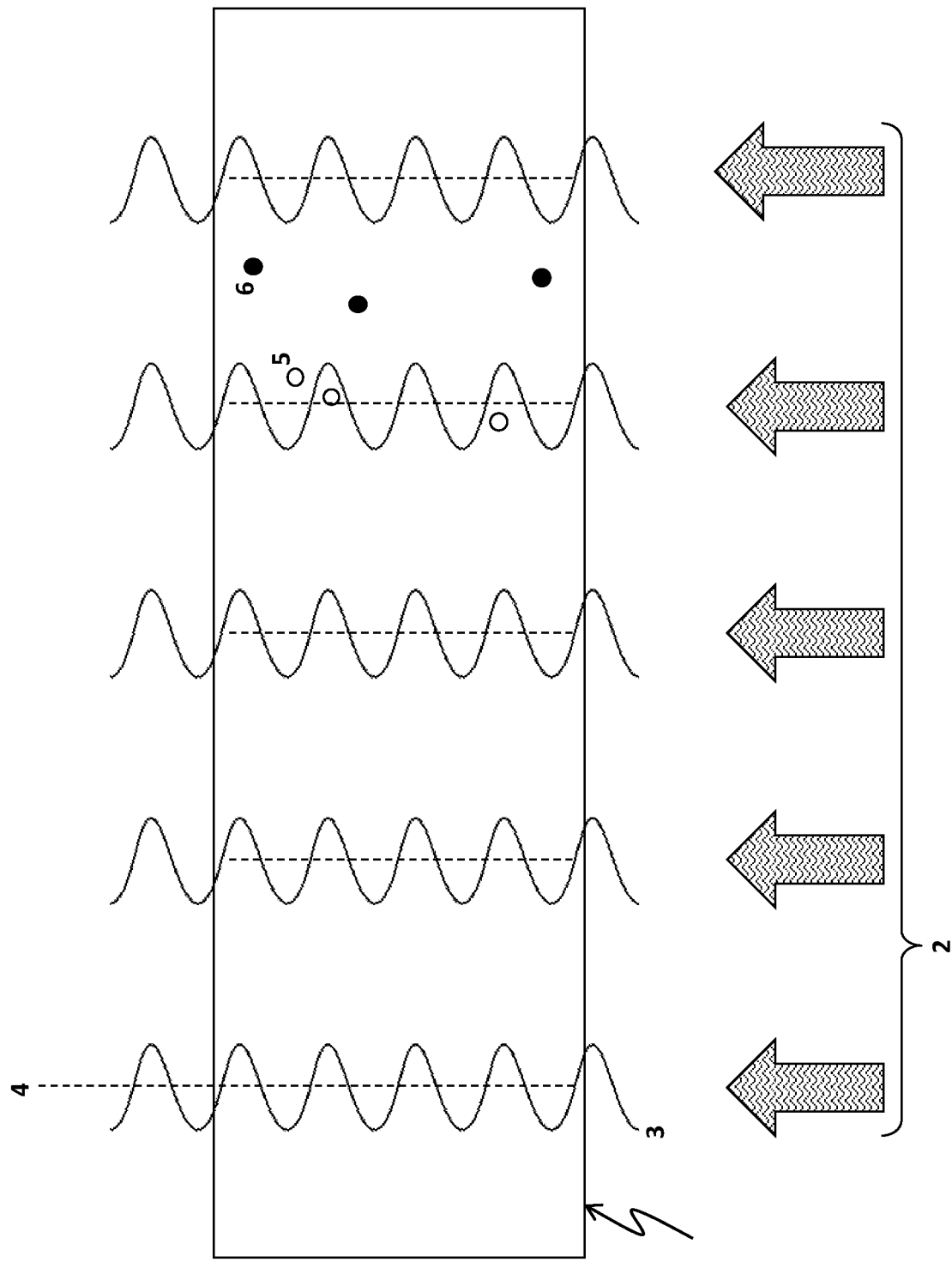
FIG. 15 is a schematic of an exemplary spatially patterned fluorescence excitation light passing through an analytic chamber.

In some embodiments, the fluorescence excitation light is or comprises a standing wave, where the crests and troughs of the light waves form a series of parallel planes of equal electric field magnitude, spaced apart by one wavelength. In some embodiments, the fluorescence excitation light is directed perpendicularly through the analytic chamber, and the analytic chamber contains a plurality of parallel planes of equal electric field magnitude. For example, as shown in FIG. 14, coherent fluorescence excitation light 2 is directed through an analytic chamber 1, yielding a set of planes 4 of maximum electric field magnitude, since each photon wave 3 is in phase with all the other photon waves.

A standing wave of fluorescence excitation light may be generated by coherent light from a laser, within a resonant cavity. Alternatively, a single plane of electric field may be generated by an evanescent wave at a surface of the analytic chamber. If analytic chamber 1 contains fluorescent particles, then those particles 6 that are at or near the parallel planes will maximally fluoresce, and those particles 5 that are between the planes (at a wave node) will minimally fluorescence. Without being bound to any particular theory, the fluorescence intensity of a fluorescent particle is dependent on the magnitude of its local electric field. In some embodiments, the fluorescent particles diffuse stochastically over time, travelling in and out of the parallel planes. As they do so, their fluorescence intensities exhibit corresponding changes. The fluorescence intensity of each fluorescent particle thereby provides an optically-detected signal that characterizes the diffusion behavior of the fluorescent particle.

In some embodiments, the fluorescence color of each particle, along with the fluorescence colors of its neighbors are used to identify the analyte binding reagent that is on the surface of each fluorescent particle. In some embodiments, a fluorescent particle and its neighboring fluorescent particles are traced back to the same emulsion droplet, which can be uniquely identified among the plurality of emulsion droplets, and the identity of the emulsion droplet indicates the identity of the analyte binding reagent associated with each fluorescent particle.

In some embodiments, upon an analyte binding reagent binding to an analyte in the sample, the fluorescent particle exhibits altered diffusion characteristics that affect the optically-detected signal. In some embodiments, monitoring the fluorescence intensity of each fluorescent particle over time provides a measurement of the binding interactions that occur.

In some embodiments, the phase angle of the coherent fluorescence excitation light is moved during the assay, resulting in the parallel planes moving through the analytic chamber. In this case, the parallel planes would be moving past the fluorescent particles in addition to the fluorescent particles moving past the parallel planes. Moving of the phase angle of the coherent fluorescence excitation light may be accomplished by one or more mechanisms. For example, by physically changing the distance between the fluorescence excitation light source and the analytic chamber, use of interferometry, changing the composition of the medium separating the fluorescence excitation light source and the analytic chamber, by use of elliptically-polarized fluorescence excitation light, or by mixing coherent fluorescence excitation light of two or more wavelengths to form a beat frequency.

In some embodiments, the controlled movement of the phase angle provides measurement advantages. For example, it may provide an increased measurement speed for rapid detection. It may produce an oscillation of known frequency for the fluorescence intensity that may be used to distinguish against a fluorescence background of the sample.

In another aspect, disclosed herein is a method comprising contacting an aqueous sample to be analyzed with an emulsion, wherein the emulsion comprises droplets of water containing fluorescent constructs (e.g., fluorescent particles) that are capable of binding to one or more analyte in the aqueous sample. In some embodiments, the contacting occurs in an analytic chamber which is configured for optical analysis of the fluorescent constructs, including diffusion of the fluorescent constructs prior to and/or after the droplets merge with the aqueous sample. In some embodiments, the analytic chamber is configured to allow the emulsion droplets to merged with the aqueous sample. In some embodiments, fluorescence excitation light is applied with a controlled spatial pattern. In some embodiments, characteristics of the fluorescence are measured to provide concentration and binding interaction data for various analytes, which can provide useful information about biological samples.

In some embodiments, the fluorescence excitation light is formed into a spatial pattern, where the light waves form a series of regions of equal electric field magnitude. If such fluorescence excitation light is directed perpendicularly through the analytic chamber, then the analytic chamber will contain this pattern of equal electric field magnitude. For example, as shown in FIG. 9, spatially patterned fluorescence excitation light 2 is directed through an analytic chamber 1, yielding a set of regions 4 of maximum electric field magnitude. Without being bound to any particular theory, the fluorescence intensity of a fluorescent particle is dependent on the magnitude of its local electric field. In analytic chamber 1 which contains fluorescent particles, fluorescent particles 6 that are at or near regions 4 will fluoresce, and those particles 5 that are between the regions will not fluorescence.

Spatially patterned fluorescence excitation light may be generated by using structured light, wherein a pattern is projected through the analytic chamber. The pattern may be produced by a mask, a MicroElectroMechanical System (MEMS), or a Digital Micromirror Device (DMD). The pattern may consist of a grid, a set of lines, a set of spots, or any geometric array that is useful for obtaining the optical measurements.

The spatially patterned fluorescence excitation light may be rotated by a rotating polarizer, to generate rotating polarized light. The edges of the pattern will thereby vary in magnitude of the electric field vector, with a corresponding variation in the fluorescence emission intensity of the fluorescent particles that are at the edges.

In some embodiments, the fluorescent particles diffuse stochastically over time, travelling in and out of the regions. As they do so, their fluorescence intensities exhibit corresponding changes. The fluorescence intensity of each fluorescent particle thereby provides an optically-detected signal that characterizes the diffusion behavior of the fluorescent particle. The fluorescence color of each particle, along with the fluorescence colors of its neighbors, may be used to identify the analyte binding reagent that is on the surface of each fluorescent particle. If an analyte binding reagent binds to an analyte in the sample, then that fluorescent particle will have altered diffusion characteristics that affect the optically-detected signal. Monitoring the fluorescence intensity of each fluorescent particle over time thereby provides a measurement of the binding interactions that occur.

In some embodiments, the regions of the fluorescence excitation light are moved during the assay, resulting in regions moving through the analytic chamber. In this case, the regions would be moving past the fluorescent particles in addition to the fluorescent particles moving past the regions. Moving of the regions may be accomplished by one or more mechanisms. For example, by mechanical control over the position of a mask, or by electronic control of a MEMS or DMD. Another example is rapidly scanning a point across an area, such as is used in confocal microscopy, with the use of rotating reflectors or refractors. Yet another example is changing the angle of the fluorescent excitation light passing through the analytical chamber, with the use of rotating reflectors of refractors.

In some embodiments, specific fluorescent particles are actively tracked by electronic control of a MEMS or DMD. The optically-determined position of a fluorescent particle may be used to ensure that only the area at or around the fluorescent particle is illuminated. This can allow higher illumination intensities that would otherwise overheat the analytic chamber.

In some embodiments, specific fluorescent particles are actively controlled by optical tweezers. This may be accomplished by focusing a laser beam such that its focal point is at or near a fluorescent particle. If the fluorescent particle is dielectric, it will be drawn into the focal point of the laser beam, where the electric field is strongest. Also, photon momenta involved in the excitation and fluorescence processes will be transferred to the fluorescent particle, affecting its movement.

Optical techniques that are commonly used in the field of microscopy may be used to improve the position information about each fluorescent particle. For example, confocal microscopy, structured illumination microscopy, and stochastic optical reconstruction microscopy are techniques that improve image resolution.

In some embodiments, controlled movement of the regions provides measurement advantages. For example, it may provide an increased measurement speed that may have usefulness for detection. In addition, it may produce an oscillation of known frequency for the fluorescence intensity that may be used to distinguish against a fluorescence background of the sample.

III. Compositions and Formulations

In particular embodiments, provided herein are compositions and formulations of emulsion droplets and/or gel beads. For example, emulsions of aqueous droplets within water-immiscible matrices are formulated with varying compositions. The aqueous droplets may contain quantum dots or other fluorescent particles, magnetic particles, dissolved electrolytes or other small molecules, proteins or other large molecules, and surfactants. In other examples, gel beads within aqueous matrices are formulated with varying compositions. The gel beads may contain quantum dots or other fluorescent particles, magnetic particles, and proteins or other large molecules. The gel that forms the beads may be designed to be removed by melting or enzymatic depolymerization.

In some embodiments, a monochrome population of quantum dots is chemically treated such that the surfaces of the quantum dots are coated (derivatized) with a reagent such as a specific protein. This process is repeated with other monochrome populations of quantum dots and other proteins, yielding a large collection of quantum dot populations. For example, there may be 100 vials of red-emitting quantum dots, each coated with a unique protein, plus 100 vials of yellow-emitting quantum dots, each coated with a unique protein, and so on for a variety of quantum dot colors. In some embodiments, this may be performed within a microfluidic device.

In some embodiments, an aliquot of a particular vial of red-emitting quantum dots is mixed with a different-sized aliquot of a particular vial of yellow-emitting quantum dots to generate an aqueous mixture with a known ratio of red-emitting and yellow-emitting quantum dots, each color type with a known protein coating its surface. In some embodiments, this may be performed within a microfluidic device.

In some embodiments, an emulsion is formed using known methods by combining a slow flow of the aqueous mixture with a fast flow of water-immiscible composition (e.g., a water-immiscible medium) within a flow cell. In some embodiments, this method generates aqueous droplets having a highly uniform size within a water-immiscible host matrix.

Figure 16:
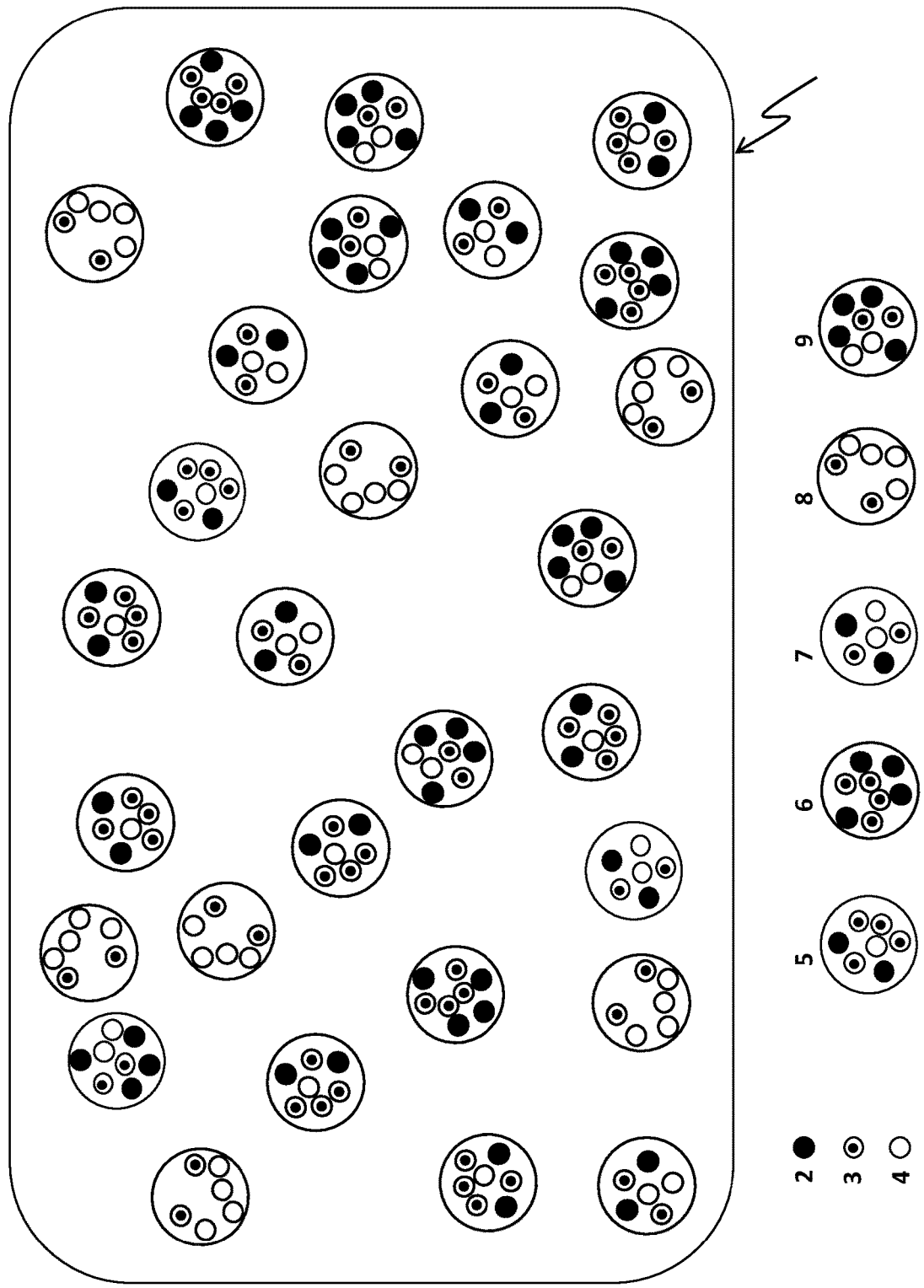
FIG. 16 is a schematic of an exemplary vial of aqueous droplets, containing 5 different formulations of aqueous droplets.
Figure 17:
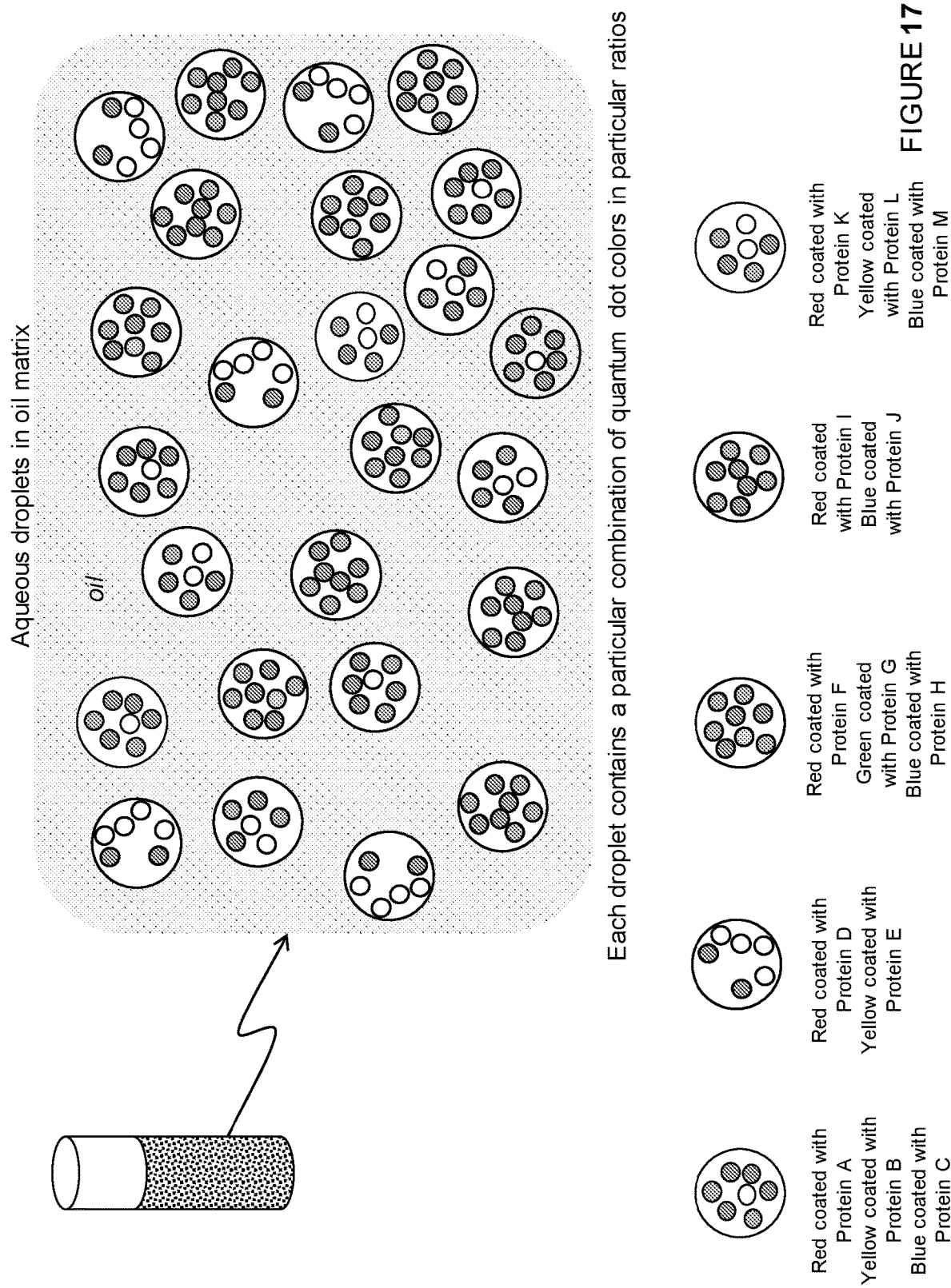
FIG. 17 is a schematic of an exemplary vial of reagent emulsions comprising aqueous droplets in oil matrix, where each droplet contains a particular combination of quantum dot colors in particular ratios.

In some embodiments, the resulting emulsion contains droplets having a known ratio of quantum dots emitting a first color (e.g., red) and quantum dots emitting a second color (e.g., yellow), each color type with a known protein coating its surface. Exemplary emulsion droplet compositions are shown in FIG. 16 and FIG. 17.

In some embodiments, emulsion contains droplets having a known ratio of quantum dots emitting different colors is prepared using a preparatory chamber disclosed herein, for example, as shown in FIG. 21 and described in Example 13. In some embodiments, separate populations of emulsion droplets with defined quantum dot contents are produced in parallel, and may be combined in any suitable ratio, for example, for use in an analytical chamber as disclosed herein.

In some embodiments, gel beads are formed by adding gel beads to the aqueous mixture and then adding an organic solvent to cause swelling of the gel bead. This allows the quantum dots to migrate into the gel beads. Subsequent removal of the organic solvent reduces the swelling and traps the quantum dots within the gel beads.

In some embodiments, the resulting gel beads have a known ratio of quantum dots emitting a first color (e.g., red) and quantum dots emitting a second color (e.g., yellow), each color type with a known protein coating its surface.

Methods of using aqueous emulsions to contain an aqueous sample as a droplet and transport it to measurement apparatus are known in the art and may be used in the present disclosure. Exemplary methods for emulsions are described in WO2002/068104, U.S. Pat. Nos. 7,268,167, 7,772,287, 7,717,615, and 7,375,140, WO2005/089921, and U.S. Pat. No. 8,741,192, all of which are incorporated herein by reference in their entireties for all purposes. Exemplary methods for gel beads are described in U.S. Pat. Nos. 7,645,868, 8,624,014, 7,718,262, 8,283,037, 8,568,881, 8,968,874, 9,376,613, and foreign counterparts thereof, all of which are incorporated herein by reference in their entireties for all purposes. Certain art methods are non-specific regarding the composition of emulsions or gel beads. For example, in those methods, the non-specific emulsions or gel beads cannot be distinguished from each other, e.g., by uniquely identifiable address tags or bar codes. Thus, there is need for formulations that provide new functionality that is not present with general, non-specific formulations.

In some embodiments, the designs described herein are applicable to specific formulations of aqueous droplets (and gel beads) that contain reagents identified within a large address space, where the reagents may be used for detecting analytes in disease marker diagnostics, discovery of the disease markers, discovery of drug therapies, and evaluation of drug therapies. The address space is made large by a combination of distinctive fluorescence emission colors of fluorescent particles along with distinctive counts of those particles, effectively multiplying the size of the address space. Attached to the fluorescent particles are the reagents that are used to detect the analytes. Continuous optical tracking of the individual fluorescent particles allows mapping fluorescent particle behavior to its identification.

A large population of disparate aqueous droplets (or gel beads) may be contained within a small vial and used directly within an analytical apparatus simultaneously. The large address space allows unambiguous mapping despite the presence of disparate reagents on fluorescent particles of the same color. This library of reagents within a vial may be manufactured, stored, and dispensed as needed.

For example, within a vial of aqueous droplets, a sub-population X of the aqueous droplets may contain approximately 6 red-emitting fluorescent particles (coated with Reagent A), 9 green-emitting fluorescent particles (coated with Reagent B), and 3 blue-emitting fluorescent particles (coated with Reagent C).

Another sub-population Y of the aqueous droplets may contain approximately 6 red-emitting fluorescent particles (coated with Reagent D), 12 yellow-emitting fluorescent particles (coated with Reagent E), and 3 blue-emitting fluorescent particles (coated with Reagent F).

Yet another sub-population Z of the aqueous droplets may contain approximately 6 red-emitting fluorescent particles (coated with Reagent G), 9 green-emitting fluorescent particles (coated with Reagent H), and 6 blue-emitting fluorescent particles (coated with Reagent I).

Ultimately, the vial of aqueous droplets can contain many of these sub-populations. The combination of fluorescence emission color and count provides a large address space that uniquely maps the reagents to their fluorescent particles.

During usage, the aqueous droplets are demulsified, freeing up the internal fluorescent particles to interact with any analytes that may be present in their vicinity.

By optically tracking all fluorescent particles during usage of the vial of aqueous droplets, the identity of every reagent can be maintained. In this example, the vial of aqueous droplets contains droplets having red-emitting fluorescent particles attached with Reagent A, red-emitting fluorescent particles attached with Reagent D, and red-emitting fluorescent particles attached with Reagent G. Unambiguous mapping of the red-emitting fluorescent particles to the specific reagent that is attached to them (either A, D, or G) is achieved by associating each fluorescent particle with its originating droplet, which has a unique combination of fluorescence emission colors and fluorescent particle count. Continuous tracking from the moment of demulsification achieves this association.

The optical behavior of each fluorescent particle during usage provides a signal related to detection of analytes.

Detecting the optical tracks and the optical behaviors together, the signal and the identification of the reagent associated with that signal are measured, allowing characterization of the sample under test.

Such compositions and formulations thereof may find widespread applicability for disease marker diagnostics of complex biological media. Additionally, such designs may also be used for disease marker discovery, drug discovery, and drug evaluation, where the sample is known and less complex. A strong advantage of these designs over existing designs is that the designs disclosed herein are easily scaled to arbitrarily large parallelization without restriction to fixed plate arrays. These designs are also independent of pH or other solution characteristics, can be used with opaque samples, and can use extremely small sample volumes with minimal transport loss.

The designs disclosed herein can be used in methods to detect the presence, absence, or degree of binding interactions between analytes and analyte binding reagents, and to determine the presence, absence or amount (e.g., concentration) of analytes in samples.

These designs are useful in methods for the discovery and characterization of binding interactions between known analytes and known analyte binding reagents, and useful in methods for diagnosing the presence of analytes in biological samples. Current methods for performing these tasks suffer from a variety of deficiencies, such as the speed of analysis, limitation on array size, requirement for large sample volumes, and analyte handling losses. The designs described herein allow methods that address many of these limitations and provide a new way to detect intermolecular interactions and measure analytes of various types, including ones having clinical significance and/or diagnostic relevance. The use of emulsions instead of fixed array plates allows the formation of arrays of arbitrary size, allows the sample volume to be small, and avoids having the sample contact plumbing surfaces that can adsorb analytes. The usage occurs over short timescales during which the binding interaction process can be monitored.

A specific field where these designs would be useful is in biotechnology, for the measurement of protein interactions. There are an extremely large number of proteins used in every biological system, which interact in a complex network that is dependent on many factors. Diseases distort this network, adding or removing components and interaction pathways. An understanding of these systems allows early diagnosis of disease in a subject such as a human patient, and a way to chemically repair the system through drug therapy. The most populous and stable proteins within these systems have been partially studied, but much further study is warranted. The addition of new and more powerful tools, such as methods that use the designs described herein, to the repertoire of medical researchers would deepen the understanding of the protein networks and allow the development of new diagnostics and new drug therapies.

IV. Methods of Use

A specific field where these methods are useful is in biotechnology, for the measurement of protein interactions. There are an extremely large number of proteins used in every biological system, which interact in a complex network that is dependent on many factors. Diseases distort this network, adding or removing components and interaction pathways. An understanding of these systems allows early diagnosis of disease, and a way to chemically repair the system through drug therapy. The most populous and stable proteins within these systems have been partially studied, but much further study is warranted. The addition of new and more powerful tools, such as the methods described herein, to the repertoire of medical researchers would deepen the understanding of the protein networks and allow the development of new diagnostics and new drug therapies.

The methods disclosed herein find widespread applicability for disease marker diagnostics of complex biological media. Additionally, such methods may also be used for disease marker discovery, drug discovery, and drug evaluation, where the sample is known and less complex. A strong advantage of these methods over existing methods is that the methods disclosed herein are easily scaled to arbitrarily large parallelization without restriction to fixed plate arrays. These methods are also independent of pH or other solution characteristics, can be used with opaque samples, and can use extremely small sample volumes with minimal transport loss.

The methods disclosed herein can be used to detect the presence, absence, or degree of binding interactions between analytes and analyte binding reagents, and to determine the presence, absence or amount (e.g., concentration) of analytes in samples.

These methods are useful for the discovery and characterization of binding interactions between known analytes and known analyte binding reagents, and useful for diagnosing the presence of analytes in biological samples. Current methods for performing these tasks suffer from a variety of deficiencies, such as the speed of analysis, limitation on array size, requirement for large sample volumes, and analyte handling losses. The methods described herein address many of these limitations and provide a new way to detect intermolecular interactions and measure analytes of various types, including ones having clinical significance and/or diagnostic relevance. The use of emulsions instead of fixed array plates allows the formation of arrays of arbitrary size, allows the sample volume to be small, and avoids having the sample contact plumbing surfaces that can adsorb analytes. The mixing occurs over short timescales during which the binding interaction process can be monitored.

In some embodiments, methods and compositions disclosed herein are useful for studying synergism between two or more agents. In some aspects, methods and compositions are provided to study druggable targets. Most human protein interactions are currently considered undruggable, including cancer proteins such as KRas and protein degraders such as E3 ubiquitin ligases. Such protein-protein interactions may be assayed using the presently disclosed compositions and methods, e.g., on wide, flat surfaces, by providing an intervening molecule (such as a small molecule or antibody) that may in some variations reduce/disrupt and/or in other variations promote/enhance the protein-protein interactions. In some aspects, methods and compositions are provided to study allosteric interactions, e.g., where protein-protein interactions are disrupted by a small effector molecule at a distal site. In some aspects, methods and compositions are provided for single cell analysis. For example, a single lysed cell may be provided per droplet, where binding with all cell components present in the droplet provides a more realistic measure of interactions. In addition, by looking at individual single cells in a population, a measure of cell population heterogeneity may be provided.

In some embodiments, methods and compositions disclosed herein are useful for protein mapping and/or activity based protein profiling. In some aspects, provided herein is a probe kit comprising dendrimer-coated quantum dots (QD) for protein mapping and/or activity based protein profiling. In some embodiments, the QD-tethered probes comprise flexible moieties that can interact with motifs of various geometries, such as binding/reactive pockets and/or cavities, in a protein. In some embodiments, the methods and compositions disclosed herein are used independent of mass spectrometry. In some embodiments, artificial intelligence may be used to infer possible shapes of a protein and suggest potential design of probes.

In some embodiments, methods and compositions disclosed herein are useful for studying weak interactions. For example, a small molecule in the vicinity of a protein may rapidly bounce between association and dissociation states with the protein, and these transitional interactions may be studied using the methods and compositions disclosed herein.

V. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X". In certain embodiments, "about X" refers to a value of ±25%, ±10%, ±5%, ±2%, ±1%, ±0.1%, or ±0.01% of X.

As used herein, a composition refers to any mixture of two or more products, substances, or compounds, including cells. It may be a solution, a suspension, liquid, powder, a paste, aqueous, non-aqueous or any combination thereof.

As used herein, a "subject" may include a mammal, such as a human or other animal, and typically is human.

In this application, the term "analyte" may include specific components of complex biological media such as blood, and may consist of proteins, small molecules, or nucleic acids. The term "analyte" may also refer to molecular species that are to be measured in terms of concentration, presence, size, or binding interaction characteristics. The term "analyte" may also refer to a bacterium or virus. The term "analyte" may also refer to molecular species that are to be measured in terms concentration, presence, size, or binding interaction characteristics. The term "analyte" may also refer to a bacterium or virus. The term "analyte" may also refer to a molecular species that is bound to the interface between the aqueous droplet and the water-immiscible host matrix, or between the aqueous droplet and an inner water-immiscible droplet of a secondary emulsion. The term "analyte" may also refer to an oligonucleotide or to a cell such as a blood cell or bacterium, which can be detected by imaging methods.

In this application, the term "analyte binding reagents" may include components that bind or interact with analytes, typically with high selectivity and high affinity In this application, the term "particle" refers to a collection of atoms, e.g., that are fluorescent or magnetic, or both. Typically, a particle is a solid that is substantially insoluble in the context in which it is described.

In this application, a "flocculation" comprising droplets refers to the sticking together of more than two droplets, generally into a large amorphous mass.

In this application, the term "electric field vector" may include the electric field component of an evanescent wave near a transition in refractive index.

In this application, the term "stochastic" may include a non-deterministic behavior, and to non-deterministic behavior that contains a degree of deterministic behavior.

In this application, the term "binding interaction" may include a combination of an analyte and a reagent, having a particular association constant and a particular dissociation constant under particular conditions. It may also refer to an interaction between a reagent and a bacterium or virus. Occurrence of a binding interaction may be observed by detection of various signals as described herein.

A "signal" or "measurement signal" as used herein may include any detectable emission or observable change. Examples include a fluorescence emission, a color change, or a change in size or appearance. In each case, the signal can be detected as described herein or using techniques and devices known in the art, such as a CCD, CMOS, camera, and the like.

In this application, the term "electric field vector" may include the electric field component of a photon of excitation light.

In this application, the term "magnetic field vector" may include the magnetic field component of a photon of excitation light.

The terms "fluorescent dye", and "fluorophore" as used herein may include moieties that absorb light energy at a defined excitation wavelength and emit light energy at a different wavelength. In some examples, combinations of fluorophores can be used in accordance with a labeling scheme referred to as "Combinatorial Multicolor Coding", which is described in U.S. Pat. No. 6,632,609 and in Speicher, et al., Nature Genetics, 12:368-375, 1996.

As used herein, "spectrally resolvable" means that the labels (e.g., fluorophores such as quantum dots) may be distinguished on the basis of their spectral characteristics, particularly fluorescence emission wavelength, under conditions of operation. For example, the identity of the one or more fluorophores may be correlated to a distinct wavelength of maximum light emission intensity, or perhaps a ratio of intensities at different wavelengths. The spectral characteristic(s) of a label that is/are used to detect and identify a label is referred to as a "color" herein. It will be appreciated that a label is frequently identified on the basis of a specific spectral characteristic.

In this application, the description of the mechanism of fluorescence by the electric field vector of a photon wave is not exclusive. Other mechanisms by which a photon wave may induce fluorescence of a fluorescent particle are included.

In this application, the term "rotating polarized" may include a light wave that has its polarization plane rotated around the transmission axis. For example, rotating polarized light may be generated by a rotating polarizer.

In this application, the term "stochastic" may include non-deterministic behavior, and to non-deterministic behavior that contains a degree of deterministic behavior.

In this application, the term "nutating" may include motion of an optical element that changes the angle or offsets a light ray by an amount proportional to the motion. For example, a transparent flat disk that has its perpendicular axis rotated around a second axis (sweeping out a conic shape) exhibits nutating motion. Light rays that pass through the disk, parallel to the second axis, will be offset proportional to the nutating motion.

In this application, the term "diffusance" may include the diffusive characteristics of one or more particular particles.

In this application, the terms "fluorocarbon fluid", "chlorocarbon fluid", "bromocarbon fluid" and "iodocarbon fluid" may include liquid halocarbon compounds and include solid halocarbon compounds that can form a fluid or a solution.

The following enumerated embodiments represent selected aspects of the present disclosure. While these are often described as 'comprising' specified features and/or steps, the present disclosure also includes corresponding embodiments 'consisting essentially of' and embodiments 'consisting of' the specified features and/or steps.

VI. Exemplary Embodiments

Among the provided embodiments are:
1. A method to detect the presence of an analyte in a sample, which comprises:
   a. providing a first liquid, wherein the first liquid comprises a portion of the sample;
   b. providing an emulsion of a second liquid that comprises an aqueous droplet in a liquid matrix, wherein the aqueous droplet comprises a collection of fluorescent particles having an analyte binding reagent attached to a set of their surfaces;
   c. contacting the first liquid with the aqueous droplet to form a combination of the first liquid and the second liquid under conditions that allow the first liquid and the second liquid to merge into a single fluid; and
   detecting a signal generated by a binding interaction of the analyte with the analyte binding reagent.
2. The method of embodiment 1, wherein the aqueous droplet comprises a fluorescent label or a fluorescent particle. In some such embodiments, the aqueous droplet(s) comprise a fluorescent particle, such as a quantum dot, fluorescent protein, or fluorescent molecule, or a polymeric particle that contains a quantum dot, fluorescent protein, or fluorescent molecule, and this fluorescent particle is thus present in the aqueous droplet. In some such embodiments, the analyte binding reagent is associated with or bound to the quantum dot.
3. The method of any one of embodiments 1-2, wherein the aqueous droplet is a gel bead.
4. The method of any one of embodiments 1-3, wherein the aqueous droplet is not an emulsion.
5. The method of any one of embodiments 1-4, wherein the liquid matrix is not miscible with water. The first liquid matrix can be selected from lipids, oils, hydrocarbon fluids, fluorocarbon fluids, chlorocarbon fluids, bromocarbon fluids, iodocarbon fluids, silicone fluids, and their mixtures.

6. The method of any one of embodiments 1-5, wherein mixing of the first liquid and the aqueous droplet occurs in an analytic chamber.
7. The method of any one of embodiments 1-6, wherein contacting said first liquid and said aqueous droplet comprises mixing:
   a. adjacent streams of the first liquid and the aqueous droplet; or
   b. transverse streams of the first liquid and the aqueous droplet; or
   c. perpendicular streams of the first liquid and the aqueous droplet; or
   d. oblique streams of the first liquid and the aqueous droplet; or
   e. opposed streams of the first liquid and the aqueous droplet; or
   f. concentric streams of the first liquid and the aqueous droplet.
8. The method of any one of embodiments 1-7, wherein contacting said first liquid and said aqueous droplet comprises mixing streams of the first liquid and the aqueous droplet including at least one demulsifying agent.
9. The method of any one of embodiments 1-8, wherein contacting said first liquid and said aqueous droplet comprises mixing streams of the first liquid and the aqueous droplet including at least one surfactant.
10. The method of any one of embodiments 1-9, wherein contacting said first liquid and said aqueous droplet comprises mixing streams of the first liquid and the aqueous droplet including at least one gelling agent.
11. The method of any one of embodiments 1-10, wherein contacting said first liquid and said aqueous droplet comprises mixing streams of the first liquid and the aqueous droplet including at least one viscosity-enhancing agent.
12. The method of any one of embodiments 1-11, wherein said first liquid may be present in the form of an emulsified droplet within a liquid matrix, as a first emulsion. The liquid matrix can be selected from lipids, oils, hydrocarbon fluids, fluorocarbon fluids, chlorocarbon fluids, bromocarbon fluids, iodocarbon fluids, silicone fluids, and their mixtures.
13. The method of any one of embodiments 1-12, wherein contacting said first liquid and said aqueous droplet comprises merging of the aqueous phases into a merged liquid:
   a. with application of an electric field; or
   b. with use of surfactants of opposite charge for the first liquid and the second emulsion; or
   c. with use of a demulsification agent; or
   d. with no use of demulsification factors; or
   e. with application of heat; or
   f. with application of a gel depolymerization agent.
14. The method of any one of embodiments 1-13, wherein the signal generated by binding of the analyte with the analyte binding reagent in said merged liquid is a fluorescent signal.
15. The method of any one of embodiments 1-14, wherein the signal is induced by excitation light having at least one property selected from the group consisting of:
   a. non-polarized;
   b. linearly polarized;
   c. circularly polarized;
   d. elliptically polarized;
   e. trochoidally polarized;
   f. single wavelength;
   g. multi-wavelength;
   h. non-coherent;
   i. coherent;
   j. continuous;
   k. pulsed;
   l. applied at a single incident angle; and
   m. applied at a set of incidence angles.
16. The method of any one of embodiments 1-15, wherein an external electric field is applied to the merged liquid, in a manner selected from the group consisting of:
   a. a constant electric field in a constant direction
   b. a pulsed electric field in a constant direction
   c. an oscillating electric field in a constant direction
   d. a constant field electric switching between multiple directions
   e. a pulsed electric field switching between multiple directions; and
   f. an oscillating electric field switching between multiple directions, sufficient to cause electrophoretic motion of the particles within the merged liquid.
17. A method for detection of an analyte interacting with an analyte binding reagent, comprising:
   a. providing a first liquid comprising the analyte;
   b. providing an emulsion of a second liquid comprising aqueous reagent droplets within a water-immiscible host matrix, wherein the reagent droplets contain a collection of fluorescent particles having an analyte binding reagent attached to a set of their surfaces;
   c. mixing of the first liquid and the reagent droplets together in an analytic chamber and allowing the first liquid and the reagent droplets to merge into a single fluid;
   d. directing excitation light of controlled phase and wavelength through said analytic chamber after said mixing sufficient to cause fluorescence of the said fluorescent particle, wherein said fluorescence is dependent on fluorescent particle position within the local phase angle of the excitation light;
   e. detecting and/or measuring the magnitude of the fluorescence emission after said mixing process;
   f. determining the identity of each analyte binding reagent present within each reagent droplet from the pattern of fluorescent emission wavelengths in the vicinity of the where each droplet merged with the first liquid; and wherein a change in the stochastic behavior of the magnitude of the fluorescence emission provides an indication of analyte presence, concentration, and/or binding interaction.
18. The method of embodiment 17, wherein the aqueous droplet comprises a fluorescent label or a fluorescent particle. In some such embodiments, the aqueous droplet(s) comprise a fluorescent particle, such as a quantum dot, fluorescent protein, or fluorescent molecule, or a polymeric particle that contains a quantum dot, fluorescent protein, or fluorescent molecule, and this fluorescent particle is thus present in the aqueous droplet. In some such embodiments, the analyte binding reagent is associated with or bound to the quantum dot.
19. The method of any one of embodiments 17-18, wherein the aqueous droplet is a gel bead.
20. The method of any one of embodiments 17-19, wherein the aqueous droplet is not an emulsion.
21. The method of any one of embodiments 17-20, wherein the liquid matrix is not miscible with water. The first liquid matrix can be selected from lipids, oils, hydrocarbon fluids, fluorocarbon fluids, chlorocarbon fluids, bromocarbon fluids, iodocarbon fluids, silicone fluids, and their mixtures.

22. The method of any one of embodiments 17-21, wherein mixing of the first liquid and the aqueous droplet occurs in an analytic chamber.

23. The method of any one of embodiments 17-22, wherein contacting said first liquid and said aqueous droplet comprises mixing:
   a. adjacent streams of the first liquid and the aqueous droplet; or
   b. transverse streams of the first liquid and the aqueous droplet; or
   c. perpendicular streams of the first liquid and the aqueous droplet; or
   d. oblique streams of the first liquid and the aqueous droplet; or
   e. opposed streams of the first liquid and the aqueous droplet; or
   f. concentric streams of the first liquid and the aqueous droplet.

24. The method of any one of embodiments 17-23, wherein contacting said first liquid and said aqueous droplet comprises mixing streams of the first liquid and the aqueous droplet including at least one demulsifying agent.

25. The method of any one of embodiments 17-24, wherein contacting said first liquid and said aqueous droplet comprises mixing streams of the first liquid and the aqueous droplet including at least one surfactant.

26. The method of any one of embodiments 17-25, wherein contacting said first liquid and said aqueous droplet comprises mixing streams of the first liquid and the aqueous droplet including at least one gelling agent.

27. The method of any one of embodiments 17-26, wherein contacting said first liquid and said aqueous droplet comprises mixing streams of the first liquid and the aqueous droplet including at least one viscosity-enhancing agent.

28. The method of any one of embodiments 17-27, wherein said first liquid may be present in the form of an emulsified droplet within a liquid matrix, as a first emulsion. The liquid matrix can be selected from lipids, oils, hydrocarbon fluids, and fluorocarbon fluids, chlorocarbon fluids, bromocarbon fluids, iodocarbon fluids, silicone fluids, and their mixtures.

29. The method of any one of embodiments 17-28, wherein contacting said first liquid and said aqueous droplet comprises merging of the aqueous phases into a merged liquid:
   a. with application of an electric field; or
   b. with use of surfactants of opposite charge for the first liquid and the second emulsion; or
   c. with use of a demulsification agent; or
   d. with no use of demulsification factors; or
   e. with application of heat; or
   f. with application of a gel depolymerization agent.

30. The method of any one of embodiments 17-29, wherein the signal generated by binding of the analyte with the analyte binding reagent in said merged liquid is a fluorescent signal.

31. The method of any one of embodiments 17-30, wherein the signal is induced by excitation light having at least one property selected from the group consisting of:
   a. non-polarized;
   b. linearly polarized;
   c. circularly polarized;
   d. elliptically polarized;
   e. trochoidally polarized;
   f. single wavelength;
   g. multi-wavelength;
   h. non-coherent;
   i. coherent;
   j. continuous;
   k. pulsed;
   l. applied at a single incident angle; and
   m. applied at a set of incidence angles.

32. The method of any one of embodiments 17-31, wherein the phase of coherent excitation light is controlled such that the crests and troughs of the light waves are moved past the fluorescent particles, sufficient to cause a corresponding oscillation in the fluorescence of the fluorescent particles.

33. The method of any one of the embodiments 17-32, wherein the ellipticity of elliptically polarized coherent excitation light is controlled such that the crests and troughs of the light waves move past the fluorescent particles, sufficient to cause a corresponding oscillation in the fluorescence of the fluorescent particles.

34. The method of any one of the embodiments 17-33, wherein a nutating transparent window and/or a rotating prism moves the image of each fluorescent particle across the surface of the optical detector.

35. The method of any one of embodiments 17-34, wherein an external electric field is applied to the merged liquid, in a manner selected from the group consisting of:
   a. a constant electric field in a constant direction
   b. a pulsed electric field in a constant direction
   c. an oscillating electric field in a constant direction
   d. a constant field electric switching between multiple directions
   e. a pulsed electric field switching between multiple directions; and
   f. an oscillating electric field switching between multiple directions, sufficient to cause electrophoretic motion of the particles within the merged liquid.

36. A method for detection of an interaction between an analyte in a sample and an analyte binding reagent, wherein the method comprises:
   a. providing a first liquid comprising the analyte;
   b. providing an emulsion of a second liquid comprising aqueous reagent droplets within a water-immiscible host matrix, wherein the reagent droplets contain a collection of fluorescent particles having an analyte binding reagent attached to a set of their surfaces;
   c. mixing of the first liquid and the reagent droplets together in an analytic chamber and allowing the first liquid and the reagent droplets to merge into a single fluid;
   d. directing excitation light of controlled spatial pattern and wavelength through said analytic chamber after said mixing sufficient to cause fluorescence of the said fluorescent particle, wherein said fluorescence is dependent on fluorescent particle position within the local spatial pattern of the excitation light;

e. detecting and/or measuring the magnitude of the fluorescence emission after said mixing process;
f. determining the identity of each analyte binding reagent present within each reagent droplet from the pattern of fluorescent emission wavelengths in the vicinity of the where each droplet merged with the first liquid; and;
wherein a change in the stochastic behavior of the magnitude of the fluorescence emission provides an indication of analyte presence, concentration, and/or binding interaction.

37. The method of embodiment 36, wherein the aqueous droplet comprises a fluorescent label or a fluorescent particle. In some such embodiments, the aqueous droplet(s) comprise a fluorescent particle, such as a quantum dot, fluorescent protein, or fluorescent molecule, or a polymeric particle that contains a quantum dot, fluorescent protein, or fluorescent molecule, and this fluorescent particle is thus present in the aqueous droplet. In some such embodiments, the analyte binding reagent is associated with or bound to the quantum dot.

38. The method of any one of embodiments 36-37, wherein the aqueous droplet is a gel bead.

39. The method of any one of embodiments 36-38, wherein the aqueous droplet is not an emulsion.

40. The method of any one of embodiments 36-39, wherein the liquid matrix is not miscible with water. The first liquid matrix can be selected from lipids, oils, hydrocarbon fluids, fluorocarbon fluids, chlorocarbon fluids, bromocarbon fluids, iodocarbon fluids, silicone fluids, and their mixtures.

41. The method of any one of embodiments 36-40, wherein mixing of the first liquid and the aqueous droplet occurs in an analytic chamber.

42. The method of any one of embodiments 36-41, wherein contacting said first liquid and said aqueous droplet comprises mixing:
a. adjacent streams of the first liquid and the aqueous droplet; or
b. transverse streams of the first liquid and the aqueous droplet; or
c. perpendicular streams of the first liquid and the aqueous droplet; or
d. oblique streams of the first liquid and the aqueous droplet; or
e. opposed streams of the first liquid and the aqueous droplet; or
f. concentric streams of the first liquid and the aqueous droplet.

43. The method of any one of embodiments 36-42, wherein contacting said first liquid and said aqueous droplet comprises mixing streams of the first liquid and the aqueous droplet including at least one demulsifying agent.

44. The method of any one of embodiments 36-43, wherein contacting said first liquid and said aqueous droplet comprises mixing streams of the first liquid and the aqueous droplet including at least one surfactant.

45. The method of any one of embodiments 36-44, wherein contacting said first liquid and said aqueous droplet comprises mixing streams of the first liquid and the aqueous droplet including at least one gelling agent.

46. The method of any one of embodiments 36-45, wherein contacting said first liquid and said aqueous droplet comprises mixing streams of the first liquid and the aqueous droplet including at least one viscosity-enhancing agent.

47. The method of any one of embodiments 36-46, wherein said first liquid may be present in the form of an emulsified droplet within a liquid matrix, as a first emulsion. The liquid matrix can be selected from lipids, oils, hydrocarbon fluids, fluorocarbon fluids, chlorocarbon fluids, bromocarbon fluids, iodocarbon fluids, silicone fluids, and their mixtures.

48. The method of any one of embodiments 36-47, wherein contacting said first liquid and said aqueous droplet comprises merging of the aqueous phases into a merged liquid:
a. with application of an electric field; or
b. with use of surfactants of opposite charge for the first liquid and the second emulsion; or
c. with use of a demulsification agent; or
d. with no use of demulsification factors; or
e. with application of heat; or
f. with application of a gel depolymerization agent.

49. The method of any one of embodiments 36-48, wherein the signal generated by binding of the analyte with the analyte binding reagent in said merged liquid is a fluorescent signal.

50. The method of any one of embodiments 36-49, wherein the signal is induced by excitation light having at least one property selected from the group consisting of:
a. non-polarized;
b. linearly polarized;
c. circularly polarized;
d. elliptically polarized;
e. trochoidally polarized;
f. single wavelength;
g. multi-wavelength;
h. non-coherent;
i. coherent;
j. continuous;
k. pulsed;
l. applied at a single incident angle; and
m. applied at a set of incidence angles.

51. The method of any one of embodiments 36-50, wherein the excitation light is applied as a patterned spatial array across the analytic chamber such that the light intensity varies for different points within the analytic chamber, sufficient to cause changes in the fluorescence of the fluorescent particles as the fluorescent particles move.

52. The method of any one of the embodiments 36-51, wherein the patterned spatial array of excitation light is moved across the analytic chamber such that the light intensity varies for different points and times within the analytic chamber, sufficient to cause changes in the fluorescence of the fluorescent particles.

53. The method of any one of the embodiments 36-52, wherein a nutating transparent window and/or a rotating prism moves the image of each fluorescent particle across the surface of the optical detector.

54. The method of any one of embodiments 36-53, wherein an external electric field is applied to the merged liquid, in a manner selected from the group consisting of:
a. a constant electric field in a constant direction
b. a pulsed electric field in a constant direction
c. an oscillating electric field in a constant direction
d. a constant field electric switching between multiple directions
e. a pulsed electric field switching between multiple directions; and f. an oscillating electric field switching between multiple directions, sufficient to cause electrophoretic motion of the particles within the merged liquid.

55. A design for formulating a set of aqueous droplets, comprising:
   a. providing a water-immiscible liquid matrix that suspends the aqueous droplets;
   b. formulating each aqueous droplet to contain fluorescent particles having a particular combination of fluorescence emission colors;
   c. formulating each aqueous droplet to contain fluorescent particles having a particular count for each fluorescence emission color;
   d. formulating each fluorescent particle to have zero, one, or more reagents attached to it, wherein the identity of the reagent is specific to the color of its particle and specific to the combination of colors and counts within the aqueous droplet that contains it; and collecting the aqueous droplets into a container for storage.

56. The method of embodiments 55, wherein the liquid matrix is not miscible with water. The first liquid matrix can be selected from lipids, oils, hydrocarbon fluids, fluorocarbon fluids, chlorocarbon fluids, bromocarbon fluids, iodocarbon fluids, silicone fluids, and their mixtures.

57. The method of any one of embodiments 55-56, wherein the liquid matrix is formulated to possess properties selected from the group consisting of:
   a. gel;
   b. glass at low temperatures;
   c. solid at low temperatures;
   d. refractive index matching that of the aqueous droplets it is suspending;
   e. refractive index higher than that of the aqueous droplets it is suspending;
   f. refractive index lower than that of the aqueous droplets it is suspending;
   g. non-Newtonian;
   h. shear-thinning;
   i. shear-thickening;
   j. increased viscosity;
   k. decreased viscosity;
   l. density matching that of the aqueous droplets it is suspending;
   m. density less than that of the aqueous droplets it is suspending;
   n. density greater than that of the aqueous droplets it is suspending.

58. The method of any one of embodiments 55-57, wherein the fluorescent particles may be selected from the group consisting of:
   a. quantum dots;
   b. fluorescent proteins;
   c. fluorescent molecules;
   d. polymeric particles that contain quantum dots, fluorescent proteins, or fluorescent molecules;
   e. fluorescent particles that are each linked through a system of chemical bonds to another fluorescent particle;
   f. fluorescent particles that are each linked through a system of chemical bonds to a magnetic particle.

59. The method of any one of embodiments 55-58, wherein the fluorescent particles may be formulated to have analyte-binding reagents bound to their surfaces.

60. The method of any one of embodiments 55-59, wherein the aqueous droplets may be formulated to contain one or more magnetic particles.

61. The method of any one of embodiments 55-60, wherein the aqueous droplet is stabilized with one or more surfactants.

62. The method of any one of embodiments 55-61, wherein the fluorescent particles may be formulated to be connected via a linkage to another fluorescent particle or magnetic particle.

63. The method of any one of embodiments 55-62, wherein the set of aqueous droplets contain disparate combinations of fluorescent particle emission colors and fluorescent particle counts.

64. A design for formulating a set of gel beads, comprising:
   a. providing an aqueous matrix that suspends the gel beads;
   b. providing a gel matrix that can be removed by physical or chemical means;
   c. formulating each gel bead to contain fluorescent particles having a particular combination of fluorescence emission colors;
   d. formulating each gel bead to contain fluorescent particles having a particular count for each fluorescence emission color;
   e. formulating each fluorescent particle to have zero, one, or more reagents attached to it, wherein the identity of the reagent is specific to the color of its particle and specific to the combination of colors and counts within the gel bead that contains it; and
   collecting the gel beads into a container for storage.

65. The method of embodiment 64, wherein the liquid matrix is not miscible with water. The first liquid matrix can be selected from lipids, oils, hydrocarbon fluids, fluorocarbon fluids, chlorocarbon fluids, bromocarbon fluids, iodocarbon fluids, silicone fluids, and their mixtures.

66. The method of any one of embodiments 64-65, wherein the liquid matrix is formulated to possess properties selected from the group consisting of:
   a. gel;
   b. glass at low temperatures;
   c. solid at low temperatures;
   d. refractive index matching that of the aqueous droplets it is suspending;
   e. refractive index higher than that of the aqueous droplets it is suspending;
   f. refractive index lower than that of the aqueous droplets it is suspending;
   g. non-Newtonian;
   h. shear-thinning;
   i. shear-thickening;
   j. increased viscosity;
   k. decreased viscosity;
   l. density matching that of the aqueous droplets it is suspending;
   m. density less than that of the aqueous droplets it is suspending;
   n. density greater than that of the aqueous droplets it is suspending.

67. The method of any one of embodiments 64-66, wherein the fluorescent particles may be selected from the group consisting of:
   a. quantum dots;
   b. fluorescent proteins;
   c. fluorescent molecules;

d. polymeric particles that contain quantum dots, fluorescent proteins, or fluorescent molecules.
68. The method of any one of embodiments 64-67, wherein the fluorescent particles may be formulated to have analyte-binding reagents bound to their surfaces.
69. The method of any one of embodiments 64-68, wherein the gel beads may be formulated to contain one or more magnetic particles.
70. The method of any one of embodiments 64-69, wherein the fluorescent particles may be formulated to be connected via a linkage to another fluorescent particle or magnetic particle.
71. The method of any one of embodiments 64-70, wherein the gel beads are formulated to have properties selected from the group consisting of:
    a. melting of the gel at elevated temperature;
    b. depolymerization of the gel by enzymes;
    c. depolymerization of the gel by chemical agents;
    d. depolymerization of the gel by light.
72. The method of any one of embodiments 64-71, wherein the set of gel beads contains disparate combinations of fluorescent particle emission colors and fluorescent particle counts.

VII. References

1. Walt et al., U.S. Pat. No. 9,664,667 B2 (priority date April 2012).
2. Gammon et al., "Fine Structure Splitting in the Optical Spectra of Single GaAs Quantum Dots", Phys. Rev. Letters 1996, 76, 3005.
3. Pouya et al., "Single Quantum Dot Imaging of Fluid Flow Near Surfaces", Experiments in Fluids 2005, 39, 784-786.
4. A. Kulesa, et al., "Combinatorial Drug Discovery in Nanoliter Droplets", Proceedings of the National Academy of Sciences, 115 (26) 6685-6690, 26 Jun. 2018.
5. Patent Family WO2002/068104 (including U.S. Pat. Nos. 7,268,167, 7,772,287, 7,717,615, and 7,375,140) and Patent Family WO2005/089921 (including U.S. Pat. No. 8,741,192) of the Japan Science and Technology Agency.
6. S. Hohng and T. Ha: "Near-Complete Suppression of Quantum Dot Blinking in Ambient Conditions", J. Am. Chem. Soc. Comm. 2004, 126, 1324-1325.
7. P. Frantsuzov and R. Marcus: "Explanation of quantum dot blinking without the long-lived trap hypothesis", Phys. Rev. B 2005, 72, 155321.
8. P. Bharadwaj and L. Novotny: "Robustness of Quantum Dot Power-Law Blinking", Nano. Lett. 2011, 11, 2137-2141.
9. F. D. Stefani, et al., "Quantification of phootinduced and spontaneous quantum-dot luminescence blinking", Physical Review B 2005, 72, 125304.
10. Choe, et al., "Real-time Monitoring of Colloidal Nanoparticles using Light Sheet Dark-field Microscopy Combined with Microfluidic Concentration Gradient Generator", Bull. Korean Chem. Soc. 2014, 35, 365.
11. I. V. Fedosov, et al., "Measurements of the Diffusive Coefficient of Nanoparticles by Selective Plane Illumination Microscopy", Optics and Spectroscopy 2009, 107, 846-852.
12. M. Friedrich, et al., "Detection of Single Quantum Dots in Model Systems with Sheet Illumination Spectroscopy", J. Fluoresc. 2018, 27, 29-39.
13. L. Gardini, et al., "3D tracking of single nanoparticles and quantum dots in living cells by out-of-focus imaging with diffraction pattern recognition", Nature Scientific Reports 2015, 5, 16088.
14. J. S. Guasto, P. Huang, and K. S. Breuer: "Statistical particle tracking velocimetry using molecular and quantum dot tracer particles", Exp. Fluids 2006, 41, 869-880.
15. A. S. Karakoti, et al., "Surface functionalization of quantum dots for biological applications", Advances in Colloid and Interface Science, 2015, 215, 28-45.
16. A. M. Keller, et al., "Multicolor Tree-Dimensional Tracking for Single-Molecule Fluorescence Resonance Energy Transfer Measurements", Anal. Chem. 2018, 90, 6109-6115.
17. O. Kovtun, et al.: "Single quantum dot tracking illuminates neuroscience at the nanoscale", Chemical Physics Letters 2018, 706, 741-752.
18. S. Labreque, et al.: "Hyperspectral multiplex single-particle tracking of different receptor subtypes labeled with quantum dots in live neurons", J. Biomed. Opt. 2016, 21, 046008.
19. J. Lee, X. Feng, O. Chen, M. Bawendi, and J. Huang: "Stable, small, specific, low-valency quantum dots for single-molecule imaging", Nanoscale 2018, 10, 4406.
20. H. Li, R. Sadr, and M. Yoda: "Multilayer nano-particle image velocimetry", Experiments in Fluids 2006, 41, 185-194.
21. F. Ma, C-C. Li, and C-Y. Zhang: "Development of quantum dot-based biosensors: principles and applications", J. Mater. Chem. B 2018, 6, 6173.
22. K. Ming, J. Kim, M. J. Biondi, A. Syed, K. Chen, A. Lam, M. Ostrowski, A. Rebbapragada, J. J. Feld, and W. C. W. Chan: "Integrated Quantum Dot Barcode Smartphone Optical Device for Wireless Multiplexed Diagnosis of Infected Patients", ACS Nano 2015, 9, 3060-3074.
23. H. Ranchon, V. Picot, and A. Bancaud: "Metrology of confined flows using wide field nanoparticle velocimetry", Nano Scientific Reports, 2015, 5, 10128.
24. B. S. Schuster, et al., "Particle tracking in drug and gene delivery research: State-of-the-art applications and methods", Advanced Drug Delivery Reviews 2015, 91, 70-91.
25. S. T. Wereley and C. D. Meinhart: "Recent Advances in Micro-Particle Image Velocimetry", Annu. Rev. Fluid Mech. 2010, 42, 557-576.
26. S. J. Williams, C. Park, and S. T. Wereley: "Advances and applications on microfluidic velocimetry techniques", Microfluid Nanofluid 2010, 8, 709-726.
27. Q. Xu, Y. Zhang, B. Tang, and C-Y. Zhang: "Multicolor Quantum Dot-Based Chemical Nose for Rapid and Array-Free Differentiation of Multiple Proteins", Anal. Chem. 2016, 88, 2051-2058.
28. M. U. Zahid, L. Ma, S. J. Lim, and A. M. Smith: "Single quantum dot tracking reveals the impact of nanoparticle surface on intracellular state", Nature Communications 2018, 9, 1830.
29. L-J. Zhang, L. Xia, H-Y. Xie, Z-L. Zhang, and D-W. Pang: "Quantum Dot Based Biotracking and Biodetection", Anal. Chem. 2019, 91, 532-547.
30. S. S. Chou, et al., "Nanoscale Graphene Oxide (nGO) as Artificial Receptors: Implications for Biomolecular Interactions and Sensing", J. Am. Chem. Soc. 2012, 134, 16725-16733.
31. X. Yu, J. Wan, Y. Shan, K. Chen, and X. Han: "A Facile Approach to Fabrication of Bifunctional Magnetic-Optical Fe3O4@ZnS Microspheres", Chem. Mater. 2009, 21, 4892-4898.
32. E. M. Thomas, et al., "Blinking Suppression in Highly Excited CdSe/ZnS Quantum Dots by Electron Transfer under Large Positive Gibbs (Free) Energy Change", ACS Nano 2018, 12, 9, 9060-9069.

33. Zhang, et al., "Se/S Ratio-Dependent Properties and Application of Gradient-Alloyed CdSe1-xSx Quantum Dots: Shell-free Structure, Non-blinking Photoluminescence with Single-Exponential Decay, and Efficient QLEDs", ACS Applied Materials & Interfaces 2019, v. 11, no. 6, pp. 6238-6247.
34. Reid et al., "Chemical Structure, Ensemble and Single-ParticleSpectroscopy of Thick-Shell InP—ZnSe Quantum Dots", Nano. Lett. 2018, 18, 2, 709-716. & Interfaces 2019, v. 11, no. 6, pp. 6238-6247.
35. Kazemipour, et al., "Kilohertz frame-rate two-photon tomography", bioRxiv 28 Jun. 2018.
36. Gu et al., "Electrically controlled mass transport into microfluidic droplets from nanodroplet carriers with application in controlled nanoparticle flow synthesis", Lab on a Chip 2018.
37. Sesen et al., "Droplet control technologies for microfluidic high throughput screening (uHTS)", Lab on a Chip 2017.
38. Anand et al., "Electrocoalescence of a pair of conducting drops in an insulating oil", Journal of Fluid Mechanics 2019.
39. Orlin Velev and Ketan Bhatt, "On-chip micromanipulation and assembly of colloidal particles by electric fields", Soft Matter 2006.
40. Hayat et al., "Fast Active Merging of Microdroplets in Microfluidic Chambers Driven by Photo-Isomerisation of Azobenzene Based Surfactants", Biosensors 2019, 9, 129.
41. W. Li, "Single-frame wide-field nanoscopy based on ghost imaging via sparsity constraints", Optica 2019, 6, 1515.
42. McCarthy et al., "Polarized evanescent waves reveal trochoidal dichroism", PNAS 2020, 117 (28), 16143.
43. Daniel et al., "Innovative molecular-based fluorescent nanoparticles for multicolor single particle tracking in cells", J. Phys. D: Appl. Phys. 49 (2016) 084002.
44. Chen et al., "Characteristic rotational behaviors of rod-shaped cargo revealed by automated five-dimensional single particle tracking", Nature Communications 8 887.
45. Gardini et al., "3D tracking of single nanoparticles and quantum dots in living cells by out-of-focus imaging with diffraction pattern recognition", Scientific Reports 5 (2015) 16088
46. Zhang et al., "Quantum Dot Based Biotracking and Biodetection", Anal. Chem. 91 (2019) 532.
47. Zahid et al., "Single quantum dot tracking reveals the impact of nanoparticle surface on intracellular state", Nature Communications 9 (2018) 1830.
48. Abraham et al., "Limitations of Qdot labeling compared to directly-conjugated probes for single particle tracking of B cell receptor mobility", Scientific Reports 7 (2017) 11379.
49. von Diezmann et al., "Three-Dimensional Localization of Single Molecules for Super-Resolution Imaging and Single-Particle Tracking", Chem. Rev. 117 (2017) 7244.

VIII. Examples

The following examples are included for illustrative purposes only and are not intended to limit the scope of the present disclosure.

Example 1: Methods and Compositions for Disease Marker Detection and/or Analysis A vial of reagent emulsion is selected from cold storage and installed in a benchtop instrument. This reagent emulsion contains various types of aqueous droplets within a fluorocarbon oil. One type (called sub-population X) contains approximately 6 red-emitting quantum dots (coated with Antigen A), 9 green-emitting quantum dots (coated with Antigen B), and 3 blue-emitting quantum dots (coated with Antigen C). Another type (called sub-population Y) contains approximately 6 red-emitting quantum dots (coated with Antigen D), 12 yellow-emitting quantum dots (coated with Antigen E), and 3 blue-emitting quantum dots (coated with Antigen F). Yet another type (called sub-population Z) contains approximately 6 red-emitting quantum dots (coated with Antigen G), 9 green-emitting quantum dots (coated with Antigen H), and 6 blue-emitting quantum dots (coated with Antigen I). The vial may contain thousands of such unique types, and forms a library of antigens that can bind with various disease markers.

A sample of blood plasma is mixed with a weak gelling agent, and also added to the benchtop instrument. This blood plasma needs to be tested for the presence of Antibody A, which binds to Antigen A. Antibody A is a naturally-produced marker for a disease.

The benchtop instrument forms a large droplet of the blood plasma within a fluorocarbon oil, and pumps the droplet into the entrance end of a flat, wide analytical chamber. At the same time, the reagent emulsion is pumped into a flat side of the analytical chamber, through a series of small holes near the entrance end. The reagent emulsion droplets get trapped underneath the large droplet of blood plasma, like small balls underneath a carpet. Fluorocarbon oil is pumped into the entrance end of the analytical chamber, causing the blood plasma sample droplet to be pushed through the analytical chamber and out the distal end. The reagent emulsion droplets get swept along with it, assisted by gravity and the weak gelling agent.

A brief pulse of an electric field causes the thin gap of fluorocarbon oil (between the reagent emulsion droplets and the blood plasma) to be breached, demulsifying the emulsion. The quantum dots within each droplet are now free to diffuse into the blood plasma.

The quantum dots begin their diffusion journey as a tight cluster, having been confined together within a droplet. Slowly, the quantum dots begin to diffuse outward in an expanding constellation.

Eventually, a red-colored quantum dot from a Type X droplet encounters an Antibody A molecule in the blood plasma. A binding interaction occurs, forming a structure of summed size. Antibodies are on the same size scale as quantum dots, in the range of 10 nanometers diameter, so a binding interaction typically doubles the size and more than halve the diffusivity. The other quantum dots do not bind strongly with any molecules present, and so their diffusivities remain constant. Weak binding of quantum dots with non-specifically adsorbed molecules tends to reduce the quantum dot diffusivities. To eliminate or reduce non-specific binding, a high-frequency sound wave is then applied which causes shaking or cavitation of the solution environment around each quantum dot (since quantum dots are significantly denser then water). The Type X—Antibody A structures remain intact, but the weakly-bound non-specific adsorption structures get shaken apart and restore the original diffusivity of their quantum dots. Only the Type X—Antibody A structures have halved diffusivity.

During the demulsification and quantum dot diffusion process, intense infrared light pulses are projected through the analytic chamber, as a set of focal lines similar to that used for Scanned Line Angular Projection Microscopy. Two-photon-stimulated fluorescence emission light is collected by a camera, and a tomography algorithm applied to the optical data to reconstruct the movement of the quantum dots. The use of infrared light means that optical scattering (due to large components within the blood plasma) is reduced or minimized, allowing precise quantum dot localization.

The data on the movement of each quantum dot is analyzed. Each quantum dot exhibits random movement in the x, y, and z directions over time, and the magnitude of the movements is dependent on the diffusivity. Some of the quantum dots are observed to have an initial high diffusivity, but then step to a lower diffusivity later. Other quantum dots maintain a high diffusivity. In this example, only those red quantum dots that track from a Type X droplet (identified by its unique signature of 6 red, 9 green, and 3 blue quantum dots) have that step change in diffusivity, indicative of the presence of Antibody A in the blood plasma sample.

In certain reference methods that measure such binding interactions, it can take 10's of minutes for an Antibody A to bind to an Antigen A. This is due to several factors: 1) the Antigen A is affixed to an immobile surface, so that only the Antibody A is free to diffuse towards the Antigen A, 2) numerous Antibody A molecules must bind to a grouping of affixed Antigen A molecules to provide a signal, and 3) the possibility of some interactions to have slow binding kinetics. Slow binding kinetics may be caused by a complex fit that is improbable for the position and orientation of the randomly-moving molecules. In this example disclosed herein, both Antibody A and Antigen A can diffuse towards each other, one Antibody A attached to a red quantum dot (coated with Antigen A) is sufficient to provide a signal, and there are 6 separate red quantum dots which multiplies the probability of a binding interaction with Antibody A molecules in the sample. Thus, instead of requiring an incubation time of 10's of minutes to allow binding interactions to occur, the incubation time using a method disclosed herein is greatly reduced.

Figure 26:
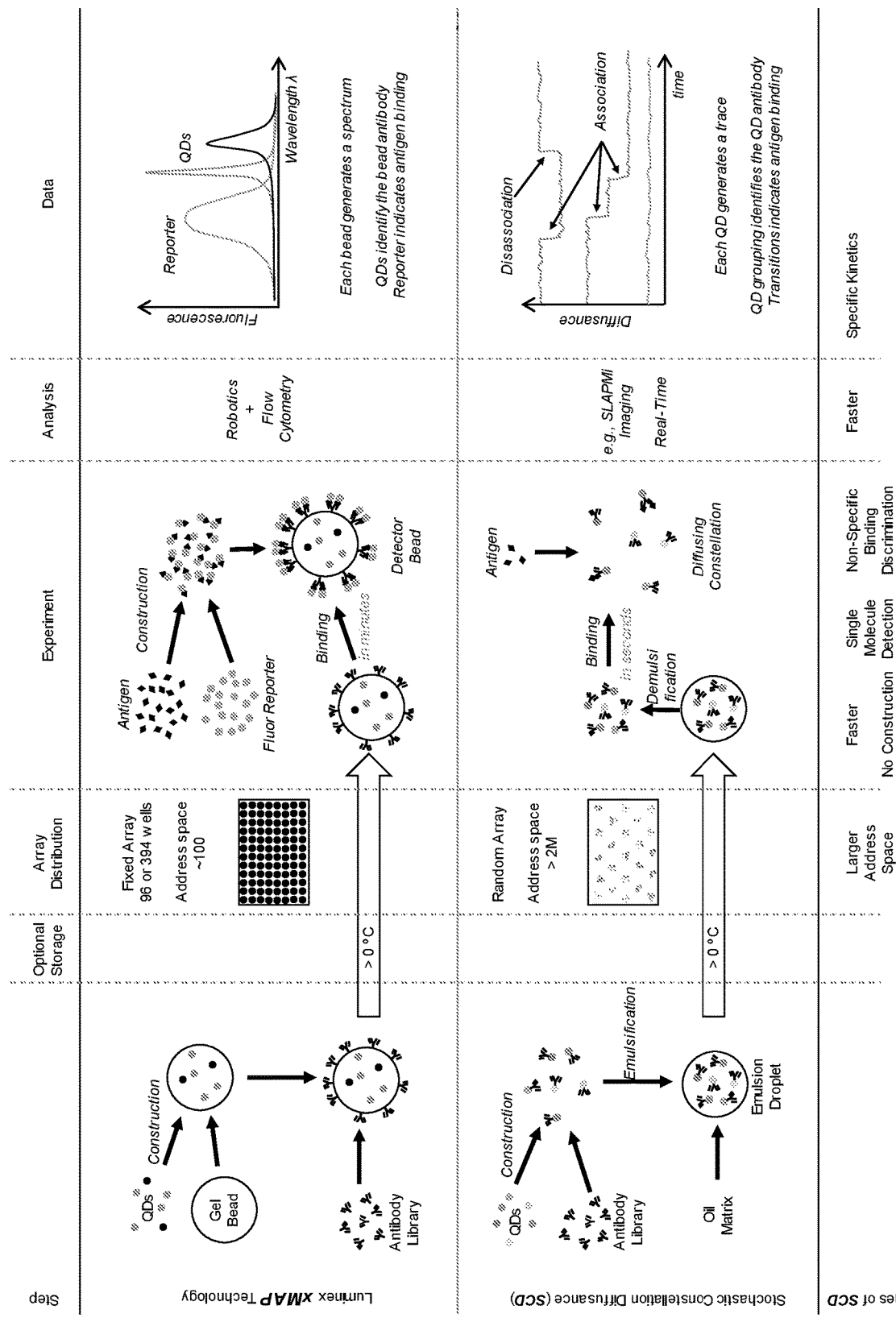
FIG. 26 compares an exemplary method disclosed herein with an existing technology.

The commercial method of Suspension Array Technology (Bio-Rad, Inc.) in the Luminex xMAP Technology uses beads that each has a pattern of fluorescence emission colors and amplitudes to provide identification of each bead, and thereby the identification of the reagent coating on each bead. In this patent application, droplets are used that have a pattern of fluorescence emission colors and amplitudes to provide identification of each droplet. However, there are 4 fundamental differences: 1) the droplets of this example are not coated with reagent, but rather the quantum dots of the droplets are coated with reagent, 2) the droplets are not identified while intact, but rather identified by tracking its component quantum dots over time, 3) the need for washing steps and formation of molecular sandwiches is eliminated in this example, and 4) this example doesn't require the use of a fluorescent ligand to determine the occurrence of binding. Thus, the compositions and methods disclosed in this example, e.g., those based on stochastic constellation diffusance, provide a number of advantages over the Suspension Array Technology, such as a shorter incubation time, no need for washing, no need for the formation of molecular sandwiches, and no need for fluorescent ligands that represent an additional cost, for example, as shown in FIG. 26.

Example 2: Methods and Compositions for Multiplex Marker Detection and/or Analysis Essentially as described in Example 1, the compositions and methods are also used for multiplex including high-throughput marker detection and/or analysis. Instead of only detecting Antibody A in the blood plasma, the sample is tested for the absence/presence, an amount, or an activity of Antibody A through Antibody I, which bind to Antigen A through Antigen I, respectively. Each of Antibody A through Antibody I is a marker for one or more disease or condition.

Specific binding between the antigen and the antibody results in diffusivity that is approximately halved. Because the movement of each quantum dot is tracked and analyzed, quantum dots that form part of a specific antigen/antibody complex exhibit an initial high diffusivity (prior to binding) and then step to a lower diffusivity after binding, and the lower diffusivity is maintained even after reducing or eliminating non-specific adsorption. Quantum dots that do not bind to an antibody maintain a high diffusivity. Diffusivity of quantum dots that only non-specifically bind an antibody may be reduced, but is restored to a high diffusivity after reducing or eliminating non-specific adsorption.

In this example, as long as some quantum dots are traceable to the droplet(s) they are from, multiplex detection and analysis can be performed. For example, observation of the step change in diffusivity of a red quantum dot traced to a Type X droplet (identified by its unique signature of 6 red, 9 green, and 3 blue quantum dots) indicates the presence of Antibody A in the blood plasma sample, while observation of a constant high diffusivity of a green quantum dot traced to a Type X droplet indicates the absence of Antibody B in the sample. Likewise, observation of the step change in diffusivity of a red quantum dot traced to a Type Y droplet (identified by its unique signature of 6 red, 12 yellow, and 3 blue quantum dots) indicates the presence of Antibody D in the blood plasma sample, while observation of a constant high diffusivity of a red quantum dot traced to a Type Z droplet (identified by its unique signature of 6 red, 9 green, and 6 blue quantum dots) indicates the absence of Antibody G in the sample. The amount or concentration of each analyte antibody can also be quantified.

Example 3: Compositions and Methods for Drug Discovery

A vial of reagent emulsion is selected from cold storage, and installed in a benchtop instrument. This reagent emulsion contains various types of aqueous droplets within a fluorocarbon oil. One type (called sub-population X) contains approximately 6 red-emitting quantum dots (coated with Ligand A), 9 green-emitting quantum dots (coated with Ligand B), and 3 blue-emitting quantum dots (coated with Ligand C). Another type (called sub-population Y) contains approximately 6 red-emitting quantum dots (coated with Ligand D), 12 yellow-emitting quantum dots (coated with Ligand E), and 3 blue-emitting quantum dots (coated with Ligand F). Yet another type (called sub-population Z) contains approximately 6 red-emitting quantum dots (coated with Ligand G), 9 green-emitting quantum dots (coated with Ligand H), and 6 blue-emitting quantum dots (coated with Ligand I). The vial may contain thousands of such unique types, and forms a screening library of drug candidates.

A sample of drug target (Receptor R) solution is mixed with a weak gelling agent, and also added to the benchtop instrument. This drug target is tested against a large screening library of drug candidates, e.g., Ligand A through Ligand I, to screen for ligands that specifically target Receptor R.

The benchtop instrument forms a large droplet of the drug target solution within a fluorocarbon oil, and pumps the droplet into the entrance end of a flat, wide analytical chamber. At the same time, the reagent emulsion is pumped into a flat side of the analytical chamber, through a series of small holes near the entrance end. The reagent emulsion droplets get trapped underneath the large droplet of drug target solution, like small balls underneath a carpet. Fluorocarbon oil is pumped into the entrance end of the analytical chamber, causing the drug target solution droplet to be pushed through the analytical chamber and out the distal end. The reagent emulsion droplets get swept along with it, assisted by gravity and the weak gelling agent.

A brief pulse of an electric field causes the thin gap of fluorocarbon oil (between the reagent emulsion droplets and the drug target solution) to be breached, demulsifying the emulsion. The quantum dots within each droplet are now free to diffuse into the drug target solution.

The quantum dots begin their diffusion journey as a tight cluster, having been confined together within a droplet. Slowly, the quantum dots begin to diffuse outward in an expanding constellation.

Eventually, a particular quantum dot encounters a drug target molecule in the drug target solution and a binding interaction occurs, forming a structure of summed size. If the drug target is on the same size scale as quantum dots, in the range of 10 nanometers diameter, then a binding interaction would double the size and more than halve the diffusivity. The other quantum dots would have constant diffusivities.

During the demulsification and quantum dot diffusion process, a pattern of ultraviolet light is projected through the analytic chamber, as a set of closely-spaced parallel beams. Fluorescence emission light is collected by a camera. As the quantum dots randomly diffuse in and out of the parallel beams, their fluorescence correspondingly rises and falls.

The data on the fluorescence intensity of each quantum dot is analyzed. Each quantum dot exhibits random movement in the x, y, and z directions over time, and the magnitude of the movements in the x direction (perpendicular to the parallel beams) is dependent on the diffusivity. Some of the quantum dots are observed to have an initial high diffusivity, but then step to a lower diffusivity later. Other quantum dots maintain a high diffusivity. Tracking the step-changed quantum dots back in time, it may be found, for example, that they all are blue quantum dots that originate from a Type Y droplet (identified by its unique signature of 6 red, 12 yellow, and 3 blue quantum dots). This is indicative that Ligand F has a binding interaction with the drug target, and may be a good candidate for detailed study, as a ligand that targets Receptor R.

Example 4: Compositions and Methods for Unquenching by Abstraction

A vial of quantum dots is synthesized, and installed in a benchtop instrument. These quantum dots are coated with Bromophenol Blue. Red-emitting quantum dots are coated with Bromophenol Blue with a weak bond, yellow-emitting quantum dots are coated with Bromophenol Blue with a medium-strength bond, and blue-emitting quantum dots are coated with Bromophenol Blue with a strong bond. The vial contains millions of such quantum dots. The Bromophenol Blue produces a heavy-atom effect from the presence of bromine atoms, which lowers the fluorescence efficiency of the quantum dots.

A solution of a drug candidate (from a screening library) in free solution is also added to the benchtop instrument.

The benchtop instrument pumps the drug candidate into the entrance end of a flat, wide analytical chamber. At the same time, the quantum dots are pumped into a flat side of the analytical chamber, through a series of small holes near the entrance end. Water is pumped into the entrance end of the analytical chamber, causing the drug candidate and the quantum dots to be pushed through the analytical chamber and out the distal end.

The quantum dots diffuse throughout the solution of drug candidate.

Eventually, a particular quantum dot encounters a drug candidate molecule and a binding interaction occurs, extracting or replacing the Bromophenol Blue from the quantum dot. This unquenches the quantum dot and allows it to fluoresce much brighter.

The data on the fluorescence intensity of each quantum dot is analyzed. Each quantum dot exhibits fluorescence over time. Some of the quantum dots are observed to have an initial low fluorescence, but then step to a higher fluorescence later. Other quantum dots will just maintain a low fluorescence. The step change is indicative that a drug candidate molecule has successfully interacted with that particular quantum dot.

In this example, if the drug candidate has caused the red-emitting and yellow-emitting quantum dots to have increased fluorescence, but not the blue-emitting quantum dots, then this indicates that the drug candidate can displace weakly-bound and medium-strength-bound Bromophenol Blue, but cannot displace the strongly-bound Bromophenol Blue. This provides information on the strength of binding between the drug candidate and the quantum dot surface chemistry that is originally used to bind the Bromophenol Blue.

Example 5: Quencher-Labeled Oligonucleotide

A vial of reagent emulsion is selected from cold storage, and installed in a benchtop instrument. This reagent emulsion contains various types of aqueous droplets within a fluorocarbon oil. One type (called sub-population X) contains approximately 6 red-emitting quantum dots (coated with Oligonucleotide A), 9 green-emitting quantum dots (coated with Oligonucleotide B), and 3 blue-emitting quantum dots (coated with Oligonucleotide C). Another type (called sub-population Y) contains approximately 6 red-emitting quantum dots (coated Oligonucleotide D), 12 yellow-emitting quantum dots (coated with Oligonucleotide E), and 3 blue-emitting quantum dots (coated with Oligonucleotide F). Yet another type (called sub-population Z) contains approximately 6 red-emitting quantum dots (coated with Oligonucleotide G), 9 green-emitting quantum dots (coated with Oligonucleotide H), and 6 blue-emitting quantum dots (coated with Oligonucleotide I). The vial may contain thousands of such unique types, and forms a library of oligonucleotides that can hybridize with various oligonucleotides present in a sample.

DNA fragments are extracted from a collection of cells to produce a sample containing oligonucleotides. These oligonucleotides are labeled with a fluorescence-quenching reagent (such as one containing a heavy atom), and the sample is also added to the benchtop instrument. This sample is tested for the presence of oligonucleotide A* which can hybridize to oligonucleotide A, for example, A* may be a complement of oligonucleotide A.

The benchtop instrument pumps the sample into the entrance end of a flat, wide analytical chamber. At the same time, the reagent emulsion is pumped into a flat side of the analytical chamber, through a series of small holes near the entrance end. The reagent emulsion droplets float on top of the sample. Water is pumped into the entrance end of the analytical chamber, causing the sample to be pushed through the analytical chamber and out the distal end. The reagent emulsion droplets get swept along with it, assisted by gravity.

A brief pulse of an electric field causes demulsification of the emulsion. The quantum dots within each droplet are now free to diffuse into the sample.

The quantum dots begin their diffusion journey as a tight cluster, having been confined together within a droplet. Slowly, the quantum dots begin to diffuse outward in an expanding constellation.

Eventually, a red-colored quantum dot from a Type X droplet encounters an Oligonucleotide A* molecule in the sample. Hybridization between Oligonucleotide A and Oligonucleotide A* occurs, forming a structure with the quencher linked to the quantum dot. In cases of double stranded oligonucleotides, melting and annealing of the oligonucleotides may optionally be used.

The heating and cooling necessary for melting and annealing may be performed by temperature control of the analytic chamber, or by targeted local heating of particular quantum dots using focused light.

During the demulsification and quantum dot diffusion process, ultraviolet light is projected through the analytic chamber, and fluorescence emission light is collected and 2D spectroscopy applied.

The data on the position and fluorescence emission colors of each quantum dot is analyzed. Some quantum dots possess a reduced fluorescence intensity arising from an attached quencher. In this example, only those red quantum dots that track from a Type X droplet (identified by its unique signature of 6 red, 9 green, and 3 blue quantum dots) have that reduced fluorescence intensity, indicative of the presence of Oligonucleotide A*.

Increasing the temperature to cause melting provides additional information on the extent of complementarity between Oligonucleotide A* and Oligonucleotide A, as the melting temperature is indicated by a resumption of the fluorescence intensity.

It is preferable that the quencher is positioned on the end of the sample oligonucleotides that will be closest to the quantum dots.

Optionally, the sample may contain a monomer with a photocatalyst. Application of focused light with appropriate wavelength on particular quantum dots may cause the formation of a gel bead containing the quantum dot. Gel beads thus generated may be separated out by standard methods of gel bead management, such as filtration.

Example 6: Magnetically-Labeled Oligonucleotide

A vial of reagent emulsion is selected from cold storage, and installed in a benchtop instrument. This reagent emulsion contains various types of aqueous droplets within a fluorocarbon oil. One type (called sub-population X) contains approximately 6 red-emitting quantum dots (coated with Oligonucleotide A), 9 green-emitting quantum dots (coated with Oligonucleotide B), and 3 blue-emitting quantum dots (coated with Oligonucleotide C). Another type (called sub-population Y) contains approximately 6 red-emitting quantum dots (coated Oligonucleotide D), 12 yellow-emitting quantum dots (coated with Oligonucleotide E), and 3 blue-emitting quantum dots (coated with Oligonucleotide F). Yet another type (called sub-population Z) contains approximately 6 red-emitting quantum dots (coated with Oligonucleotide G), 9 green-emitting quantum dots (coated with Oligonucleotide H), and 6 blue-emitting quantum dots (coated with Oligonucleotide I). The vial may contain thousands of such unique types, and forms a library of oligonucleotides that can hybridize with various oligonucleotides present in a sample.

DNA fragments are extracted from a collection of cells to produce a sample containing oligonucleotides. These oligonucleotides are labeled with a magnetic particle, and the sample is also added to the benchtop instrument. This sample is tested for the presence of oligonucleotide A* which can hybridize to oligonucleotide A, for example, A* may be a complement of oligonucleotide A.

The benchtop instrument pumps the sample into the entrance end of a flat, wide analytical chamber. At the same time, the reagent emulsion is pumped into a flat side of the analytical chamber, through a series of small holes near the entrance end. The reagent emulsion droplets float on top of the sample. Water is pumped into the entrance end of the analytical chamber, causing the sample to be pushed through the analytical chamber and out the distal end. The reagent emulsion droplets get swept along with it, assisted by gravity.

A brief pulse of an electric field causes demulsification of the emulsion. The quantum dots within each droplet are now free to diffuse into the sample.

The quantum dots begin their diffusion journey as a tight cluster, having been confined together within a droplet. Slowly, the quantum dots begin to diffuse outward in an expanding constellation.

Eventually, a red-colored quantum dot from a Type X droplet encounters an Oligonucleotide A* molecule in the sample. Hybridization between Oligonucleotide A and Oligonucleotide A* occurs, forming a structure with the magnetic particle linked to the quantum dot. In cases of double stranded oligonucleotides, melting and annealing of the oligonucleotides may optionally be used.

During the demulsification and quantum dot diffusion process, a standing wave of ultraviolet light is projected through the analytic chamber, as a set of closely-spaced parallel planes of electric field amplitude. Fluorescence emission light is collected by a camera. As the quantum dots randomly diffuse in and out of the parallel planes, their fluorescence correspondingly rises and falls.

An oscillating magnetic field is applied through the analytic chamber. Those quantum dots that have a linked magnetic particle are pulled in a non-random path through the standing wave of ultraviolet light.

The data on the fluorescence intensity of each quantum dot is analyzed. Each quantum dot exhibits random movement in the x, y, and z directions over time, and the magnitude of the movements in the z direction (perpendicular to the parallel planes) is dependent on the diffusivity and on being magnetically pulled. Some of the quantum dots are observed to have an initial random fluorescence intensity, but then have additional non-random oscillation in the fluorescence intensity later. Other quantum dots maintain random diffusivity. Tracking the step-changed quantum dots back in time, it may be found, for example, that they all are red quantum dots that originate from a Type X droplet (identified by its unique signature of 6 red, 9 green, and 3 blue quantum dots). This is indicative that Oligonucleotide A* is present in the original DNA sample.

Components of the preceding five examples may be used in combination together as appropriate to measurements.

Example 7: Methods and Compositions for Thermal Shift Assay

A stream of emulsion is prepared, and injected into a benchtop instrument. This emulsion contains various types of aqueous droplets within a fluorocarbon oil having the same refractive index as the aqueous droplets. One type (called sub-population X) contains approximately 6 red-emitting quantum dots (coated with drug target Receptor A), 9 green-emitting quantum dots (uncoated), 3 blue-emitting quantum dots (uncoated), and Ligand U in free solution. Another type (called sub-population Y) contains approximately 6 red-emitting quantum dots (coated with Receptor A), 12 yellow-emitting quantum dots (uncoated), 3 blue-emitting quantum dots (uncoated), and Ligand V in free solution. Yet another type (called sub-population Z) contains approximately 6 red-emitting quantum dots (coated with Receptor A), 9 green-emitting quantum dots (uncoated), 6 blue-emitting quantum dots (uncoated), and no ligand in free solution. The vial may contain thousands of such unique types, and forms a screening library, e.g., for drug candidates.

The benchtop instrument pumps the emulsion into the entrance end of a flat, wide analytical chamber. The quantum dots within each aqueous droplet diffuse randomly within the volume of the aqueous droplet. Within some of the aqueous droplets, the ligand in free solution is capable of binding to Receptor A. In some cases, binding of a small ligand has a negligible effect on the diffusive properties of the attached quantum dot.

During the quantum dot diffusion process, ultraviolet light, such as pulses of polarized ultraviolet light, is projected through the analytic chamber. In some cases, an oil (such as perfluorodecalin, RI=1.31) with the same refractive index as the aqueous droplets (RI=1.33) is used. Since the refractive index of the fluorocarbon oil and the aqueous droplets is the same or substantially the same, there is no or little boundary refraction.

Figure 25:
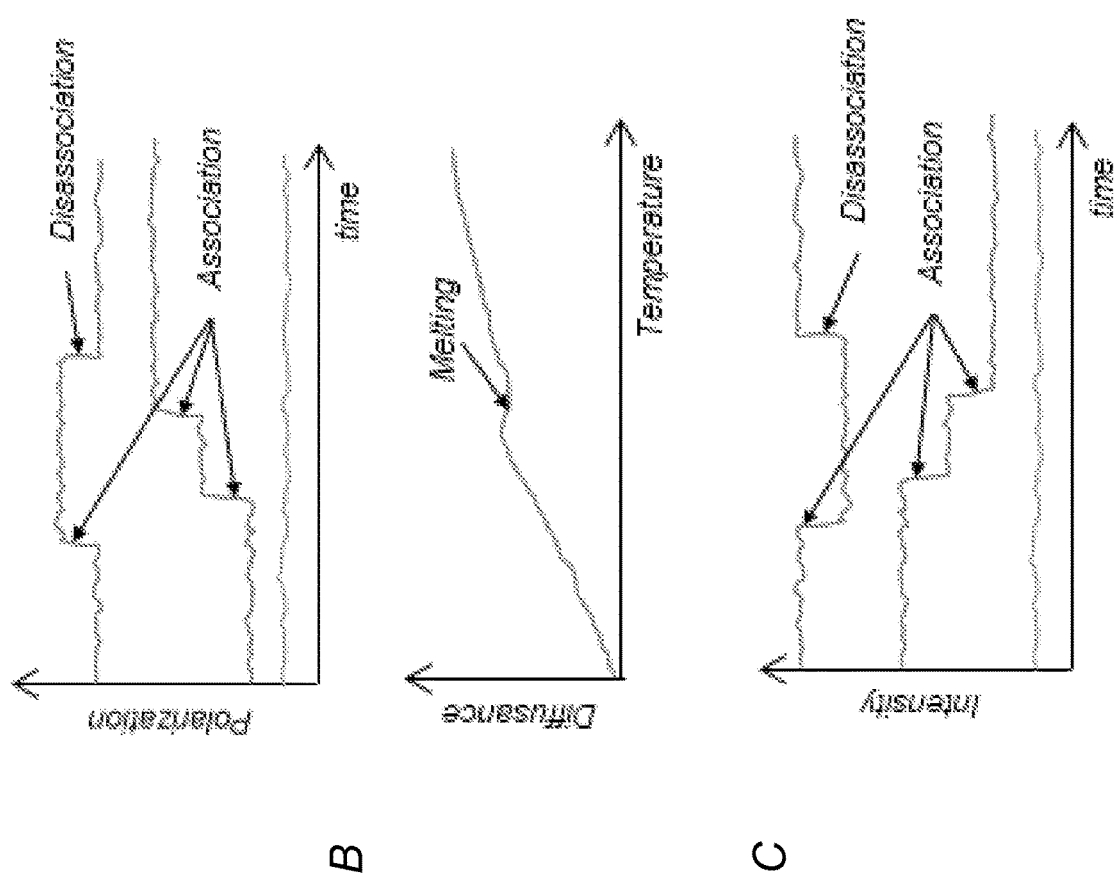
FIG. 25A shows results of an exemplary Fluorescence Polarization Assay (FPA), where unbound quantum dots are rotating rapidly, causing fluorescence emission to have randomized polarization (e.g., association followed by disassociation), while bound quantum dots are rotating slower, causing fluorescence emission to have retained polarization (e.g., association followed by association).
FIG. 25B shows results of an exemplary Thermal Shift Assay, where temperature of an optical chamber can be ramped while observing a quantum dot attached to an analyte such as a protein. Diffusance smoothly rises as the temperature is increased. Once the analyte starts to melt, the smooth rise shows a drop at a particular temperature. Compounds present in the sample can increase the melting temperature, indicating binding of one or more compound to the quantum dot.
FIG. 25C shows results of an exemplary Fluorescence Quenching Assay. A compound containing a heavy atom binds to a quantum dot, quenching the quantum dot fluorescence.

Fluorescence emission light is collected by a camera (or set of cameras), as a collection of fluorescent point sources originating from the quantum dots. The camera records the positions of the fluorescent point sources (and thereby the positions of the quantum dots) as they randomly diffuse within each droplet. The aqueous droplets are of a sufficient size so that the quantum dots are spread apart sufficiently for individual detection. Typically, the separation distance in the focal plane is at least 500 nm. Additionally, the camera records the timing and polarization of the fluorescent point sources. Techniques such as Time Resolved Fluorescence (TRF) are used to only collect fluorescence from a brief window of time after the excitation in order to provide discrimination against background fluorescence of the sample matrix. Techniques such as Fluorescence Polarization Assay (FPA), such as Fluorescence Polarization Immunoassay (FPIA), may be used to collect polarization data to provide information on quantum dot rotational speed. Rapidly spinning (unbound) quantum dots fluoresce with randomized polarization, and slowly spinning (bound) quantum dots fluoresce with a degree of the excitation polarization. For example, as shown in FIG. 25A, pulsed, polarized fluorescence excitation is used to differentiate rapidly spinning (unbound) quantum dots from slowly spinning (bound) quantum dots—unbound quantum dots are rotating rapidly, causing fluorescence emission to have randomized polarization (e.g., association followed by disassociation), while bound quantum dots are rotating slower, causing fluorescence emission to have retained polarization (e.g., association followed by association).

During the quantum dot diffusion process, the temperature of the analytic chamber is slowly raised. The diffusion rate and rotation of the quantum dots increases proportionately to the temperature. Above a particular temperature, the Receptor A begins to melt (unfold). This has a significant effect on the diffusive properties of the attached red quantum dot. Ligand binding in free solution to the Receptor A helps to hold the Receptor A together and increase the melting temperature. Typical Thermal Shift Assays (TSA) require an additional component, a quenchable dye. Measuring diffusion (instead of fluorescence intensity) avoids the need for the quenchable dye.

The data on the fluorescence position and polarization of each quantum dot is analyzed. Each quantum dot exhibits random movement in the x, y, and z directions over time, and the magnitude of the optically-detected movements in the x and y directions are dependent on the diffusivity. Likewise, each quantum dot exhibits random rotation over time, and the speed of the rotations are dependent on the diffusivity. As the temperature is raised, the diffusivity of each quantum dot increases smoothly as a rising slope. However, as the Receptor A begins to melt, the smoothly rising slope exhibits a drop in the diffusivity, marking the melt temperature, for example, as illustrated in FIG. 25B. Tracking the diffusivity versus temperature is used to detect and/or analyze binding interaction(s), e.g., between a ligand and a receptor. In one example, all the red quantum dots within a Type Y droplet (identified by its unique signature of 6 red, 12 yellow, and 3 blue quantum dots) have a melting temperature of 83.3° C., and that all the red quantum dots within a Type Z droplet (identified by its unique signature of 6 red, 9 green, and 6 blue quantum dots) have a melting temperature of 79.8° C. The temperature difference of 3.5° C. is indicative that Ligand V (in free solution inside a Type Y droplet) has a binding interaction with the drug target Receptor A (on red-emitting quantum dots), while a Type Z droplet contains no ligand in free solution and serves as a control, identifying Ligand V as a good candidate for detailed study. In another example, red quantum dots within a Type X droplet (identified by its unique signature of 6 red, 9 green, and 3 blue quantum dots) have a melting temperature of $T_{m1}$, red quantum dots within a Type Y droplet (identified by its unique signature of 6 red, 12 yellow, and 3 blue quantum dots) have a melting temperature of $T_{m2}$, and that red quantum dots within a Type Z droplet (identified by its unique signature of 6 red, 9 green, and 6 blue quantum dots) have a melting temperature of $T_{m3}$. The temperature differences $T_{m1}-T_{m3}$ and $T_{m2}-T_{m3}$ are compared to determine whether Ligand U (in free solution inside a Type X droplet) has a stronger or weaker binding interaction than Ligand V (in free solution inside a Type Y droplet) with the drug target Receptor A.

Example 8: Methods and Compositions for Single Cell Interrogation

A stream of emulsion is prepared, and injected into a benchtop instrument. This emulsion contains various types of aqueous droplets within a fluorocarbon oil having the same refractive index as the aqueous droplets. One type (called sub-population X) contains approximately 6 red-emitting quantum dots (coated with Antibody A), 9 green-emitting quantum dots (coated with Antibody B), 3 blue-emitting quantum dots (coated with Antibody C), a single cell, and lysing enzyme. Another type (called sub-population Y) contains approximately 6 red-emitting quantum dots (coated with Antibody D), 12 yellow-emitting quantum dots (coated with Antibody E), 3 blue-emitting quantum dots (coated with Antibody F), a single cell, and lysing enzyme. Yet another type (called sub-population Z) contains approximately 6 red-emitting quantum dots (coated with Antibody G), 9 green-emitting quantum dots (coated with Antibody H), 6 blue-emitting quantum dots (coated with Antibody I), a single cell, and lysing enzyme. For any sub-population X, Y, or Z droplet, the droplet may be manufactured to comprise a single cell, and then a lysing enzyme is added to the droplet. Alternatively, a droplet may be manufactured to comprise a lysing enzyme, and then a single cell is added to the droplet. The vial may contain thousands of such unique types, and forms a library, e.g., of diagnostic reagents.

The benchtop instrument pumps the emulsion into the entrance end of a flat, wide analytical chamber. The quantum dots within each aqueous droplet diffuse randomly within the volume of the aqueous droplet.

The lysing enzyme ruptures the cell within each droplet, e.g., upon cell/lysing enzyme contact, to release one or more cell component. A particular quantum dot encounters a cell component, and a binding interaction occurs, forming a structure of summed size. For cell component on the same size scale as quantum dots, in the range of 10 nanometers diameter, then a binding interaction doubles the size and more than halve the diffusivity, while quantum dots that do not bind cell components have constant diffusivities.

During the quantum dot diffusion process, ultraviolet light is projected through the analytic chamber. In some cases, an oil (such as perfluorodecalin, RI=1.31) with the same refractive index as the aqueous droplets (RI=1.33) is used. Since the refractive index of the fluorocarbon oil and the aqueous droplets is the same or substantially the same, there is no or little boundary refraction.

Fluorescence emission light is collected by a camera, as a collection of fluorescent point sources originating from the quantum dots. The camera records the positions of the fluorescent point sources (and thereby the positions of the quantum dots) as they randomly diffuse within each droplet. The aqueous droplets are of a sufficient size so that the quantum dots are spread apart sufficiently for individual detection. Typically, the separation distance in the focal plane needs is at least 500 nm. In some cases, this is achieved by flattening the droplets into a pancake shape within the analytic chamber.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots are observed to have an initial high diffusivity, but then step to a lower diffusivity later. Other quantum dots maintain a high diffusivity. Tracking the step-changed quantum dots back in time is used to detect and/or analyze binding interaction(s), e.g., between an antibody and a cell component. In one example, blue quantum dots within a Type Y droplet (identified by its unique signature of 6 red, 12 yellow, and 3 blue quantum dots) have an initial high diffusivity, but then step to a lower diffusivity, indicating that Antibody F on the blue quantum dots has a binding interaction with one or more of the components of the particular cell lysed inside the Type Y droplet. In some instances, each droplet of the Type Y droplets encapsulate a single cell of a cell population, and comparing the behavior of all blue quantum dots within the set of Type Y droplets provides information on the heterogeneity of the cell population.

Example 9: Methods and Compositions for Surfactant Analytes

A stream of emulsion is prepared, and injected into a benchtop instrument. This emulsion contains various types of aqueous droplets within a fluorocarbon oil having the same refractive index as the aqueous droplets. One type (called sub-population X) contains approximately 6 red-emitting quantum dots (coated with drug target Receptor A), 9 green-emitting quantum dots (coated with drug target Receptor B), 3 blue-emitting quantum dots (coated with drug target Receptor C), and surfactant Ligand U adsorbed onto the droplet wall. Another type (called sub-population Y) contains approximately 6 red-emitting quantum dots (coated with Receptor A), 12 yellow-emitting quantum dots (coated with Receptor D), 3 blue-emitting quantum dots (coated with Receptor C), and surfactant Ligand V adsorbed onto the droplet wall. Yet another type (called sub-population Z) contains approximately 6 red-emitting quantum dots (coated with Receptor A), 9 green-emitting quantum dots (coated with Receptor B), 6 blue-emitting quantum dots (coated with Receptor C), and no ligand. The vial may contain thousands of such unique types, and forms a screening library, e.g., of drug candidates.

The benchtop instrument pumps the emulsion into the entrance end of a flat, wide analytical chamber. The quantum dots within each aqueous droplet diffuse randomly within the volume of the aqueous droplet. A particular quantum dot encounters a surfactant ligand molecule at the droplet wall, and the ligand binds to the available receptor. Since the ligand has negligible mobility perpendicular to the wall, this has a substantial effect on the diffusive properties of the attached quantum dot.

Figure 22:
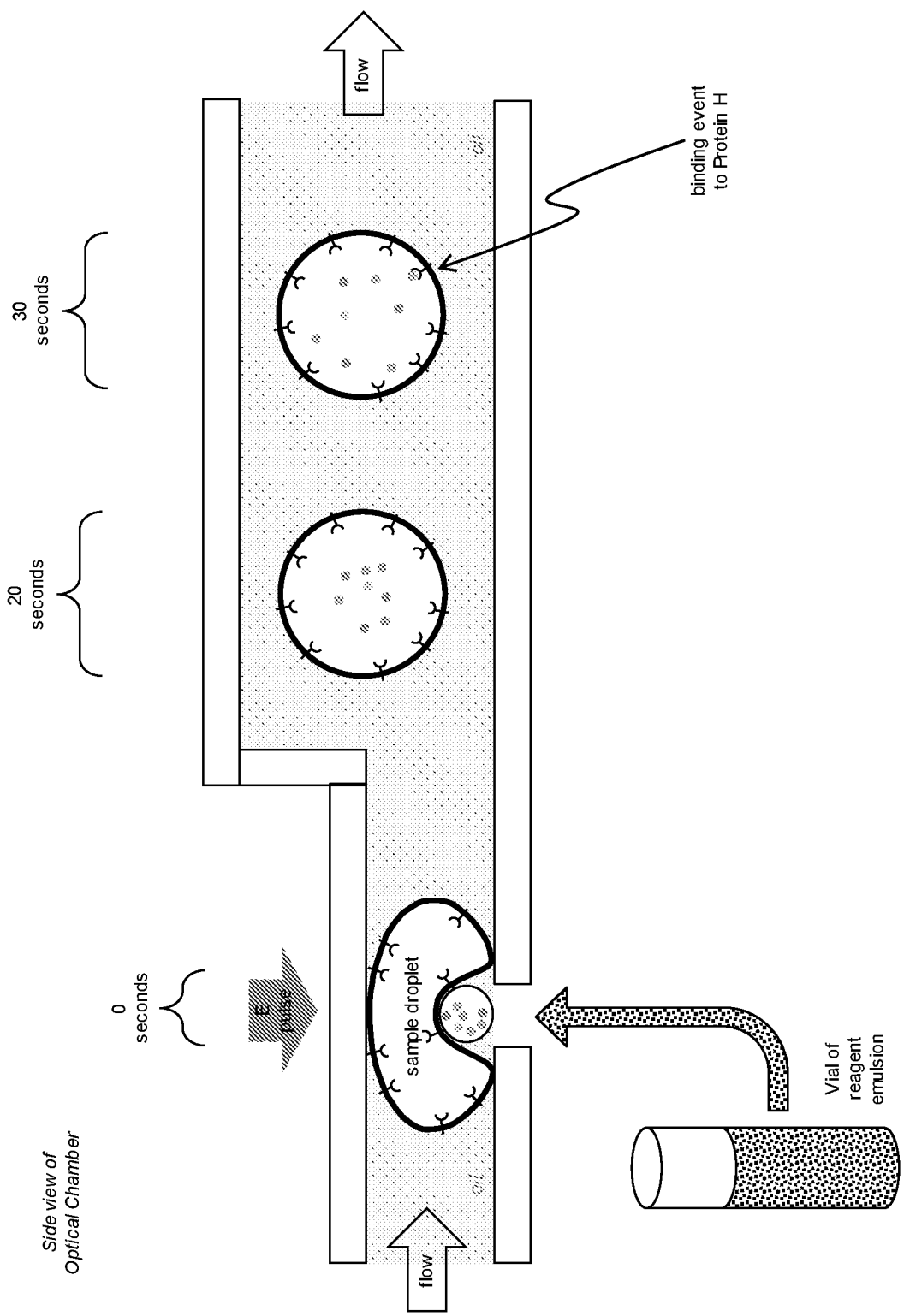
FIG. 22 shows an exemplary method of detecting surfactant analytes, where an emulsion droplet is introduced into a chamber to contact a sample droplet before the droplets are merged using a pulse of electric field.

For example, FIG. 22 shows a sample droplet may be trapped using a narrower channel of an optical chamber, e.g., above an opening through which one or more emulsion droplet may be introduced to contact the sample droplet. A weak pulse of electric field is applied to merge the emulsion droplet with a small sample droplet, allowing the quantum dots to diffuse into the sample droplet. Oil that has same refractive index as the aqueous sample may be used, for example, perfluorodecalin (RI=1.31) and mineral oil may be used. Quantum dots diffuse to walls of the sample droplet and adhere to surfactant analytes on the droplet wall, and the binding event is detected.

Figure 23:
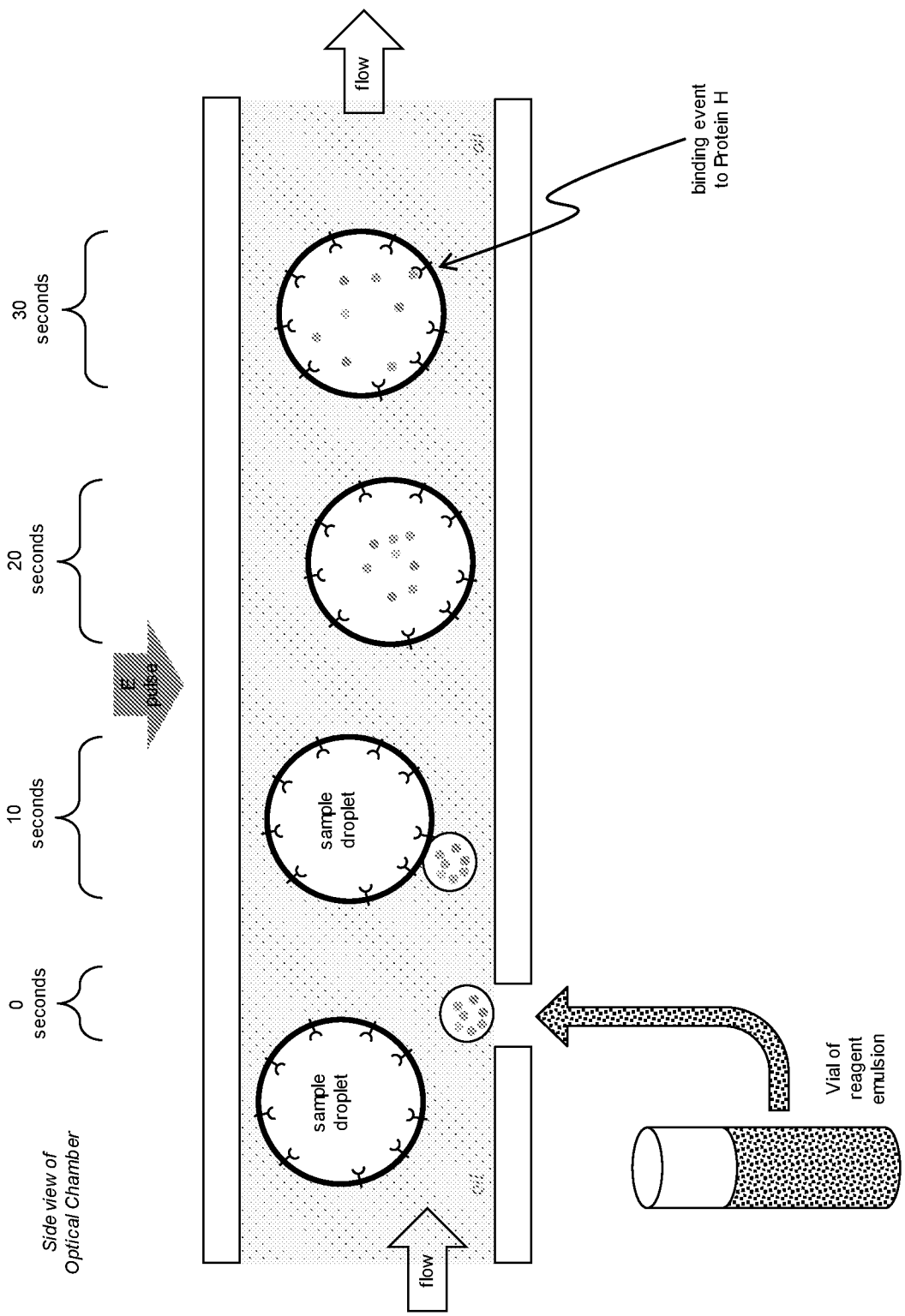
FIG. 23 shows an exemplary method of detecting surfactant analytes, where electrostatic attraction merges the emulsion droplet and the sample droplet.

FIG. 23 shows an emulsion droplet may be introduced into an oil matrix through an opening, and electrostatic attraction merges the emulsion droplet and the sample droplet, allowing the quantum dots to diffuse into the sample droplet. Quantum dots diffuse to walls of the sample droplet and adhere to surfactant analytes on the droplet wall, and the binding event is detected.

During the quantum dot diffusion process, ultraviolet light is projected through the analytic chamber. In some cases, an oil (such as perfluorodecalin, RI=1.31) with the same refractive index as the aqueous droplets (RI=1.33) is used. Since the refractive index of the fluorocarbon oil and the aqueous droplets is the same or substantially the same, there is no or little boundary refraction.

Fluorescence emission light is collected by a camera, as a collection of fluorescent point sources originating from the quantum dots. The camera records the positions of the fluorescent point sources (and thereby the positions of the quantum dots) as they randomly diffuse within each droplet. In some cases, the aqueous droplets are of a sufficient size so that the quantum dots are spread apart sufficiently for individual detection. Typically, the separation distance in the focal plane is at least 500 nm, and may be achieved by flattening the droplets into a pancake shape within the analytic chamber.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots are observed to have an initial high diffusivity, but then step to a lower diffusivity later. Other quantum dots maintain a high diffusivity. Tracking the step-changed quantum dots back in time is used to detect and/or analyze binding interaction(s), e.g., between a receptor and surfactant ligand. In one example, blue quantum dots that originate from a Type Y droplet (identified by its unique signature of 6 red, 12 yellow, and 3 blue quantum dots) have an initial high diffusivity but then step to a lower diffusivity (e.g., while blue quantum dots in a Type X or Type Z do not exhibit the step down to a lower diffusivity), indicating Receptor C has a binding interaction with surfactant Ligand V, and Ligand V may be a good candidate for detailed study.

Example 10: Compositions and Methods for Synergistic or Allotropic Drug Discovery A vial of reagent emulsion is selected from cold storage, and installed in a benchtop instrument. This emulsion contains various types of aqueous droplets within a fluorocarbon oil. One type (called sub-population X) contains approximately 6 red-emitting quantum dots (coated with Antigen A), 9 green-emitting quantum dots (coated with Antigen B), 3 blue-emitting quantum dots (coated with Antigen C), and Ligand U in free solution. Another type (called sub-population Y) contains approximately 6 red-emitting quantum dots (coated with Antigen D), 12 yellow-emitting quantum dots (coated with Antigen E), 3 blue-emitting quantum dots (coated with Antigen F), and Ligand V in free solution. Yet another type (called sub-population Z) contains approximately 6 red-emitting quantum dots (coated with Antigen G), 9 green-emitting quantum dots (coated with Antigen H), 6 blue-emitting quantum dots (coated with Antigen I), and Ligand W in free solution. Antigens A, B, C, D, E, F, G, H, and I are candidates for specific binding to Antibody K. The vial may contain thousands of such unique types, and forms a screening library, e.g., of drug candidates.

A sample of Antibody K solution (optionally mixed with a weak gelling agent) is added to the benchtop instrument. This antibody is tested for synergism or allotropism against a large screening library of drug candidate combinations, e.g., Antigen A through Antigen I with Ligand V through Ligand W, to screen for combinations that produce binding to Antibody K.

The benchtop instrument forms a large droplet of the Antibody K solution within a fluorocarbon oil, and pumps the droplet into the entrance end of a flat, wide analytical chamber. At the same time, the emulsion is pumped into a flat side of the analytical chamber, through a series of small holes near the entrance end. The emulsion droplets get trapped underneath the large droplet of Antibody K solution, like small balls underneath a carpet. Fluorocarbon oil is pumped into the entrance end of the analytical chamber, causing the Antibody K solution droplet to be pushed through the analytical chamber and out the distal end. The emulsion droplets get swept along with it, assisted by gravity and the weak gelling agent.

A brief pulse of an electric field causes the thin gap of fluorocarbon oil (between the emulsion droplets and the Antibody K solution) to be breached, demulsifying the emulsion droplets. The quantum dots within each droplet are now free to diffuse into the Antibody K solution.

The quantum dots begin their diffusion journey as a tight cluster, having been confined together within a droplet. Slowly, the quantum dots begin to diffuse outward in an expanding constellation. Additionally, the various ligands also expand outward, with dropping and overlapping concentrations. This results in each quantum dot experiencing a unique combination of ligands in its immediate environment.

A particular quantum dot encounters an Antibody K molecule in the drug target solution along with an activating ligand, and a binding interaction occurs, forming a structure of summed size. For drug targets on the same size scale as quantum dots, in the range of 10 nanometers diameter, a binding interaction doubles the size and more than halve the diffusivity, while quantum dots that do experience the binding interaction have constant diffusivities.

During the demulsification and quantum dot diffusion process, ultraviolet light is projected through the analytic chamber. Fluorescence emission light is collected by a camera, as a collection of fluorescent point sources originating from the quantum dots. The camera records the positions of the fluorescent point sources (and thereby the positions of the quantum dots) as they randomly diffuse.

The data on the fluorescence position of each quantum dot is analyzed. Each quantum dot exhibits random movement in the x, y, and z directions over time, and the magnitude of the movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it may be found, for example, that blue quantum dots exhibiting the step down in diffusivity originate from a Type Y droplet (identified by its unique signature of 6 red, 12 yellow, and 3 blue quantum dots), and are near a constellation from a Type Z droplet. This is indicative that Antigen F (from the population Y droplet) has a binding interaction with Antibody K in the presence of Ligand W (from the population Z droplet), and the pair Antigen F plus Ligand W may be a good candidate for detailed study, for a synergistic or allosteric interaction with Antibody K. Since the ligands are of known composition, it is straightforward to calculate their diffusivities and thus generate a map of their expected concentrations over time within the analytic chamber. In some examples, a weak gelling agent is added to minimize convection and diffusive rates.

Figure 24:
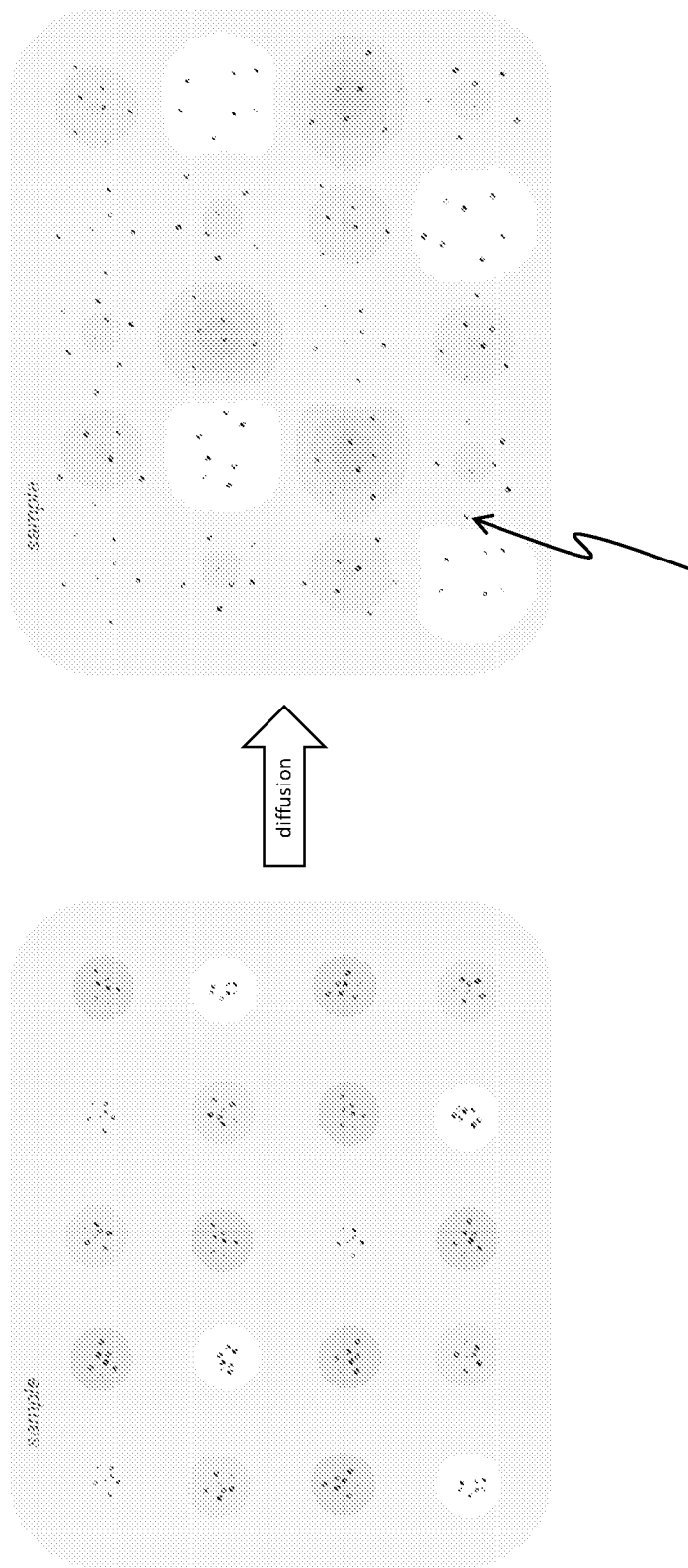
FIG. 24 shows an exemplary method of correlating measured stochastic diffusance behavior of a quantum dot with concentrations of compounds, including molecules in the sample and in the adjacent droplets that have expanded to become overlapping constellations.

For example, as shown in FIG. 24, synergistic molecule combinations may be assayed. Diffusion coefficients are known, therefore the measured stochastic diffusance behavior of the green quantum dot (identified by the arrow) can be correlated to concentrations of compounds, including molecules in the sample and in the adjacent droplets that have expanded to become overlapping constellations.

Example 11: Compositions and Methods for Protein Mapping

A vial of reagent emulsion is selected from cold storage, and installed in a benchtop instrument. This emulsion contains various types of aqueous droplets within a fluorocarbon oil. One type (called sub-population X) contains approximately 6 red-emitting quantum dots (coated with dendrimers tipped with Ligand A), 9 green-emitting quantum dots (coated with dendrimers tipped with Ligand B), and 3 blue-emitting quantum dots (coated with dendrimers tipped with Ligand C). Another type (called sub-population Y) contains approximately 6 red-emitting quantum dots (coated with dendrimers tipped with Ligand D), 12 yellow-emitting quantum dots (coated with dendrimers tipped with Ligand E), and 3 blue-emitting quantum dots (coated with dendrimers tipped with Ligand F). Yet another type (called sub-population Z) contains approximately 6 red-emitting quantum dots (coated with dendrimers tipped with Ligand G), 9 green-emitting quantum dots (coated with dendrimers tipped with Ligand H), and 6 blue-emitting quantum dots (coated with dendrimers tipped with Ligand I). The vial may contain thousands of such unique types, and forms a screening library of protein probes.

The use of dendrimers is useful to reduce or avoid steric hindrance, but is not strictly necessary, since other moieties such as flexible linkers can be used.

A sample of Protein K solution (optionally mixed with a weak gelling agent to control convection or slow down diffusion) is added to the benchtop instrument. This protein is tested for interactions with the ligands, e.g., Ligand A through Ligand I, to map the surface of Protein K.

The benchtop instrument forms a large droplet of the Protein K solution within a fluorocarbon oil, and pumps the droplet into the entrance end of a flat, wide analytical chamber. At the same time, the reagent emulsion is pumped into a flat side of the analytical chamber, through a series of small holes near the entrance end. The emulsion droplets get trapped underneath the large droplet of Protein K solution, like small balls underneath a carpet. Fluorocarbon oil is pumped into the entrance end of the analytical chamber, causing the Protein K solution droplet to be pushed through the analytical chamber and out the distal end. The emulsion droplets get swept along with it, assisted by gravity and the weak gelling agent.

A brief pulse of an electric field causes the thin gap of fluorocarbon oil (between the emulsion droplets and the Protein K solution) to be breached, demulsifying the emulsion droplets. The quantum dots within each droplet are now free to diffuse into the Protein K solution.

The quantum dots begin their diffusion journey as a tight cluster, having been confined together within a droplet. Slowly, the quantum dots begin to diffuse outward in an expanding constellation. Eventually, a particular quantum dot encounters a Protein K molecule in the Protein K solution, and a binding interaction occurs, forming a structure of summed size. For example, if the Protein K is on the same size scale as quantum dots, in the range of 10 nanometers diameter, then a binding interaction would double the size and more than halve the diffusivity. Quantum dots that do not experience the binding interaction have constant diffusivities.

During the demulsification and quantum dot diffusion process, ultraviolet light is projected through the analytic chamber. Fluorescence emission light is collected by a camera, as a collection of fluorescent point sources originating from the quantum dots. The camera records the positions of the fluorescent point sources (and thereby the positions of the quantum dots) as they randomly diffuse.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it is found, for example, that blue quantum dots exhibiting the step down in diffusivity originate from a Type Y droplet (identified by its unique signature of 6 red, 12 yellow, and 3 blue quantum dots). This is indicative that Ligand F has a binding interaction with Protein K. Since the ligand is on the tip of a dendrimer, it has substantial freedom to probe surface features of Protein K without steric hindrance. Both strong (enduring) and weak (brief) interactions are detected and characterized by the timing of the diffusivity step changes. Information about which ligands do and do not interact is combined with the known structure of the ligands to assemble a map of the Protein K surface.

Example 12: Methods and Compositions for Large Droplet Assay

A stream of emulsion is prepared, and injected into a benchtop instrument. This emulsion contains various types of aqueous droplets within a fluorocarbon oil having the same refractive index as the aqueous droplets. One type (called sub-population X) contains approximately 6 red-emitting quantum dots (coated with drug target Receptor A), 9 green-emitting quantum dots (coated with drug target Receptor B), 3 blue-emitting quantum dots (coated with drug target Receptor C), and Ligand U in free solution. Another type (called sub-population Y) contains approximately 6 red-emitting quantum dots (coated with drug target Receptor D), 12 yellow-emitting quantum dots (coated with drug target Receptor E), 3 blue-emitting quantum dots (coated with drug target Receptor F), and Ligand V in free solution. Yet another type (called sub-population Z) contains approximately 6 red-emitting quantum dots (coated with drug target Receptor G), 9 green-emitting quantum dots (coated with drug target Receptor H), 6 blue-emitting quantum dots (coated with drug target Receptor I), and Ligand W in free solution. The vial may contain thousands of such unique types, and forms a screening library of drug candidates.

The benchtop instrument pumps the emulsion into the entrance end of a flat, wide analytical chamber. The quantum dots within each aqueous droplet diffuse randomly within the volume of the aqueous droplet. Eventually, a particular quantum dot encounters a ligand, and a binding interaction occurs, forming a structure of summed size. If the ligand is on the same size scale as quantum dots, in the range of 10 nanometers diameter, then a binding interaction would double the size and more than halve the diffusivity, while quantum dots that do not experience the binding interaction have constant diffusivities.

During the quantum dot diffusion process, ultraviolet light is projected through the analytic chamber. Since the refractive index of the fluorocarbon oil and the aqueous droplets is the same or substantially the same, there is no or little boundary refraction. Fluorescence emission light is collected by a camera, as a collection of fluorescent point sources originating from the quantum dots. The camera records the positions of the fluorescent point sources (and thereby the positions of the quantum dots) as they randomly diffuse within each droplet. In some instances, the aqueous droplets are of a sufficient size so that the quantum dots are spread apart sufficiently for individual detection. Typically, the separation distance in the focal plane is at least 500 nm. This may be achieved by flattening the droplets into a pancake shape within the analytic chamber.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it is found, for example, that blue quantum dots exhibiting the step down in diffusivity originate from a Type Y droplet (identified by its unique signature of 6 red, 12 yellow, and 3 blue quantum dots). This is indicative that Ligand V has a binding interaction with Receptor F, and may be a good candidate for detailed study.

Example 13: Compositions and Methods for Droplet Preparation

A method of generating a controlled composition of emulsion is provided. Also provided is a preparatory chamber and reagents associated with preparing a controlled composition of emulsion. For example, as shown in FIG. 21, a sample of aqueous solution containing a particular kind of quantum dot may be passed through a channel where a flow of a water-immiscible matrix (e.g., oil) intercepts the flow of the aqueous solution to create emulsion droplets containing the particular kind of quantum dot, e.g., emulsion droplets each containing one red quantum dot. A standard droplet-generating device, such as a Flow Focusing Device, may be used. Other emulsion droplets may be produced separately in a similar fashion, preferably in parallel, for example to provide a population of emulsion droplets each containing two blue quantum dots, and a population of emulsion droplets each containing three violet quantum dots. These reagent emulsions may be stored before use.

A set of vials of reagent emulsions are selected from cold storage, and installed in a benchtop instrument. These emulsions contain various types of aqueous droplets within a fluorocarbon oil. One type (called Vial X) contains droplets with red-emitting quantum dots (coated with Antibody A). Another type (called Vial Y) contains droplets with blue-emitting quantum dots (coated with Antibody B). Yet another type (called Vial Z) contains droplets with violet-emitting quantum dots (coated with Antibody C).

A sample of Reagent R in free solution is added to the benchtop instrument.

The benchtop instrument forms a large droplet of the Reagent R solution within a fluorocarbon oil, and pumps the droplet into the entrance end of a flat, wide preparatory chamber (similar to the analytical chamber of the other Examples). At the same time, each of the emulsions is pumped into a flat side of the preparatory chamber, through a series of small holes near the entrance end. The emulsion droplets get trapped underneath the large droplet of Reagent R solution, like small balls underneath a carpet. Note that the emulsion droplets may be of arbitrary size and not necessarily be under the large droplet; the emulsion droplets may be adjacent to the large droplet rather than under it. Fluorocarbon oil is pumped into the entrance end of the preparatory chamber, causing the Reagent R solution droplet to be pushed through the preparatory chamber and out the distal end. The emulsion droplets get swept along with it, assisted by gravity and grooves in the surfaces of the preparatory chamber to constrain the emulsion droplet migrations to stay under the large droplet.

The flow rate of each of the emulsions into the preparatory chamber is controlled, to provide a controlled total number of red, blue, and violet quantum dots under the large droplet.

A brief pulse of an electric field causes the thin gap of fluorocarbon oil (between the emulsion droplets and the Reagent R solution) to be breached, demulsifying the emulsion droplets. The quantum dots within each droplet are now free to diffuse into the Reagent R solution. The large droplet containing the quantum dots now has a controlled composition of red (Antibody A), blue (Antibody B), and violet (Antibody C) quantum dots along with Reagent R, albeit not in a uniform mixture.

The large droplet is expelled out of the distal end of the preparatory chamber. The content of the large droplet is mixed by standard microfluidic methods, such as by a circuitous or turbulent pathway.

The large droplet is passed into a standard droplet-generating device, such as a Flow Focusing Device. This forms a large population of small droplets out of the large droplet, all having the same composition, e.g., with each small droplet containing one red quantum dot, two blue quantum dots, and three violet quantum dots. These small droplets are collected and stored in a vial for later use, such as in an analytical chamber as described in the other Examples. Other emulsion droplets may be produced separately in a similar fashion, preferably in parallel using the a preparatory chamber described herein, for example to provide a population of emulsion droplets each containing one yellow quantum dot, one green quantum dot, one dark blue quantum dot, and three red quantum dots; and a population of emulsion droplets each containing one green quantum dot, one orange quantum dot, two yellow quantum dots, and two dark blue quantum dots. These populations may be separately stored and used, or may be mixed in defined ratios for storage and/or use in an analytical chamber as described in the other Examples.

The preparatory chamber may be designed to be in parallel or in sequence with other preparatory chambers, as needed for production of the small droplets.

Example 14: Compositions and Methods for Drug Discovery with Emulsified Target

Essentially as described in Example 3, the compositions and methods are also used with an emulsified drug target.

Figure 27:
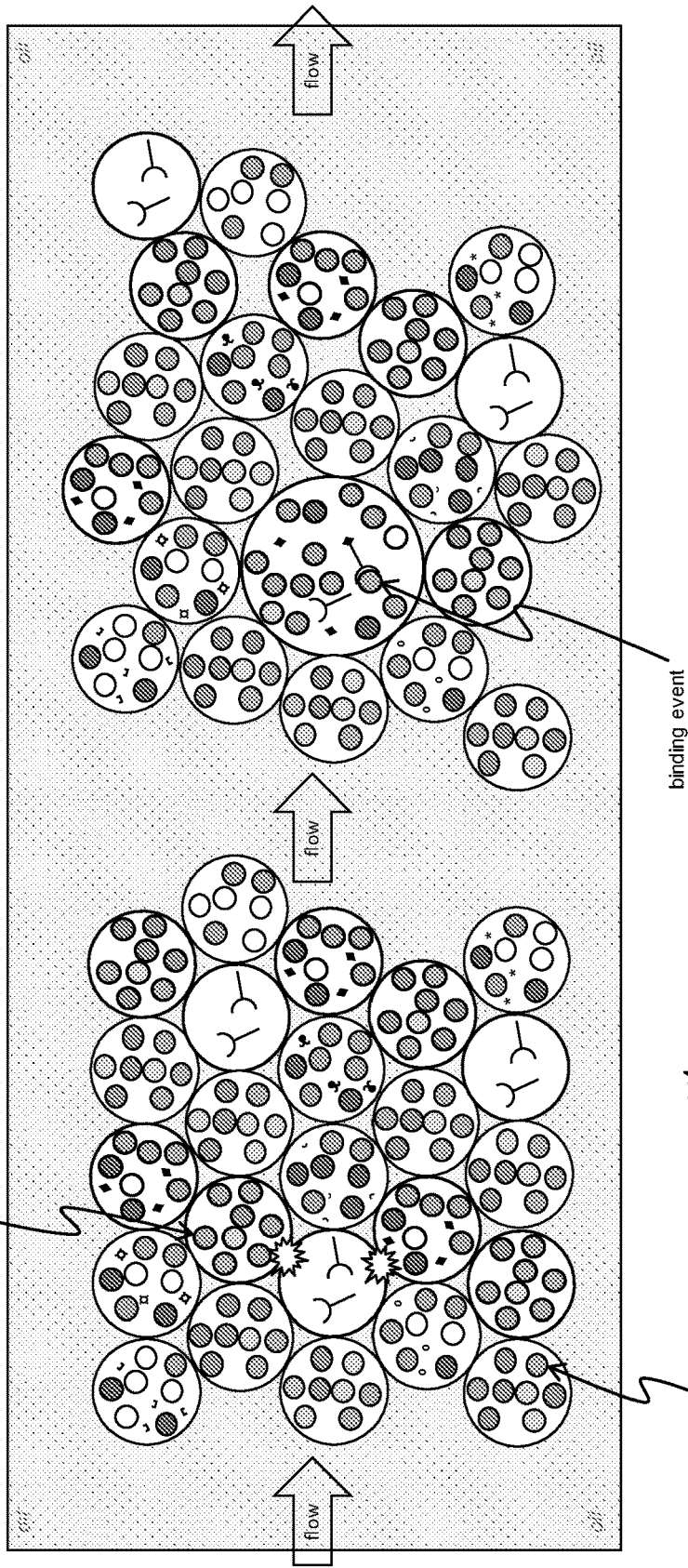
FIG. 27 shows an exemplary method of labeling emulsion droplets using free quantum dots.

A vial of reagent emulsion is selected from cold storage, and installed in a benchtop instrument. This reagent emulsion contains various types of aqueous droplets within a fluorocarbon oil optionally containing additives that adjust the refractive index to closely match the aqueous droplets. As shown in FIG. 27, one type (called sub-population X) contains approximately 1 red-emitting quantum dot (coated with Ligand A), 1 orange-emitting quantum dot (coated with Ligand B), and 6 blue-emitting quantum dots (coated with Ligand C). Another type (called sub-population Y) contains approximately 4 red-emitting quantum dots (coated with Ligand D), 2 orange-emitting quantum dots (coated with Ligand E), and 2 blue-emitting quantum dots (coated with Ligand F). Yet another type (called sub-population Z) contains approximately 5 red-emitting quantum dots (coated with Ligand G), 1 orange-emitting quantum dot (coated with Ligand H), and 2 blue-emitting quantum dots (coated with Ligand I). The vial may contain thousands of such unique types, and forms a screening library of drug candidates. The aqueous droplets may optionally contain an antifreeze such as ethylene glycol or glycerin to allow for the cold storage.

An emulsion of drug target (Receptor R) solution is also added to the benchtop instrument. This target emulsion contains aqueous droplets within a fluorocarbon oil optionally containing additives that adjust the refractive index to closely match the aqueous droplets. This drug target is tested against a large screening library of drug candidates, e.g., Ligand A through Ligand I, to screen for ligands that specifically target Receptor R.

A vial of synergetic emulsion is selected from cold storage, and also optionally added to the benchtop instrument. This synergetic emulsion contains various types of aqueous droplets within a fluorocarbon oil optionally containing additives that adjust the refractive index to closely match the aqueous droplets (such as bromocarbon or iodocarbon compounds). As shown in FIG. 27, one type (called sub-population Chi) contains approximately 1 yellow-emitting quantum dot, 4 green-emitting quantum dots, and 2 purple-emitting quantum dots, and synergetic candidate Alpha. Another type (called sub-population Psi) contains approximately 5 green-emitting quantum dots, 2 purple-emitting quantum dots, and synergetic candidate Beta. Yet another type (called sub-population Omega) contains approximately 3 green-emitting quantum dots, 4 purple-emitting quantum dots, and synergetic candidate Gamma. The vial may contain thousands of such unique types, and forms a screening library of synergetic candidates. The aqueous droplets may optionally contain an antifreeze such as ethylene glycol or glycerin to allow for the cold storage. Since these quantum dots will not be used for binding interactions, they may be formulated to have an exceptionally thick or thin shell that reduces or enhances their diffusivity sufficient to allow discrimination against ligand coated quantum dots of the same color. This would allow a large increase in the address space. For example, a red-emitting quantum dot coated with Ligand A could be optically distinguished from a very thick shelled red-emitting quantum dot with no coating.

The benchtop instrument pumps the droplets from the two or three emulsion sources into the entrance end of a flat, wide analytical chamber. The emulsion droplets become randomly interspersed in a flat flocculated array. Fluorocarbon oil is pumped into the entrance end of the analytical chamber, causing the emulsion droplets to be pushed through the analytical chamber and out the distal end.

The droplets are imaged to determine the chemical composition of each droplet based on the quantum dot composition. A calculation is performed for determining which touching droplets would provide the most useful information if merged.

A brief pulse of a focused laser between two touching droplets causes the thin gap of fluorocarbon oil to be breached, merging the pair of droplets into a resultant larger droplet, as described by Hayat et al., Biosensors 2019, 9, 129. The contents of each source droplet are now free to mix within the resultant larger droplet. The composition of the fluorocarbon oil, surfactants, or aqueous droplets may be tailored to improve the efficacy of the laser pulse for merging droplets. The laser light may be structured or pulsed to improve the efficacy of the laser pulse for merging droplets. The thickness of the analytical chamber may be cycled to redistribute the droplets for optimal contacts.

For example, if a Type X droplet, a Type Chi droplet, and a target droplet are merged, it would create a resultant larger droplet containing approximately 1 red-emitting quantum dot (coated with Ligand A), 1 orange-emitting quantum dot (coated with Ligand B), 6 blue-emitting quantum dots (coated with Ligand C), 1 yellow-emitting quantum dot, 4 green-emitting quantum dots, 2 purple-emitting quantum dots, synergetic candidate Alpha, and Receptor R.

The quantum dots within the resultant larger droplet diffuse freely within its volume.

Eventually, a particular quantum dot encounters a drug target molecule in the presence of a synergetic candidate, and a binding interaction occurs, forming a structure of summed size. If the drug target is on the same size scale as quantum dots, in the range of 10 nanometers diameter, then a binding interaction would double the size and more than halve the diffusivity. The other quantum dots would have constant diffusivities.

During the quantum dot diffusion process, structured near-infrared light is projected through the analytic chamber. Fluorescence emission light produced by two-photon excitation is collected by a camera. As the quantum dots randomly diffuse within the resultant larger droplet, their fluorescence position correspondingly changes.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it is found, for example, that blue quantum dots exhibiting the step down in diffusivity originate from a Type X droplet (identified by its unique signature of 1 red, 1 orange, and 6 blue quantum dots) and are merged with a Type Chi droplet (identified by its unique signature of 1 yellow, 4 green, and 2 purple quantum dots). This is indicative that Ligand C has a binding interaction with Receptor R in the presence of synergetic candidate Alpha, and may be a good candidate for detailed study.

Example 15: Compositions and Methods for Drug Discovery with Gel Beads

Essentially as described in Example 14, the compositions and methods are also used with a mixture of free quantum dots and gel beads that contain quantum dots. Using a mixture of free quantum dots (e.g., having a ligand coating) and gel beads (containing quantum dots used only for identification of the droplet) allows a very large address space.

Figure 28:
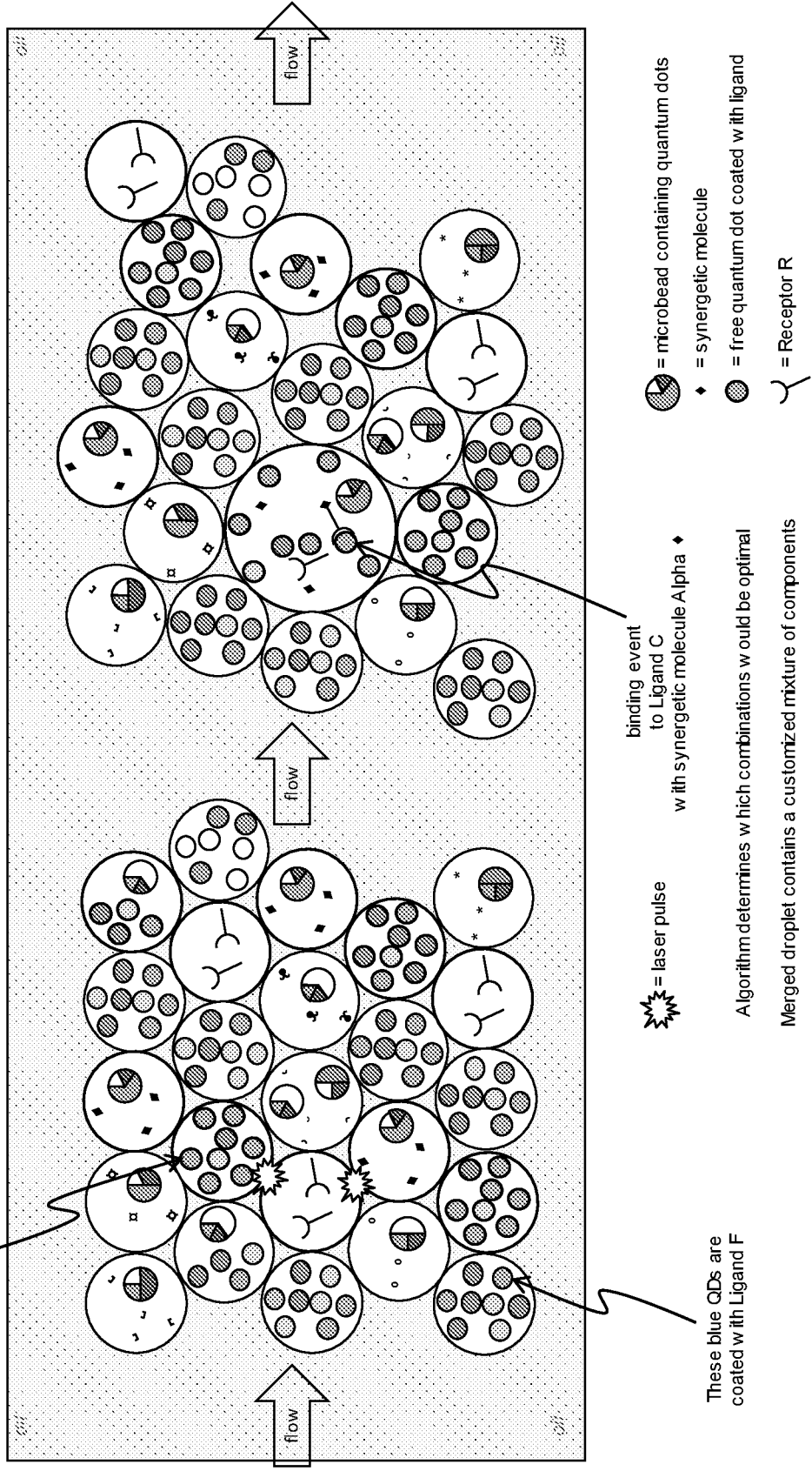
FIG. 28 shows an exemplary method of labeling emulsion droplets using free quantum dots and microbeads, such as gel beads.

A vial of reagent emulsion is selected from cold storage, and installed in a benchtop instrument. This reagent emulsion contains various types of aqueous droplets within a fluorocarbon oil. As shown in FIG. 28, one type (called sub-population X) contains approximately 1 red-emitting quantum dot (coated with Ligand A), 1 orange-emitting quantum dot (coated with Ligand B), and 6 blue-emitting quantum dot (coated with Ligand C). Another type (called sub-population Y) contains approximately 4 red-emitting quantum dots (coated with Ligand D), 2 orange-emitting quantum dots (coated with Ligand E), and 2 blue-emitting quantum dots (coated with Ligand F). Yet another type (called sub-population Z) contains approximately 2 red-emitting quantum dots (coated with Ligand G), 1 orange-emitting quantum dots (coated with Ligand H), 1 blue-emitting quantum dot (coated with Ligand I), and a gel bead containing 60% yellow quantum dots, 20% blue quantum dots, and 20% purple quantum dots. The vial may contain thousands of such unique types, and forms a screening library of drug candidates.

Such gel beads are commercially available, and in some cases are formed by chemically swelling an empty gel bead, soaking in the presence of free quantum dots, and then chemically de-swelling the gel bead to affix quantum dots within it.

The quantum dots within the gel beads do not diffuse randomly away from each other, and thus can be optically distinguished from free quantum dots. Multiple types of gel beads can be used within a same droplet that also contains free quantum dots having a surface coated with ligand, which gives a massive address space.

An emulsion of drug target (Receptor R) solution is also added to the benchtop instrument. This target emulsion contains aqueous droplets within a fluorocarbon oil. This drug target is tested against a large screening library of drug candidates, e.g., Ligand A through Ligand I, to screen for ligands that specifically target Receptor R.

A vial of synergetic emulsion is selected from cold storage, and also optionally added to the benchtop instrument. This synergetic emulsion contains various types of aqueous droplets within a fluorocarbon oil. As shown in FIG. 28, one type (called sub-population Chi) contains a gel bead containing 60% green quantum dots, 20% yellow quantum dots, and 20% purple quantum dots, and synergetic candidate Alpha. Another type (called sub-population Psi) contains a gel bead containing 60% yellow quantum dots, 20% purple quantum dots, 20% green quantum dots, and synergetic candidate Beta. Yet another type (called sub-population Omega) contains a gel bead containing 60% yellow quantum dots, 20% purple quantum dots, and 20% blue quantum dots, a gel bead containing 50% red quantum dots, 25% purple quantum dots, and 25% yellow quantum dots, and synergetic candidate Gamma. The vial may contain thousands of such unique types, and forms a screening library of synergetic candidates.

The benchtop instrument pumps the droplets from the two or three emulsion sources into the entrance end of a flat, wide analytical chamber. The emulsion droplets become randomly interspersed in a flat flocculated array. Fluorocarbon oil is pumped into the entrance end of the analytical chamber, causing the emulsion droplets to be pushed through the analytical chamber and out the distal end.

The droplets are imaged to determine the chemical composition of each droplet based on the quantum dot composition. A calculation is performed for determining which touching droplets would provide the most useful information if merged.

A brief pulse of a focused laser between two touching droplets causes the thin gap of fluorocarbon oil to be breached, merging the pair of droplets into a resultant larger droplet. The contents of each source droplet are now free to mix within the resultant larger droplet. The composition of the fluorocarbon oil, surfactants, or aqueous droplets may be tailored to improve the efficacy of the laser pulse for merging droplets. The laser light may be structured or pulsed to improve the efficacy of the laser pulse for merging droplets. The thickness of the analytical chamber may be cycled to redistribute the droplets for optimal contacts.

For example, if a Type X droplet, a Type Chi droplet, and a target droplet are merged, it would create a resultant larger droplet containing approximately 1 red-emitting quantum dot (coated with Ligand A), 1 orange-emitting quantum dot (coated with Ligand B), 6 blue-emitting quantum dots (coated with Ligand C), a gel bead containing 60% green quantum dots, 20% yellow quantum dots, and 20% purple quantum dots, synergetic candidate Alpha, and Receptor R.

The quantum dots within the resultant larger droplet diffuse freely within its volume. The quantum dots entrapped within the gel bead are constrained to diffuse together.

Eventually, a particular quantum dot encounters a drug target molecule in the presence of a synergetic candidate, and a binding interaction occurs, forming a structure of summed size. If the drug target is on the same size scale as quantum dots, in the range of 10 nanometers diameter, then a binding interaction would double the size and more than halve the diffusivity. The other quantum dots would have constant diffusivities.

During the quantum dot diffusion process, structured near-infrared light is projected through the analytic chamber. Fluorescence emission light produced by two-photon excitation is collected by a camera. As the quantum dots randomly diffuse within the resultant larger droplet, their fluorescence position correspondingly changes.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it is found, for example, that blue quantum dots exhibiting the step down in diffusivity originate from a Type X droplet (identified by its unique signature of 1 red, 1 orange, and 6 blue quantum dots) and are merged with a Type Chi droplet (identified by its unique signature of a gel bead containing 60% green, 20% yellow, and 20% purple quantum dots). This is indicative that Ligand C has a binding interaction with Receptor R in the presence of synergetic candidate Alpha, and may be a good candidate for detailed study.

Figure 29:
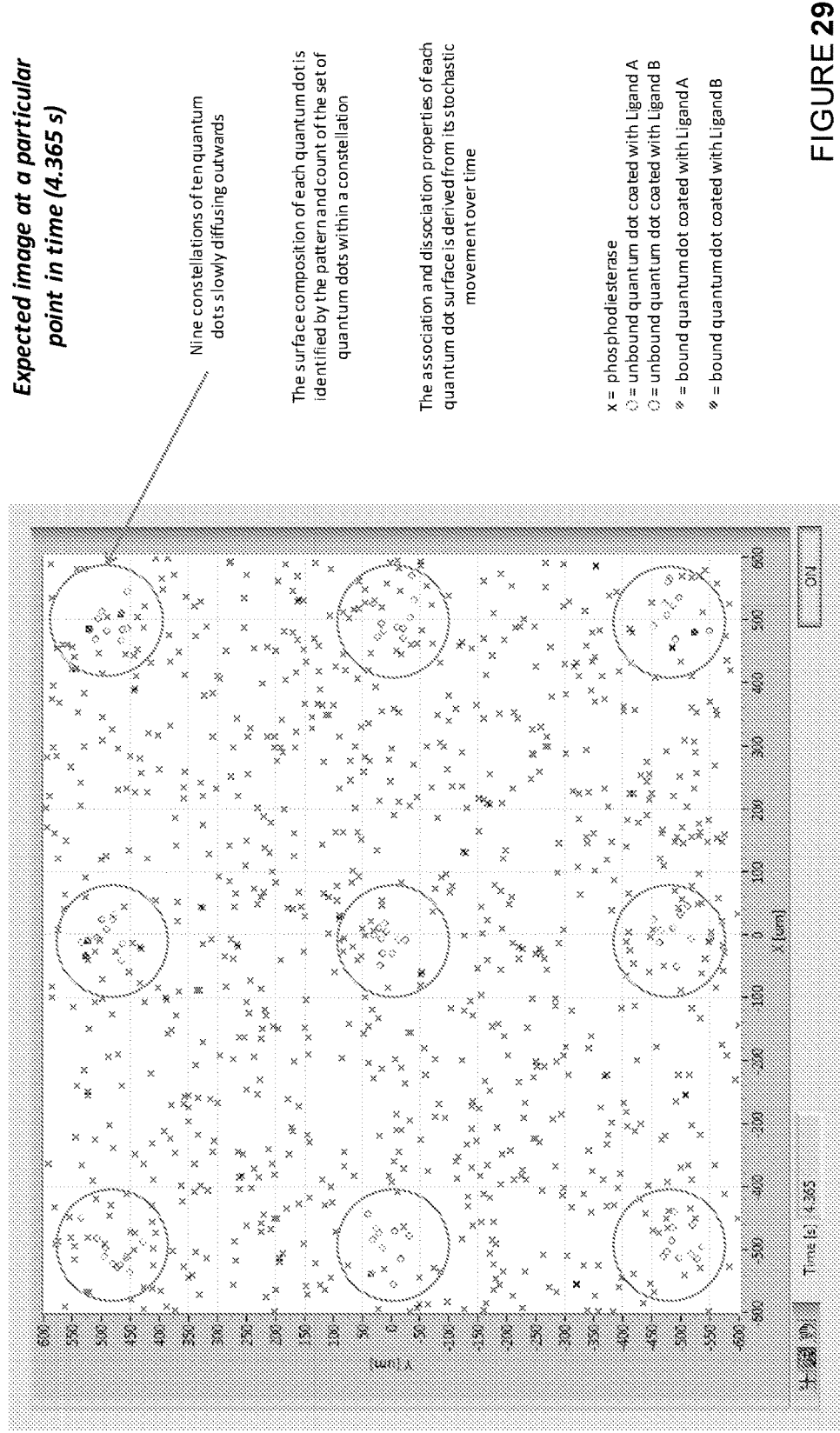
FIG. 29 shows an expected image of 90 quantum dots in a simulation, where nine constellations of ten quantum dots in each constellation slowly diffuse outwards. Binding interactions of the quantum dots with phosphodiesterase are simulated.
Figure 30:
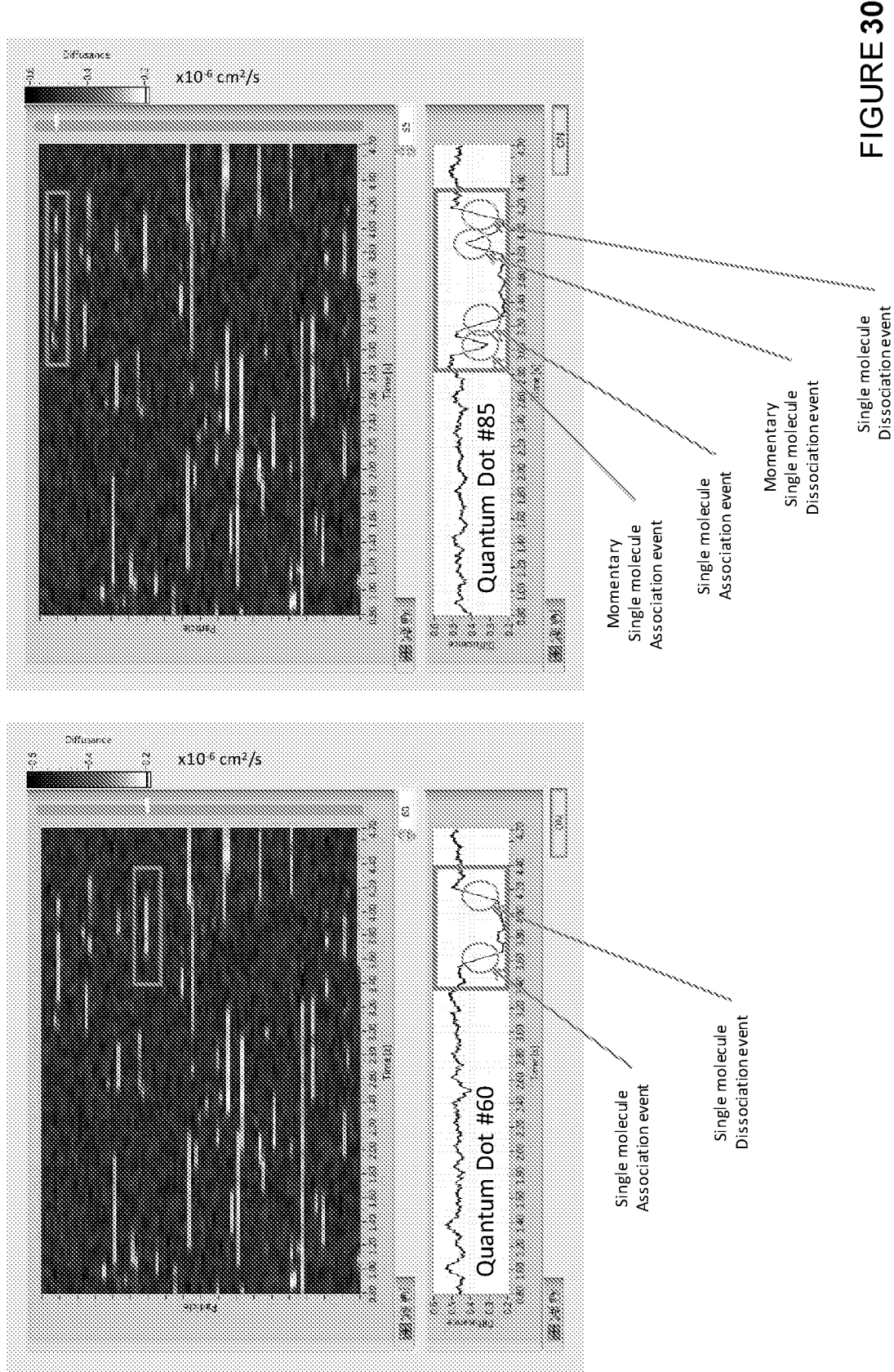
FIG. 30 shows exemplary molecular association and/or dissociation events during the simulation shown in FIG. 29.
Figure 31:
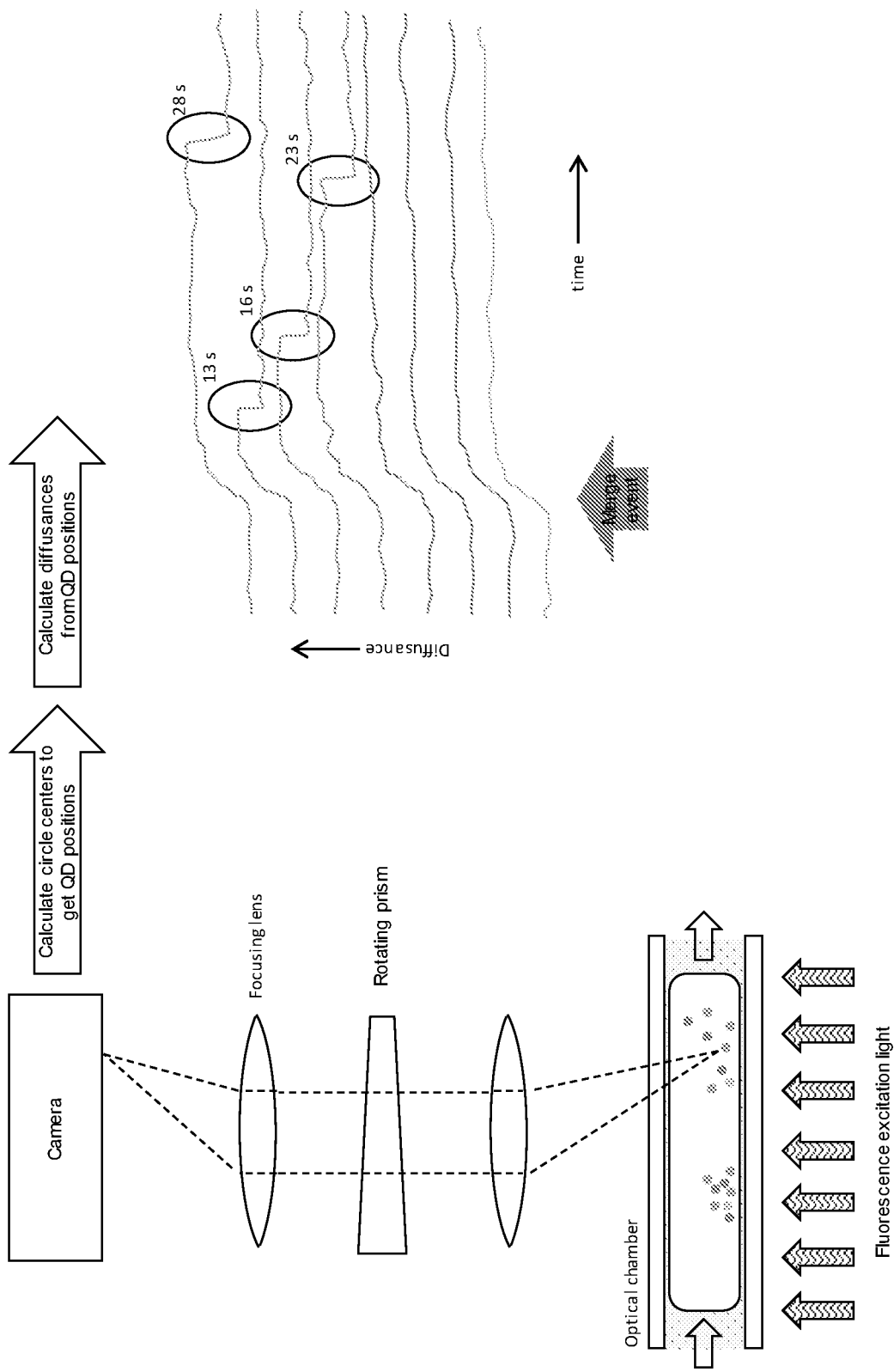
FIG. 31 is a schematic of an exemplary optical system for measuring fluorescence emission light from an exemplary analytic chamber. A rotating prism (e.g., as in a Risley Prism Scanner) can be used instead of a diffraction grating (e.g., as shown in FIG. 12).

Example 16: Simulating Binding Interactions Between Quantum Dots and Phosphodiesterase Nine constellations of ten quantum dots are simulated to slowly diffuse outwards, to analyze their binding interactions with phosphodiesterase. The surface composition of each quantum dot is identified by the pattern and count of the set of quantum dots within a constellation. The association and dissociation properties of each quantum dot surface are derived from its stochastic movement over time. An expected image at a particular point in time (4.365 s) is shown in FIG. 29. Analysis of diffusance of the quantum dots reveals molecular association and dissociation events as shown in FIG. 30.

Example 17: Methods and Compositions for Live Cell Interrogation

Essentially as described in Example 8, the compositions and methods are also used with live cells during the measurements, rather than lysing the cells.

A stream of emulsion is prepared, and injected into a benchtop instrument. This emulsion contains various types of aqueous droplets within a fluorocarbon oil having the same refractive index as the aqueous droplets. One type (called sub-population X) contains approximately 6 red-emitting quantum dots (coated with Antibody A), 9 green-emitting quantum dots (coated with Antibody B), 3 blue-emitting quantum dots (coated with Antibody C), a single cell, and lysing enzyme. Another type (called sub-population Y) contains approximately 6 red-emitting quantum dots (coated with Antibody D), 12 yellow-emitting quantum dots (coated with Antibody E), 3 blue-emitting quantum dots (coated with Antibody F), a single cell, and lysing enzyme. Yet another type (called sub-population Z) contains approximately 6 red-emitting quantum dots (coated with Antibody G), 9 green-emitting quantum dots (coated with Antibody H), 6 blue-emitting quantum dots (coated with Antibody I), a single cell, and lysing enzyme. For any sub-population X, Y, or Z droplet, the droplet may be manufactured to comprise a single cell. Alternatively, a droplet may be manufactured to comprise only a single cell. The vial may contain thousands of such unique types, and forms a library, e.g., of diagnostic reagents.

The benchtop instrument pumps the emulsion into the entrance end of a flat, wide analytical chamber. The quantum dots within each aqueous droplet diffuse randomly within the volume of the aqueous droplet.

For droplets that contain both quantum dots and cells, the quantum dots may become internal to the cell or bind to the outer surface, e.g., as described in Daniel et al., J. Phys. D: Appl. Phys. 49 (2016) 084002; Chen et al., Nature Communications 8: 887; Gardini et al., Scientific Reports 5 (2015) 16088; Zhang et al., Anal. Chem. 91 (2019) 532; Zahid et al., Nature Communications 9 (2018) 1830; Abraham et al., Scientific Reports 7 (2017) 11379; and von Diezmann et al., Chem. Rev. 117 (2017) 7244.

A particular quantum dot encounters a cell component, and a binding interaction occurs, forming a structure of summed size. For cell component on the same size scale as quantum dots, in the range of 10 nanometers diameter, then a binding interaction doubles the size and more than halve the diffusivity, while quantum dots that do not bind cell components have constant diffusivities. Additionally, if a cell protein has two different epitopes, and there are two different colors of quantum dots with matching paratopes, then a structure will be formed having both colors that diffuse together, as long as the quantum dots are separated beyond a quenching distance; this would be useful for discriminating against non-specific binding.

During the quantum dot diffusion process, ultraviolet light is projected through the analytic chamber. In some cases, an oil (such as perfluorodecalin, RI=1.31) with approximately the same refractive index as the aqueous droplets (RI=1.33) is used. Since the refractive index of the fluorocarbon oil and the aqueous droplets is the same or substantially the same, there is no or little boundary refraction.

Fluorescence emission light is collected by a camera, as a collection of fluorescent point sources originating from the quantum dots. The camera records the positions of the fluorescent point sources (and thereby the positions of the quantum dots) as they randomly diffuse within each droplet. The aqueous droplets are of a sufficient size so that the quantum dots are spread apart sufficiently for individual detection. Typically, the separation distance in the focal plane needs is at least 500 nm. In some cases, this is achieved by flattening the droplets into a pancake shape within the analytic chamber.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots are observed to have an initial high diffusivity, but then step to a lower diffusivity later. Other quantum dots maintain a high diffusivity. Tracking the step-changed quantum dots back in time is used to detect and/or analyze binding interaction(s), e.g., between an antibody and a cell component. In one example, blue quantum dots within a Type Y droplet (identified by its unique signature of 6 red, 12 yellow, and 3 blue quantum dots) have an initial high diffusivity, but then step to a lower diffusivity, indicating that Antibody F on the blue quantum dots has a binding interaction with one or more of the components of the particular cell lysed inside the Type Y droplet. In some instances, each droplet of the Type Y droplets encapsulate a single cell of a cell population, and comparing the behavior of all blue quantum dots within the set of Type Y droplets provides information on the heterogeneity of the cell population.

Example 18: Compositions and Methods for Drug Discovery with Beam Deflection

Essentially as described in Example 14, the compositions and methods are also used with optics that deflect the beam in a pattern to enhance position precision.

A vial of reagent emulsion is selected from cold storage, and installed in a benchtop instrument. This reagent emulsion contains various types of aqueous droplets within a fluorocarbon oil optionally containing additives that adjust the refractive index to closely match the aqueous droplets. As shown in FIG. 27, one type (called sub-population X) contains approximately 1 red-emitting quantum dot (coated with Ligand A), 1 orange-emitting quantum dot (coated with Ligand B), and 6 blue-emitting quantum dots (coated with Ligand C). Another type (called sub-population Y) contains approximately 4 red-emitting quantum dots (coated with Ligand D), 2 orange-emitting quantum dots (coated with Ligand E), and 2 blue-emitting quantum dots (coated with Ligand F). Yet another type (called sub-population Z) contains approximately 5 red-emitting quantum dots (coated with Ligand G), 1 orange-emitting quantum dot (coated with Ligand H), and 2 blue-emitting quantum dots (coated with Ligand I). The vial may contain thousands of such unique types, and forms a screening library of drug candidates. The aqueous droplets may optionally contain an antifreeze such as ethylene glycol or glycerin to allow for the cold storage.

An emulsion of drug target (Receptor R) solution is also added to the benchtop instrument. This target emulsion contains aqueous droplets within a fluorocarbon oil optionally containing additives that adjust the refractive index to closely match the aqueous droplets. This drug target is tested against a large screening library of drug candidates, e.g., Ligand A through Ligand I, to screen for ligands that specifically target Receptor R.

A vial of synergetic emulsion is selected from cold storage, and also optionally added to the benchtop instrument. This synergetic emulsion contains various types of aqueous droplets within a fluorocarbon oil optionally containing additives that adjust the refractive index to closely match the aqueous droplets (such as bromocarbon or iodocarbon compounds). As shown in FIG. 27, one type (called sub-population Chi) contains approximately 1 yellow-emitting quantum dot, 4 green-emitting quantum dots, and 2 purple-emitting quantum dots, and synergetic candidate Alpha. Another type (called sub-population Psi) contains approximately 5 green-emitting quantum dots, 2 purple-emitting quantum dots, and synergetic candidate Beta. Yet another type (called sub-population Omega) contains approximately 3 green-emitting quantum dots, 4 purple-emitting quantum dots, and synergetic candidate Gamma. The vial may contain thousands of such unique types, and forms a screening library of synergetic candidates. The aqueous droplets may optionally contain an antifreeze such as ethylene glycol or glycerin to allow for the cold storage. Since these quantum dots will not be used for binding interactions, they may be formulated to have an exceptionally thick or thin shell that reduces or enhances their diffusivity sufficient to allow discrimination against ligand coated quantum dots of the same color. This would allow a large increase in the address space. For example, a red-emitting quantum dot coated with Ligand A could be optically distinguished from a very thick shelled red-emitting quantum dot with no coating.

The benchtop instrument pumps the droplets from the two or three emulsion sources into the entrance end of a flat, wide analytical chamber. The emulsion droplets become randomly interspersed in a flat flocculated array. Fluorocarbon oil is pumped into the entrance end of the analytical chamber, causing the emulsion droplets to be pushed through the analytical chamber and out the distal end.

The droplets are imaged to determine the chemical composition of each droplet based on the quantum dot composition. A calculation is performed for determining which touching droplets would provide the most useful information if merged.

A brief pulse of a focused laser between two touching droplets causes the thin gap of fluorocarbon oil to be breached, merging the pair of droplets into a resultant larger droplet, as described by Hayat et al., Biosensors 2019, 9, 129. The contents of each source droplet are now free to mix within the resultant larger droplet. The composition of the fluorocarbon oil, surfactants, or aqueous droplets may be tailored to improve the efficacy of the laser pulse for merging droplets. The laser light may be structured or pulsed to improve the efficacy of the laser pulse for merging droplets. More than two droplets may be merged together to explore synergistic interactions involving multiple components. The thickness of the analytical chamber may be cycled to redistribute the droplets for optimal contacts.

For example, if a Type X droplet, a Type Chi droplet, and a target droplet are merged, it would create a resultant larger droplet containing approximately 1 red-emitting quantum dot (coated with Ligand A), 1 orange-emitting quantum dot (coated with Ligand B), 6 blue-emitting quantum dots (coated with Ligand C), 1 yellow-emitting quantum dot, 4 green-emitting quantum dots, 2 purple-emitting quantum dots, synergetic candidate Alpha, and Receptor R.

The quantum dots within the resultant larger droplet diffuse freely within its volume.

Eventually, a particular quantum dot encounters a drug target molecule in the presence of a synergetic candidate, and a binding interaction occurs, forming a structure of summed size. If the drug target is on the same size scale as quantum dots, in the range of 10 nanometers diameter, then a binding interaction would double the size and more than halve the diffusivity. The other quantum dots would have constant diffusivities.

During the quantum dot diffusion process, ultraviolet light is projected through the analytic chamber. In some cases, an oil (such as perfluorodecalin, RI=1.31) with approximately the same refractive index as the aqueous droplets (RI=1.33) is used. Since the refractive index of the fluorocarbon oil and the aqueous droplets is the same or substantially the same, there is no or little boundary refraction.

Figure 32:
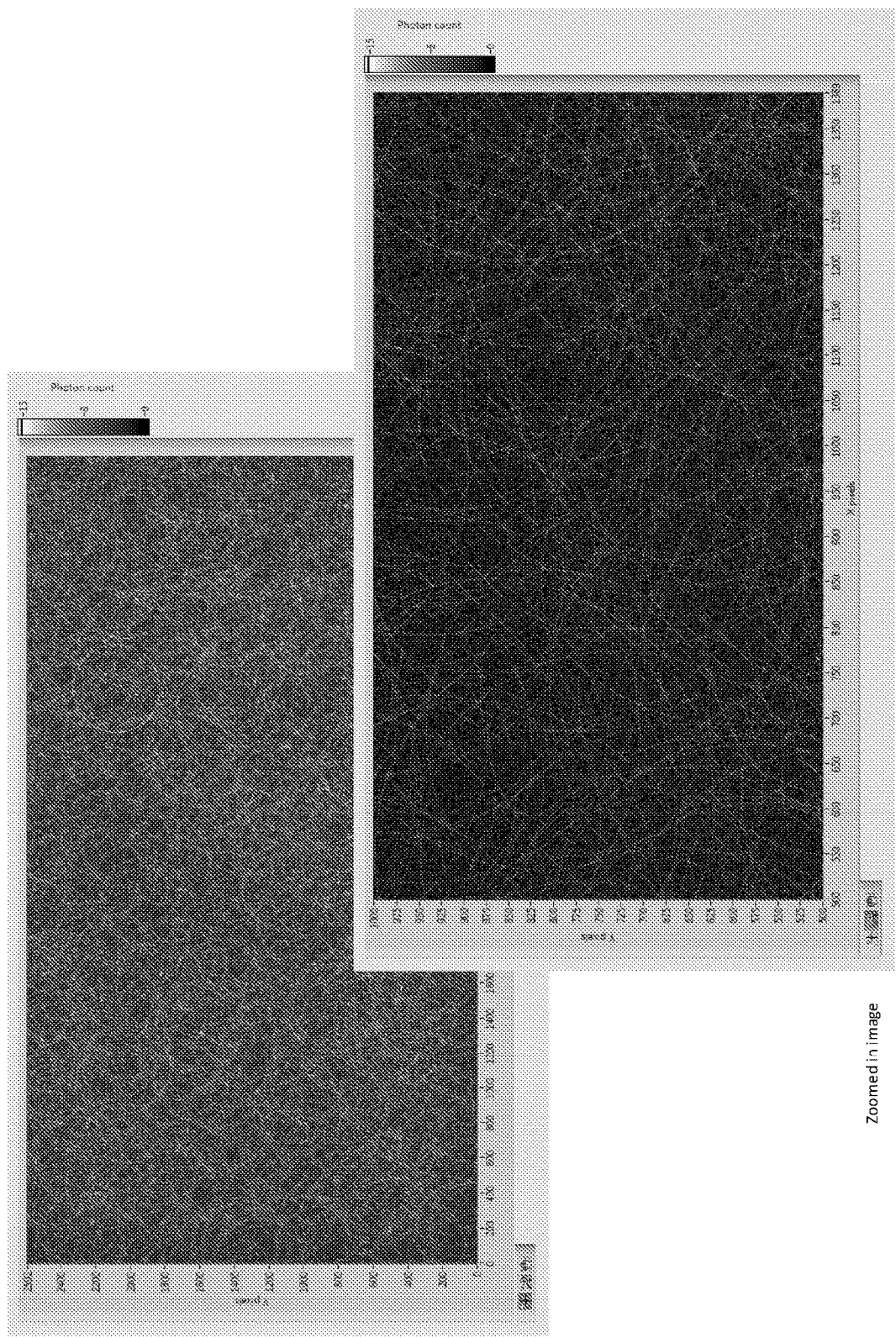
FIG. 32 shows exemplary camera images using a Risley Prism Scanner.

Fluorescence emission light is deflected by a beam deflection device, such as a piezoelectric-driven movable mirror, or a Risley Prism Scanner (e.g., a rotating prism). The light may be deflected into different patterns, such as circle, ellipse, Lissajous, or spirograph. The use of beam deflection distributes the photons onto multiple pixels, which may provide a higher position precision than simple direct imaging of the quantum dots as point sources. When a Risley Prism Scanner is used, two wedge prisms can be used to create an angular deviation of a beam from its optical axis to create continuous circular scan patterns or discrete beam pointing. Using a rotating prism, the circle radii (e.g., as shown in the exemplary camera images in FIG. 32) can provide identification of the quantum dot colors with a single camera.

Fluorescence emission light is collected by a camera, as a collection of overlapping circles (or other patterns) originating from the quantum dots. An image analysis algorithm determines the centers of the circles (and thereby the positions of the quantum dots) as they randomly diffuse within each droplet.

Without using a beam deflection device, photons emitted from a fluorescent particle will be focused into a particular pixel, and the location of the pixel gives the position of the fluorescent particle. The precision of the position will be dictated by the pixel size and the optical magnification factor. In contrast, with a beam deflection device, the photons will flow into a circular line of pixels instead of just one pixel (one rotation per frame), generating an image with multiple overlapping circular lines (one circle per fluorescent particle). Since a circular line of pixels is a much larger data set than a single pixel, this allows an algorithm to calculate a more precise center position, by fitting with a perfect circular line model. With the use of a prism, the circle radius also provides an identification of the fluorescent particle color. This concept can be expanded further to other patterns, such as ellipse, Lissajous, or spirograph for a longer pixel line per camera frame, and thus enhanced measurement speed. Furthermore, optical calibration can be performed: an optical system will generate imperfect circular lines, but if these are measured before an experiment, they can be used as empirical models (instead of a mathematically perfect circle model) that can be used by the algorithm that extracts the circle centers.

The fluorescence excitation light may be structured. For example, different areas of the analytic chamber may be illuminated at different frequencies and phases, causing the circle perimeters to have corresponding frequencies and phases. Since the circles are overlapping, this may allow the image analysis algorithm to better extract and differentiate the circles.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it is found, for example, that blue quantum dots exhibiting the step down in diffusivity originate from a Type X droplet (identified by its unique signature of 1 red, 1 orange, and 6 blue quantum dots) and are merged with a Type Chi droplet (identified by its unique signature of 1 yellow, 4 green, and 2 purple quantum dots). This is indicative that Ligand C has a binding interaction with Receptor R in the presence of synergetic candidate Alpha, and may be a good candidate for detailed study.

Example 19: Compositions and Methods for Drug Discovery with Droplet Lensing

Essentially as described in Example 14, the compositions and methods are also used with emulsion droplets that behave as a set of lenses.

A vial of reagent emulsion is selected from cold storage, and installed in a benchtop instrument. This reagent emulsion contains various types of aqueous droplets within a fluorocarbon oil optionally containing additives that adjust the refractive index to closely match the aqueous droplets. As shown in FIG. 27, one type (called sub-population X) contains approximately 1 red-emitting quantum dot (coated with Ligand A), 1 orange-emitting quantum dot (coated with Ligand B), and 6 blue-emitting quantum dots (coated with Ligand C). Another type (called sub-population Y) contains approximately 4 red-emitting quantum dots (coated with Ligand D), 2 orange-emitting quantum dots (coated with Ligand E), and 2 blue-emitting quantum dots (coated with Ligand F). Yet another type (called sub-population Z) contains approximately 5 red-emitting quantum dots (coated with Ligand G), 1 orange-emitting quantum dot (coated with Ligand H), and 2 blue-emitting quantum dots (coated with Ligand I). The vial may contain thousands of such unique types, and forms a screening library of drug candidates. The aqueous droplets may optionally contain an antifreeze such as ethylene glycol or glycerin to allow for the cold storage.

An emulsion of drug target (Receptor R) solution is also added to the benchtop instrument. This target emulsion contains aqueous droplets within a fluorocarbon oil optionally containing additives that adjust the refractive index to be different from the aqueous droplets. This drug target is tested against a large screening library of drug candidates, e.g., Ligand A through Ligand I, to screen for ligands that specifically target Receptor R.

A vial of synergetic emulsion is selected from cold storage, and also optionally added to the benchtop instrument. This synergetic emulsion contains various types of aqueous droplets within a fluorocarbon oil optionally containing additives that adjust the refractive index to closely match the aqueous droplets (such as bromocarbon or iodocarbon compounds). As shown in FIG. 27, one type (called sub-population Chi) contains approximately 1 yellow-emitting quantum dot, 4 green-emitting quantum dots, and 2 purple-emitting quantum dots, and synergetic candidate Alpha. Another type (called sub-population Psi) contains approximately 5 green-emitting quantum dots, 2 purple-emitting quantum dots, and synergetic candidate Beta. Yet another type (called sub-population Omega) contains approximately 3 green-emitting quantum dots, 4 purple-emitting quantum dots, and synergetic candidate Gamma. The vial may contain thousands of such unique types, and forms a screening library of synergetic candidates. The aqueous droplets may optionally contain an antifreeze such as ethylene glycol or glycerin to allow for the cold storage. Since these quantum dots will not be used for binding interactions, they may be formulated to have an exceptionally thick or thin shell that reduces or enhances their diffusivity sufficient to allow discrimination against ligand coated quantum dots of the same color. This would allow a large increase in the address space. For example, a red-emitting quantum dot coated with Ligand A could be optically distinguished from a very thick shelled red-emitting quantum dot with no coating.

The benchtop instrument pumps the droplets from the two or three emulsion sources into the entrance end of a flat, wide analytical chamber. The emulsion droplets become randomly interspersed in a flat flocculated array. Fluorocarbon oil is pumped into the entrance end of the analytical chamber, causing the emulsion droplets to be pushed through the analytical chamber and out the distal end.

The droplets are imaged to determine the chemical composition of each droplet based on the quantum dot composition. A calculation is performed for determining which touching droplets would provide the most useful information if merged.

A brief pulse of a focused laser between two touching droplets causes the thin gap of fluorocarbon oil to be breached, merging the pair of droplets into a resultant larger droplet, as described by Hayat et al., Biosensors 2019, 9, 129. The contents of each source droplet are now free to mix within the resultant larger droplet. The composition of the fluorocarbon oil, surfactants, or aqueous droplets may be tailored to improve the efficacy of the laser pulse for merging droplets. The laser light may be structured or pulsed to improve the efficacy of the laser pulse for merging droplets. More than two droplets may be merged together to explore synergistic interactions involving multiple components. The thickness of the analytical chamber may be cycled to redistribute the droplets for optimal contacts.

For example, if a Type X droplet, a Type Chi droplet, and a target droplet are merged, it would create a resultant larger droplet containing approximately 1 red-emitting quantum dot (coated with Ligand A), 1 orange-emitting quantum dot (coated with Ligand B), 6 blue-emitting quantum dots (coated with Ligand C), 1 yellow-emitting quantum dot, 4 green-emitting quantum dots, 2 purple-emitting quantum dots, synergetic candidate Alpha, and Receptor R.

The quantum dots within the resultant larger droplet diffuse freely within its volume.

Eventually, a particular quantum dot encounters a drug target molecule in the presence of a synergetic candidate, and a binding interaction occurs, forming a structure of summed size. If the drug target is on the same size scale as quantum dots, in the range of 10 nanometers diameter, then a binding interaction would double the size and more than halve the diffusivity. The other quantum dots would have constant diffusivities.

During the quantum dot diffusion process, ultraviolet light is projected through the analytic chamber. A fluorocarbon oil with either a higher or lower refractive index as the aqueous droplets (RI=1.33) is used. Since the refractive index of the fluorocarbon oil and the aqueous droplets is different, there is significant droplet boundary refraction.

Fluorescence emission light is refracted by the droplet boundary, where the droplet acts as a spherical lens.

Fluorescence emission light is collected by a set of cameras, as a collection of points occurring at different focal lengths originating from the quantum dots. Small x,y (planar) movements of the quantum dots within a droplet would by amplified by the droplet lens to produce a large movement across the camera image. Use of prisms to distribute the fluorescence emission light among a set of cameras with different focal planes would allow collecting data for quantum dots at different z (axial) positions.

The data on the fluorescence position of each quantum dot is analyzed. Each quantum dot exhibits random movement in the x, y, and z directions over time, and the magnitude of the optically-detected movements in the x and y directions are dependent on the diffusivity. Some of the quantum dots maintain a high diffusivity. Other quantum dots are observed to have an initial high diffusivity, but then step to a lower diffusivity later. Tracking the step-changed quantum dots back in time, it is found, for example, that blue quantum dots exhibiting the step down in diffusivity originate from a Type X droplet (identified by its unique signature of 1 red, 1 orange, and 6 blue quantum dots) and are merged with a Type Chi droplet (identified by its unique signature of 1 yellow, 4 green, and 2 purple quantum dots). This is indicative that Ligand C has a binding interaction with Receptor R in the presence of synergetic candidate Alpha, and may be a good candidate for detailed study.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing an analyte, comprising:
a) contacting (i) a first composition comprising a liquid phase and a sample in the liquid phase, with (ii) a second composition comprising a liquid matrix and a formulation encapsulated in the liquid matrix, wherein the formulation comprises a plurality of fluorescent constructs and an analyte-interacting reagent attached to one or more of the fluorescent constructs, wherein the second composition comprises or is an emulsion of the liquid matrix and the formulation; and
combining the liquid phase and the formulation such that an analyte in the sample interacts with the analyte-interacting reagent attached to the one or more of the fluorescent constructs to generate a detectable signal,
wherein the detectable signal is analyzed using optical position tracking and wherein the analysis indicates a presence or absence, an amount or concentration, and/or an activity of the analyte in the sample; or
b) contacting (i) a first composition comprising a liquid phase and a sample in the liquid phase, with (ii) a second composition comprising a liquid matrix and a formulation encapsulated in the liquid matrix, wherein the formulation comprises a plurality of fluorescent constructs and an analyte-interacting reagent attached to one or more of the fluorescent constructs;
combining the liquid phase and the formulation in an analytic chamber, such that an analyte in the sample interacts with the analyte-interacting reagent attached to the one or more of the fluorescent constructs;
directing an excitation light through the analytic chamber to cause fluorescence of the fluorescent constructs;
detecting and/or measuring fluorescence emission as the fluorescent constructs within each formulation diffuse in the combined composition;
determining the identity of each analyte-interacting reagent present within each formulation based on a pattern of fluorescent emission wavelengths during the diffusion,
wherein a change in the stochastic behavior of the fluorescence emission position and/or magnitude of the fluorescence emission provides an indication of presence or absence, an amount, and/or an activity of the analyte in the sample.

2. The method of claim 1, wherein the analyte-interacting reagent is:
(i) an analyte-binding reagent;
(ii) directly attached to the one or more of the fluorescent constructs;
(iii) indirectly attached to the one or more of the fluorescent constructs via a linker or a common binding partner; or
(iv) covalently or non-covalently attached to the one or more of the fluorescent constructs, wherein each of the one or more of the fluorescent constructs has one or more analyte-interacting reagents attached thereto, or only a subset of the one or more of the fluorescent constructs has one or more analyte-interacting reagents attached thereto.

3. The method of claim 1, wherein the liquid phase and the formulation merge into a single fluid during the combining step, wherein the combination of the liquid phase and the formulation occurs in an analytic chamber, and wherein the liquid phase is water and the formulation is soluble in and/or miscible with water.

4. The method of claim 1, wherein:
(a) the analyte in the sample is capable of specific binding to the analyte-interacting reagent; or
(b) the analyte in the sample and the analyte-interacting reagent are capable of participating in a reaction including an enzymatic reaction catalyzed by the analyte, by the analyte-interacting reagent, and/or by an agent in the sample and/or the formulation.

5. The method of claim 1, wherein the plurality of fluorescent constructs comprise one or more:
(i) fluorescent particles, fluorescent small molecules, fluorescent peptides or proteins, fluorescent dyes, or any combination thereof;
(ii) fluorescent semiconductor nanoparticles; or
(iii) quantum dots.

6. The method of claim 1, wherein the formulation comprises:
(a) one or more polymeric particle each comprising one or more fluorescent particle, one or more fluorescent small molecule, one or more fluorescent peptide or protein, one or more fluorescent dye, or any combination thereof;
(b) an aqueous droplet, wherein the aqueous droplet comprises an antifreeze, such as including ethylene glycol or glycerin; or
(c) a gel or a gel in the form of a gel bead, wherein the gel comprises the plurality of fluorescent constructs and is capable of releasing the plurality of fluorescent constructs upon melting or otherwise disintegrating the gel.

7. The method of claim 1, wherein the liquid matrix:
(a) is immiscible or substantially immiscible with water;
(b) comprises a lipid, an oil, a hydrocarbon fluid, a fluorocarbon fluid, a chlorocarbon fluid, a bromocarbon fluid, an iodocarbon fluid, a silicone fluid, or a mixture thereof, or
(c) is selected from the group consisting of a lipid, an oil, a hydrocarbon fluid, a fluorocarbon fluid, a chlorocarbon fluid, a bromocarbon fluid, an iodocarbon fluid, a silicone fluid, and a mixture thereof.

8. The method of claim 1, wherein the combining step:
(i) comprises combining adjacent streams of the first composition and the formulation, respectively;
(ii) comprises combining transverse streams of the first composition and the formulation, respectively;
(iii) comprises combining perpendicular streams of the first composition and the formulation, respectively;
(iv) comprises combining oblique streams of the first composition and the formulation, respectively;
(v) comprises combining opposed streams of the first composition and the formulation, respectively;
(vi) comprises combining concentric streams of the first composition and the formulation, respectively;
(vii) comprises application of an electric field to the first and/or second compositions, wherein the first composition and the second composition comprise surfactants of opposite charges, respectively, and the combining step comprises contacting the surfactants of opposite charges with one another;

(viii) comprises application of a demulsification agent to the first and/or second compositions;
(ix) does not comprise application of a demulsification agent;
(x) comprises application of heat to the first and/or second compositions; or
(xi) comprises application of a gel depolymerization agent to the first and/or second compositions.

9. The method of claim 1, wherein the first composition and/or the formulation comprise one or more:
(i) demulsifying agents;
(ii) gelling agents; or
(iii) viscosity-enhancing agents,
wherein the first composition is a first emulsion comprising the liquid phase as an emulsified droplet within a first liquid matrix, and the liquid matrix of the second composition is a second liquid matrix, wherein the emulsified droplet comprises an antifreeze including ethylene glycol or glycerin.

10. The method of claim 1, wherein the detectable signal is:
(i) a fluorescent signal;
(ii) induced by excitation light comprising, consisting essentially of, or consisting of non-polarized light;
(iii) induced by excitation light comprising, consisting essentially of, or consisting of linearly polarized light
(iv) induced by excitation light comprising, consisting essentially of, or consisting of circularly polarized light
(v) induced by excitation light comprising, consisting essentially of, or consisting of elliptically polarized light and/or trochoidally polarized light;
(vi) induced by excitation light comprising, consisting essentially of, or consisting of light of a single wavelength;
(vii) induced by excitation light comprising, consisting essentially of, or consisting of polychromatic light;
(viii) induced by excitation light comprising, consisting essentially of, or consisting of non-coherent light;
(ix) induced by excitation light comprising, consisting essentially of, or consisting of coherent light;
(x) induced by excitation light comprising, consisting essentially of, or consisting of continuous light;
(xi) induced by excitation light comprising, consisting essentially of, or consisting of pulsed light;
(xii) induced by excitation light comprising, consisting essentially of, or consisting of light applied at a single incident angle; or
(xiii) induced by excitation light comprising, consisting essentially of, or consisting of light applied at a set of incidence angles.

11. The method of claim 1, comprising:
(a) applying an external electric field to the combined composition, wherein the external electric field is sufficient to cause electrophoretic motion of the fluorescent constructs within the combined composition, wherein
(i) the external electric field comprises, consists essentially of, or consists of: (1) a constant electric field which is applied in a constant direction; (2) a pulsed electric field which is applied in a constant direction; and/or (3) an oscillating electric field which is applied in a constant direction;
(ii) the external electric field comprises, consists essentially of, or consists of: (1) a constant electric field switching between multiple directions; (2) a pulsed electric field switching between multiple directions; and/or (3) an oscillating electric field switching between multiple directions;
(iii) the external electric field comprises, consists essentially of, or consists of a constant electric field which is applied in a constant direction;
(iv) the external electric field comprises, consists essentially of, or consists of a pulsed electric field which is applied in a constant direction; or
(v) the external electric field comprises, consists essentially of, or consists of: (1) an oscillating electric field which is applied in a constant direction; (2) a constant electric field switching between multiple directions; (3) a pulsed electric field switching between multiple directions; and/or (4) an oscillating electric field switching between multiple directions;
(b) a force to the combined composition, thereby reducing or eliminating non-specific interaction between the analyte molecules and the fluorescent constructs;
(c) an acoustic wave to the combined composition, wherein the acoustic wave comprises a high-frequency sound wave including an ultrasound; or
(d) a fluorescence excitation light to the combined composition, wherein:
(i) the fluorescence excitation light is one used in confocal microscopy, Structured Illumination Microscopy (SIM), STochastic Optical Reconstruction Microscopy (STORM), Point-Scanning Two-Photon Microscopy, Scanned Line Angular Projection Microscopy (SLAPMi), Ghost Imaging (GI), and/or Ghost Imaging by Sparsity Constraints (GISC);
(ii) is of controlled phase and wavelength;
(iii) is a standing wave;
(iv) is coherent and the phase of the coherent excitation light is controlled such that the crests and troughs of the excitation light are moved past the fluorescent constructs, sufficient to cause a corresponding oscillation in the fluorescence of the fluorescent constructs;
(v) is an elliptically polarized coherent excitation light, and the ellipticity of the excitation light is controlled such that the crests and troughs of the excitation light are moved past the fluorescent constructs, sufficient to cause a corresponding oscillation in the fluorescence of the fluorescent constructs; or
(vi) is of controlled spatial pattern and wavelength, wherein:
(1) the excitation light is applied as a patterned spatial array across the analytic chamber such that the light intensity varies for different points within the analytic chamber, sufficient to cause changes in the fluorescence of the fluorescent constructs as the fluorescent constructs move between different points within the analytic chamber; or
(2) the patterned spatial array of excitation light is moved across the analytic chamber such that the light intensity varies with time and for different points within the analytic chamber, sufficient to cause changes in the fluorescence of the fluorescent constructs.

12. The method of claim 1, wherein the analyte comprises a protein moiety and the analyte-interacting reagent comprises a protein-binding agent including an antibody or a polynucleotide sequence and the analyte-interacting reagent comprises a sequence capable of hybridizing to the polynucleotide sequence including a sequence complementary to the polynucleotide sequence, wherein the method further comprises melting and/or annealing the hybridized sequences using a temperature control means of an analytic chamber and/or targeted local heating of quantum dots using focused light or using a nutating transparent window to move an image of each fluorescent construct across a surface of an optical detector.

13. The method of claim 1, wherein:
the combining step comprises controllable merging using a pulse of laser or electric field; and/or
the detectable signal is analyzed using optical position tracking comprising using a rotating prism including a Risley Prism Scanner, a nutating disk, a mask, a diffraction grating, a Micro Electro Mechanical System (MEMS), or a Digital Micromirror Device (DMD).

14. A method for formulating or producing a set of aqueous droplets or a set of gel beads, or a population of emulsion droplets, comprising:
a) formulating each aqueous droplet suspended in a water-immiscible liquid matrix to contain a plurality of fluorescent constructs having a combination of fluorescence emission colors, fluorescent construct(s) of each fluorescence emission color having a count and each fluorescent construct having zero, one, or more reagents attached to it, wherein the identity of the reagent is specific to the color of its attached fluorescent construct and/or specific to the combination of colors and counts of the fluorescent constructs within each aqueous droplet;
b) formulating each gel bead in a gel matrix that can be removed by physical or chemical means, wherein each gel bead contains a plurality of fluorescent constructs having a combination of fluorescence emission colors, fluorescent construct(s) of each fluorescence emission color having a count and each fluorescent construct having zero, one, or more reagents attached to it, wherein the identity of the reagent is specific to the color of its attached fluorescent construct and/or specific to the combination of colors and counts of the fluorescent constructs within each gel bead; or
c) mixing a population of first emulsion droplets each comprising one or more first fluorescent construct, a population of second emulsion droplets each comprising one or more second fluorescent construct, and a third emulsion droplet, in any suitable order, in a chamber comprising a liquid matrix which is immiscible with the first, second, and third emulsion droplets; combining the population of first emulsion droplets and the population of second emulsion droplets with the third emulsion droplet to form a combined emulsion droplet in the liquid matrix in the chamber, wherein the first and second fluorescent constructs are present in a defined ratio in the combined emulsion droplet; and dividing the combined emulsion droplet into a population of fourth emulsion droplets, wherein at least 90% of the fourth emulsion droplets in the population comprise the first and second fluorescent constructs in the defined ratio, thereby producing the population of fourth emulsion droplets.

15. A method for analyzing an analyte, comprising:
contacting (i) a first composition comprising a first liquid matrix and a sample encapsulated in the first liquid matrix, with (ii) a second composition comprising a second liquid matrix and a formulation encapsulated in the second liquid matrix, wherein the formulation comprises a plurality of fluorescent constructs and an analyte-interacting reagent attached to one or more of the fluorescent constructs; and combining the sample with the formulation such that an analyte in the sample interacts with the analyte-interacting reagent attached to the one or more of the fluorescent constructs to generate a detectable signal, wherein the analyte is located at the boundary between the first liquid matrix and the sample,
wherein the detectable signal is analyzed for analyzing the presence or absence, an amount or concentration, and/or an activity of the analyte in the sample.

16. The method of claim 15, wherein:
(a) the first liquid matrix and the sample has the same or substantially the same refractive index, wherein the first liquid matrix and the second liquid matrix are the same or different;
(b) the sample is a solution and the analyte is located at the boundary between the first liquid matrix and the sample; or
(c) the first composition comprises a first matrix and an aqueous sample encapsulated in the first matrix, the second composition comprises a second matrix and an aqueous formulation encapsulated in the second matrix, wherein:
(i) the aqueous formulation comprises a plurality of quantum dots and an analyte-binding reagent attached to one or more of the quantum dots; or
(ii) the aqueous sample and the aqueous formulation form a combined aqueous composition that remains encapsulated in oil, and the combined aqueous composition and its encapsulating oil has the same or substantially the same refractive index, wherein the method further comprises detecting a change in diffusance of the plurality of quantum dots encapsulated in oil with increasing temperature and/or decreasing temperature.

17. The method of claim 15, wherein after combining the sample with the formulation, the sample and the formulation remain encapsulated in the first and/or second liquid matrix.

18. The method of claim 15, further comprising:
(a) applying an excitation light to the plurality of fluorescent constructs and the detectable signal comprises fluorescence emission from the plurality of fluorescent constructs, wherein the excitation light comprises a simple ultraviolet light or a pulsed ultraviolet light;
(b) analyzing diffusance of the plurality of fluorescent constructs, which analysis comprises analyzing the detectable signal;
(c) analyzing a change in diffusance of the plurality of fluorescent constructs with increasing temperature and/or decreasing temperature, wherein the change in diffusance is analyzed to provide a melting temperature indicative of an interaction between the analyte and the analyte-interacting reagent; or
(d) continuously monitoring and tracking each fluorescent construct.

19. A method, comprising:
a) for analyzing a cell, contacting (i) a first composition comprising a first liquid matrix and a sample encapsulated in the first liquid matrix, wherein the sample comprises a single cell, with (ii) a second composition comprising a second liquid matrix and a formulation encapsulated in the second liquid matrix, wherein the formulation comprises a plurality of fluorescent constructs and an analyte-interacting reagent attached to one or more of the fluorescent constructs, wherein: (a) the single cell is lysed in the sample to released one or more cellular component or (b) the single cell in not lysed in the sample and a cell-lysing agent is provided in the second composition; and combining the sample with the formulation such that a cellular component interacts with the analyte-interacting reagent attached to the one or more of the fluorescent constructs to generate a detectable signal, wherein the detectable signal is analyzed for analyzing the presence or absence, an amount or concentration, and/or an activity of the cellular component in the single cell;

b) for analyzing an analyte, contacting a first emulsion and a second emulsion with a sample, wherein:

the first emulsion comprises a first formulation encapsulated in a first liquid matrix, wherein the first formulation comprises a first plurality of fluorescent constructs and a first reagent attached to one or more of the fluorescent constructs, and a first free agent;

the second emulsion comprises a second formulation encapsulated in a second liquid matrix, wherein the second formulation comprises a second plurality of fluorescent constructs and a second reagent attached to one or more of the fluorescent constructs, and a second free agent; and the sample comprises an analyte, wherein the first and second reagents are capable of binding to the analyte; and demulsifying the first and second emulsions to allow the first and second plurality of fluorescent constructs and the first and second free agents to diffuse in the sample, wherein at least one of the first plurality of fluorescent constructs and/or at least one of the second plurality of fluorescent constructs are allowed to interact with the analyte in the presence of the first and second free agents to generate a detectable signal, wherein the detectable signal is analyzed for analyzing the presence or absence, an amount or concentration, and/or an activity of the analyte in the sample, and/or a first relationship between the first reagent and the second free agent with the analyte, and/or a second relationship between the second reagent and the first free agent with the analyte;

c) for mapping interactions with a protein, contacting (i) a first composition comprising a first liquid matrix and a sample encapsulated in the first liquid matrix, wherein the sample comprises a protein, with (ii) a second composition comprising a second liquid matrix and a formulation encapsulated in the second liquid matrix, wherein the formulation comprises a plurality of fluorescent constructs and an analyte-interacting reagent attached to one or more of the fluorescent constructs; and combining the sample with the formulation such that the protein in the sample interacts with the analyte-interacting reagent attached to the one or more of the fluorescent constructs to generate a detectable signal, wherein the detectable signal is analyzed for analyzing an interaction between the analyte-interacting reagent and the protein;

d) for analyzing an analyte, contacting a first emulsion droplet, a second emulsion droplet, and a third emulsion droplet, wherein:

the first emulsion droplet comprises a first formulation encapsulated in a first liquid matrix, wherein the first formulation comprises a first plurality of fluorescent constructs and a reagent attached to one or more of the fluorescent constructs;

the second emulsion droplet comprises a second formulation encapsulated in a second liquid matrix, wherein the second formulation comprises a second plurality of fluorescent constructs, and free agent S; and the third emulsion droplet comprises a third formulation encapsulated in a third liquid matrix, wherein the third formulation comprises free agent R; and merging the first, second, and third emulsion droplets to allow the first and second plurality of fluorescent constructs and free agents S and R to diffuse in the merged emulsion droplet, wherein the reagent interacts with free agent R in the presence of free agent S to generate a detectable signal, wherein the detectable signal is indicative of an interaction among the reagent, free agent R, and free agent S; or e) for analyzing an analyte, contacting a first emulsion droplet, a second emulsion droplet, and a third emulsion droplet, wherein:

the first emulsion droplet comprises a first formulation encapsulated in a first liquid matrix, wherein the first formulation comprises a first plurality of fluorescent constructs and a reagent attached to one or more of the fluorescent constructs;

the second emulsion droplet comprises a second formulation encapsulated in a second liquid matrix, wherein the second formulation comprises one or more gel beads encapsulating a second plurality of fluorescent constructs, and free agent S; and the third emulsion droplet comprises a third formulation encapsulated in a third liquid matrix, wherein the third formulation comprises free agent R; and merging the first, second, and third emulsion droplets to allow the first plurality of fluorescent constructs, the one or more gel beads, and free agents S and R to diffuse in the merged emulsion droplet, wherein the second plurality of fluorescent constructs in each gel bead do not diffuse outside of the gel bead, wherein the reagent interacts with free agent R in the presence of free agent S to generate a detectable signal, and wherein the detectable signal is indicative of an interaction among the reagent, free agent R, and free agent S.

* * * * *